(12) United States Patent
Bassaganya-Riera et al.

(10) Patent No.: US 9,839,635 B2
(45) Date of Patent: Dec. 12, 2017

(54) LANTHIONINE SYNTHETASE C-LIKE 2-BASED THERAPEUTICS

(71) Applicant: LANDOS BIOPHARMA, INC., Blacksburg, VA (US)

(72) Inventors: Josep Bassaganya-Riera, Blacksburg, VA (US); Adria Carbo Barrios, Blacksburg, VA (US); Richard Gandour, Blacksburg, VA (US); Julian D. Cooper, Blacksburg, VA (US); Raquel Hontecillas, Blacksburg, VA (US)

(73) Assignee: LANDOS BIOPHARMA, INC., Blacksburg, VA (US)

( * ) Notice: Subject to any disclaimer, the term of this patent is extended or adjusted under 35 U.S.C. 154(b) by 0 days.

(21) Appl. No.: 15/374,556

(22) Filed: Dec. 9, 2016

(65) Prior Publication Data

US 2017/0119762 A1 May 4, 2017

Related U.S. Application Data

(62) Division of application No. 14/662,506, filed on Mar. 19, 2015, now Pat. No. 9,556,146.

(60) Provisional application No. 62/068,322, filed on Oct. 24, 2014, provisional application No. 62/101,164, filed on Jan. 8, 2015.

(51) Int. Cl.
*A61K 31/496* (2006.01)
*A61K 31/4184* (2006.01)
*A61K 31/4439* (2006.01)
*A61K 31/423* (2006.01)

(52) U.S. Cl.
CPC ........ *A61K 31/496* (2013.01); *A61K 31/4184* (2013.01); *A61K 31/423* (2013.01); *A61K 31/4439* (2013.01)

(58) Field of Classification Search
None
See application file for complete search history.

(56) References Cited

U.S. PATENT DOCUMENTS

2011/0275558 A1    11/2011  Bassaganya-Riera et al.

FOREIGN PATENT DOCUMENTS

| WO | WO 1999/033822 A1 | 7/1999 |
| WO | WO 2001/000587 A1 | 1/2001 |
| WO | WO 2005/082905 A1 | 9/2005 |
| WO | WO 2006/114264 A1 | 11/2006 |

OTHER PUBLICATIONS

Barba, G., et al., Recurrent pancreatitis revealing Crohn's disease*Arch Pediatr*, 2002. 9(10): p. 1053-5. .

Bassaganya-Riera, J., et al., Mechanisms of action and medicinal applications of abscisic Acid. *Curr Med Chem*, 2010. 17(5): p. 467-78.
Bassaganya-Riera, J., et al., Abscisic acid regulates inflammation via ligand-binding domain-independent activation of peroxisome proliferator-activated receptor gamma. *J Biol Chem*, 2011. 286(4): p. 2504-16.
Bassaganya-Riera et al., Peroxisome Proliferator-Activated Receptors: the Nutritionally Controlled Molecular Networks that Integrate Inflammation, Immunity and Metabolism. *Current Nutrition & Food Science*. 2005. 1: p. 179-187.
Braverman, I. M., Skin signs of gastrointestinal disease. *Gastroenterology*, 2003. 124(6): p. 1595-614.
Bruzzone, S., et al., Abscisic Acid Is an Endogenous Stimulator of Insulin Release from Human Pancreatic Islets with Cyclic ADP Ribose as Second Messenger, *J Biol Chem*, 2008. 283(47): p. 32188-32197.
Butler D. Cheaper approaches to flu divide researchers. *Nature*. Aug. 30, 2007; 448(7157):976-7.
Camilleri, M., GI clinical research 2002-2003: The year in review. *Clinical Gastroenterology and Hepatology*, 2003. 1: p. 415-420.
CA Registry No. 1389465-82-0, entered into the Registry File on Aug. 12, 2012, supplied by Ukrorgsyntez LTD. Chemical Supplier.
CA Registry No. 1173038-16-8, entered into the Registry File on Aug. 5, 2009, supplied by Ambinter Chemical Supplier.
CDC. National Diabetes Fact Sheet: general information and national estimates on diabetes in the United States, 2005. in U. S. Department of Health and Human Services, Center for Disease Control and Prevention, 2005. 2005. Atlanta, Georgia.
Chua P C et al., "Cyclohexenyl- and Dehydropiperidinyl-Alkynyl Pyridines as Potent Metabotropic Glutamate Subtype 5 (mGlu5) Receptor Antagonists," Bioorganic & Medicinal Chemistry Letters, Pergamon, Amsterdam, NL, vol. 15, No. 20, Oct. 15, 2005, pp. 4589-4593.
Cohen, R.D., et al., The cost of hospitalization in Crohn's disease. *Am J Gastroenterol*, 2000. 95(2): p. 524-30.
Dawood FS, et al. Estimated global mortality associated with the first 12 months of 2009 pandemic influenza A H1N1 virus circulation: a modelling study. *Lancet Infect Dis*. Sep. 2012; 12(9):687-95.
Enserink M. Infectious disease. Old drugs losing effectiveness against flu; could statins fill gap? *Science*. Sep. 23, 2005; 309(5743):1976-7.
Fedson DS. Confronting an influenza pandemic with inexpensive generic agents: can it be done? *Lancet Infect Dis*. Sep. 2008; 8(9):571-6.
Guri et al., Dietary abscisic acid ameliorates glucose tolerance and obesity-related inflammation in db/db mice fed high-fat diets. *Clin Nutr*, 2007. 26(1): p. 107-16.

(Continued)

*Primary Examiner* — Emily A Bernhardt
(74) *Attorney, Agent, or Firm* — Daniel A. Blasiole; Charles S. Sara; DeWitt Ross & Stevens S.C.

(57) ABSTRACT

Provided are compounds that target the lanthionine synthetase C-like protein 2 pathway. The compounds can be used to treat a number of conditions, including infectious disease, autoimmune disease, diabetes, and a chronic inflammatory disease.

22 Claims, 42 Drawing Sheets

(56) References Cited

OTHER PUBLICATIONS

Guri et al., Loss of PPAR gamma in immune cells impairs the ability of abscisic acid to improve insulin sensitivity by suppressing monocyte chemoattractant protein-1 expression and macrophage infiltration into white adipose tissue. *J Nutr Biochem*, 2008. 19(4): p. 216-28.

Guri et al., Abscisic acid synergizes with rosiglitazone to improve glucose tolerance and down-modulate macrophage accumulation in adipose tissue: possible action of the cAMP/PKA/PPAR gamma axis. *Clin Nutr*, 2010. 29(5): p. 646-53.

Guri et al., Abscisic acid ameliorates experimental IBD by downregulating cellular adhesion molecule expression and suppressing immune cell infiltration. *Clin Nutr*, 2010. 29(6): p. 824-31.

Guri et al., Abscisic acid ameliorates atherosclerosis by suppressing macrophage and CD4+ T cell recruitment into the aortic wall. *J Nutr Biochem*, 2010. 21(12): p. 1178-85.

Guri, A.J., et al., T cell PPAR gamma is required for the anti-inflammatory efficacy of abscisic acid against experimental inflammatory bowel disease. *Journal of Nutritional Biochemistry*, 2011. 22(9): p. 812-9.

Guri, A.J., et al., The role of T cell PPAR gamma in mice with experimental inflammatory bowel disease. *BMC Gastroenterology*, 2010. 10:60: p. 1-13.

Hacer Karatas et al., "Synthesis and Potent In Vitro Activity of Novel 1H-Benzimidazoles as Anti-MRSA Agents," Chemical Biology & Drug Design, vol. 80, No. 2, Apr. 30, 2012, pp. 237-244.

Hanauer, S.B. et al., The state of the art in the management of inflammatory bowel disease. *Rev Gastroenterol Disord*, 2003. 3(2): p. 81-92.

Hontecillas, R., et al., Dietary abscisic acid ameliorates influenza-virus-associated disease and pulmonary immunopathology through a PPARgamma-dependent mechanism. *J Nutr Biochem*, 2013. 24(6): p. 1019-27.

Hontecillas, R., et al., Dietary abscisic acid ameliorates influenza virus-associated disease and pulmonary immunopathology through a PPAR g-dependent mechanism. *Journal of Nutritional Biochemistry*, 2012. 24(6): p. 1019-27.

Lindsay, J.O. et al., Review article: the immunoregulatory cytokine interleukin-10—a therapy for Crohn's disease? *Aliment Pharmacol Ther*, 2001. 15(11): p. 1709-16.

Luo Y et al., "Synthesis and In Vitro Cytotoxic Evaluation of Some Thiazolylbenzimidazole Derivatives," European Journal of Medicinal Chemistry, Editions Scientifique Elsevier, Paris, FR, vol. 46, No. 1, Jan. 1, 2011, pp. 417-422.

Lu, P., et al., Molecular modeling of lanthionine synthetase component C-like protein 2: a potential target for the discovery of novel type 2 diabetes prophylactics and therapeutics. *J Mol Model*, 2011. 17(3): p. 543-53.

Lu, P., et al., Computational modeling-based discovery of novel classes of anti-inflammatory drugs that target lanthionine synthetase C-like protein 2. *PLoS One*, 2012. 7(4): p. e34643.

Lu, P., et al., Lanthionine synthetase component C-like protein 2: a new drug target for inflammatory diseases and diabetes. *Curr Drug Targets*, 2014. 15(6): p. 565-72.

Ma, R.C. et al., Diabetes: incidence of childhood type 1 diabetes: a worrying trend. *Nat Rev Endocrinol*, 2009. 5(10): p. 529-30.

Marri, S.R. et al., The education and employment status of patients with inflammatory bowel diseases. *Inflamm Bowel Dis*, 2005. 11(2): p. 171-7.

Mayer, H., et al., Isolation, molecular characterization, and tissue-specific expression of a novel putative G protein-coupled receptor. *Biochim Biophys Acta*, 1998. 1395(3): p. 301-8.

Mayer et al., Molecular cloning, characterization, and tissue-specific expression of human LANCL2, a novel member of the LanC-like protein family. *DNA Seq*, 2001. 12(3): p. 161-6.

Melo F et al., Assessing protein structures with a non-local atomic interaction energy. *J Mol Biol.* Apr. 17, 1998; 277(5):1141-52.

Morris, G.M., et al., AutoDock4 and AutoDockTools4: Automated docking with selective receptor flexibility. *J Comput Chem*, 2009. 30(16): p. 2785-91.

Nesto, R.W., et al., Thiazolidinedione use, fluid retention, and congestive heart failure: a consensus statement from the American Heart Association and American Diabetes Association, Oct. 7, 2003. *Circulation*, 2003. 108(23): p. 2941-8.

Quigley, E., Influenza therapies: vaccines and antiviral drugs. *Drug Discov Today*, 2006. 11(11-12): p. 478-80.

Rothberg, M.B. et al., Complications of viral influenza. *Am J Med.* 2008. 121(4): p. 258-64.

Smiles Translator and Converter. http://cactus.nci.nih.gov/translate, (2011).

Sparre, T., et al., Unraveling the pathogenesis of type 1 diabetes with proteomics: present and future directions. *Mol Cell Proteomics*, 2005. 4(4): p. 441-57.

Spunt, S., et al., Cancer Epidemiology in Older Adolescents and Young Adults 15 to 29 Years of Age, in SEER AYA Monograph. 2008, National Cancer Institute: Bethesda, MD. p. 123-133.

Stenson, W.F., Interleukin-4 hyporesponsiveness in inflammatory bowel disease: immune defect or physiological response? *Gastroenterology*, 1995. 108(1): p. 284-6.

Sturla, L., et al., LANCL2 is necessary for abscisic acid binding and signaling in human granulocytes and in rat insulinoma cells. *J Biol Chem*, 2009. 284(41): p. 28045-57.

Sturla, L., et al., Binding of abscisic acid to human LANCL2. *Biochem Biophys Res Commun*, 2011. 415(2): p. 390-5.

Suarez-Pinzon et al., Combination therapy with glucagon-like peptide-1 and gastrin induces beta-cell neogenesis from pancreatic duct cells in human islets transplanted in immunodeficient diabetic mice. *Cell Transplant*, 2008. 17(6): p. 631-40.

Trott et al., Software News and Update AutoDock Vina: Improving the Speed and Accuracy of Docking with a New Scoring Function, Efficient Optimization, and Multithreading. *Journal of Computational Chemistry*, 2010. 31(2): 455-461.

Vehik, K., et al., Increasing incidence of type 1 diabetes in 0- to 17-year-old Colorado youth. *Diabetes Care*, 2007, 30(3): p. 503-9.

Wysowski, D.K. et al., Rapid increase in the use of oral antidiabetic drugs in the United States, 1990-2001. *Diabetes Care*, 2003. 26(6): p. 1852-5.

| Example No. | Compound name | Structure | Predicted Binding Affinity to LANCL2 | SPR Affinity to LANCL2 (Kd) |
|---|---|---|---|---|
| 1 | BT-11 | 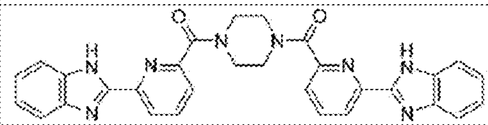 | -11.2 | 7.7 |
| 2 | BT-12 | 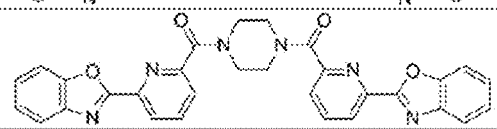 | -10.9 | NB[*1] |
| 3 | BT-14 | 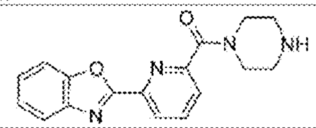 | -9.3 | NB[*1] |
| 4 | BT-15 | 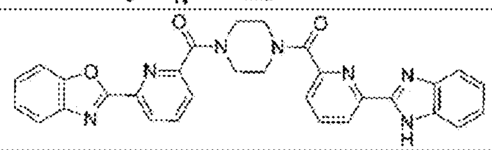 | -9.9 | 21.4 |
| 5 | BT-13 | 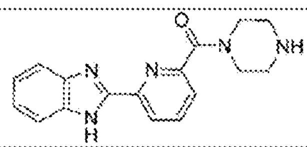 | -7.2 | NB[*1] |
| 6 | BT-4 | 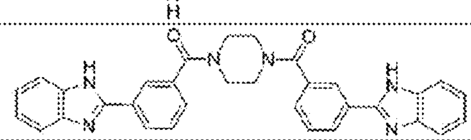 | -9.8 | 84.3 |
| 7 | BT-6 | 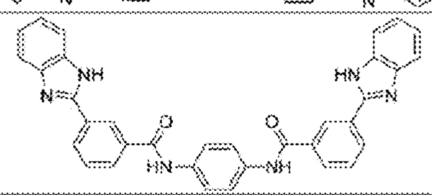 | -8.6 | 18.2 |
| 8 | BT-16 | 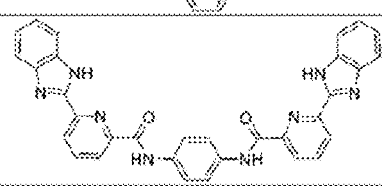 | -7.6 | 4.85e-06 |
| 9 | BT-3 | 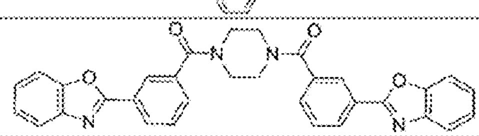 | -10.1 | Not measured |

*1: NB refers to "No binding"

Figure 1A

| Example No. | Compound name | Structure | Predicted Binding Affinity to LANCL2 | SPR Affinity to LANCL2 (Kd) |
|---|---|---|---|---|
| 10 | BT-5 | 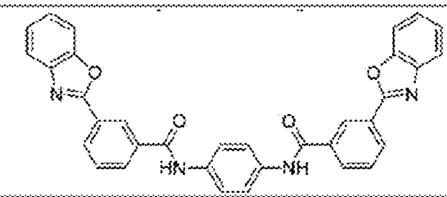 | -8.9 | Not measured |
| 11 | BT-17 | 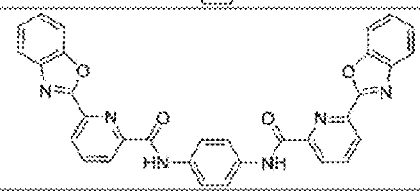 | -7.6 | Not measured |
| 12 | BT-ABA-25 | 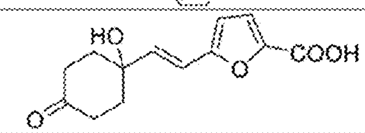 | -7.5 | 1.77e-04 |
| 13 | BT-ABA-5a | 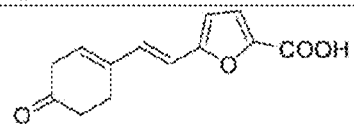 | -9.5 | 1.17e-05 |
| 14 | BT-ABA-6 | 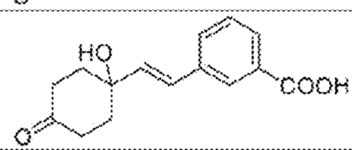 | -7.5 | 163 |
| 15 | BT-ABA-13 | 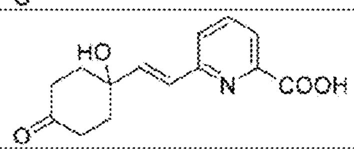 | -7.6 | 4.65e-06 |
| 16 | BT-ABA-16 | 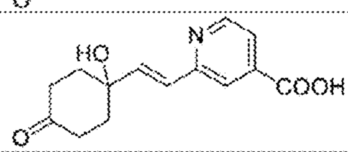 | -7.6 | 4.85e-06 |
| REF 18 | 61610 N1,N4-bis(3-(1H-benzo[d]imidazol-2-yl)phenyl)terephthalamide | | -9.1 | 6.2 |
| REF 18 | ABA | | -7.5 | 2.3 |

Figure 1B

LANTHIONINE SYNTHETASE C-LIKE 2-BASED THERAPEUTICS

CROSS-REFERENCE TO RELATED APPLICATIONS

This application is a divisional of U.S. patent application Ser. No. 14/662,506 filed Mar. 19, 2015, and issued as U.S. Pat. No. 9,556,146 on Jan. 31, 2017, which claims priority under 35 USC §119(e) to U.S. Provisional Patent Application 62/068,322 filed Oct. 24, 2014, and U.S. Provisional Patent Application 62/101,164 filed Jan. 8, 2015, the entirety of each of which is incorporated herein by reference.

STATEMENT REGARDING FEDERALLY SPONSORED RESEARCH

This invention was made partially with U.S. Government support from the United States National Institutes of Health under SBIR grant 1R43DK097940-01A1 and STTR grant 1R41DK099027-01A1 awarded to BioTherapeutics Inc. The U.S. Government has certain rights in the invention.

FIELD OF THE INVENTION

The present invention relates to the field of medical treatments for diseases and disorders. More specifically, the present invention relates to classes of biologically active compounds that treat and prevent inflammatory and immune mediated diseases such as inflammatory bowel disease, rheumatoid arthritis, psoriasis, multiple sclerosis, and type 1 diabetes, as well as chronic inflammatory diseases and disorders such as insulin resistance, impaired glucose tolerance, prediabetes, type 2 diabetes, and obesity-related inflammation, among others.

BACKGROUND

Lanthionine C-like protein 2 (LANCL2) (also called "lanthionine synthetase C-like protein 2" or "lanthionine synthetase component C-like protein 2") is a signaling pathway protein that is expressed immune cells, gastrointestinal tract, neurons, testis and pancreas [1]. Activating the LANCL2 pathway increases insulin sensitivity and reduces inflammation associated with various autoimmune, inflammatory and metabolic conditions. Results of in vivo and in vitro testing in mice showed that using compounds targeting this pathway reduce glucose levels 2× in glucose tolerance tests as compared to controls and provided equivalent levels to prescription AVANDIA® (GlaxoSmithKline plc, Brentford, England)—an effective treatment but with significant side-affects. Targeting the LANCL2 pathway also reduces gut inflammation by 90% with a corresponding 4× reduction in the number of lesions. The results from this testing and other validations of the pathway are published in 12 peer-reviewed journal articles [2-13].

Within the category of autoimmune-related inflammation there is currently a global pandemic of autoimmune disorders such as inflammatory bowel disease (IBD), systemic lupus, rheumatoid arthritis, type 1 diabetes, psoriasis, multiple sclerosis. There is also a pandemic of chronic metabolic inflammatory diseases including metabolic syndrome, obesity, prediabetes, cardiovascular disease, and type 2 diabetes. Current treatments are moderately effective but are expensive and have serious side effects. The route of administration for the most effective treatments for autoimmune diseases, such as anti-TNF antibodies, is via IV or subcutaneous injection, requiring visits to clinics/surgeries and frequent monitoring. The unique mode of action of LANCL2 provides for orally administered therapeutics that are as effective as anti-TNF antibodies but without the side effects and high cost. Given the epidemic of inflammatory and autoimmune diseases as a whole, the LANCL2 pathway has the potential to significantly impact millions of patients.

Abscisic acid ("ABA") is one of the natural compounds found in the original screening process that binds to LANCL2.

There is an enormous number of compounds described in the field of synthetic organic chemistry. Various compounds are provided by the following references: WO1997/036866 to Diana et al., WO 2006/053109 to Sun et al., WO 2006/080821 to Kim et al., WO 2007/019417 to Nunes et al., WO 2009/067600 and WO 2009/067621 to Singh et al., WO 2008/079277 to Adams et al., JP 2008/056615 to Urasoe et al., WO 2011/066898 to Stoessel et al., US 2013/0142825 to Bassaganya-Riera et al., and U.S. Pat. No. 7,741,367 to Bassaganya-Riera et al. Some of the compounds described in these references are known to activate the LANCL2 pathway and others are not.

There is a need to develop novel ligands of the LANCL2 pathway to allow treatments to be tailored specifically to individual diseases and to potentially maximize their efficacy.

This application therefore describes a series of classes of compounds that have been developed by novel medicinal chemistry approaches, and screened using in silico, in vitro, and in vivo techniques, to maximize their ability to bind to the LANCL2 protein and thus to effect a beneficial response in various disease conditions, including but not limited to, autoimmune, chronic inflammatory, metabolic, and infectious diseases.

SUMMARY OF THE INVENTION

The invention provides compounds comprising formula Z—Y-Q-Y'—Z' or a pharmaceutically acceptable salt or ester thereof,
wherein:
Z is:

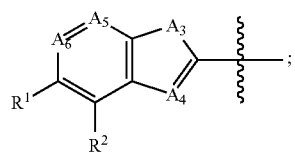

Y is:

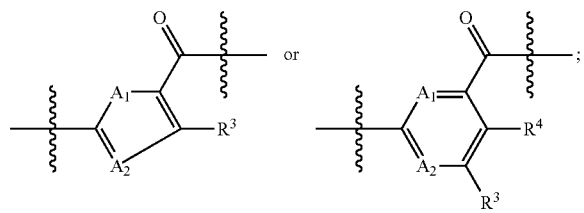

Q is piperazine-1,4-diyl; 2,5-diazabicyclo[2.2.1]heptane-2,5-diyl; 2,5-diazabicyclo[2.2.2]octane-2,5-diyl; 1,4-diazepane-1,4-diyl; benzene-1,4-diamine-$N^1,N^4$-diyl; ethane-1,2-diamine-$N^1,N^2$-diyl; $N^1,N^2$-dialkylethane- 1,2-diamine-$N^1,N^2$-diyl; propane-1,3-diamine-$N^1,N^3$-diyl; $N^1,N^3$-dialkylpropane-1,3-diamine-$N^1,N^3$-diyl; 1,4-diaminoanthracene-9,10-dione-1,4-diyl; $C_6$ arene-1,4-diamine-$N^1,N^4$-diyl wherein the arene is substituted with one to four substituents in the 2, 3, 5, or 6 positions and wherein the substituents are independently selected from the group consisting of —C(O)O ($C_1$ to $C_6$)alkyl, OH, O($C_1$ to $C_6$)alkyl, ($C_1$ to $C_6$)alkyl, $CF_3$, F, Cl, and Br; or substituted piperazine-1,4-diyl wherein the piperazine is substituted with one to eight substituents in the 2, 3, 5, or 6 positions and wherein the substituents are independently selected from the group consisting of ($C_1$ to $C_6$)alkyl, aryl, aryl($C_1$ to $C_6$)alkyl, C(O)OH, and C(O)O($C_1$ to $C_6$)alkyl;

Y' is:

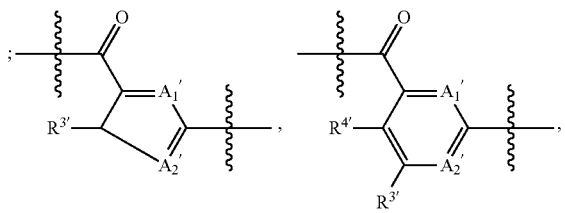

or a single bond; and

Z' is:

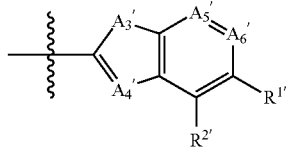

or $R^5$;

wherein:
Y' is a single bond only when Z' is $R^5$;
$A_1$ and $A_1'$ are each independently N, N($C_1$ to $C_6$)alkyl, O, S, or $CR^6$;
$A_2$ and $A_2'$ are each independently N or $CR^7$;
$A_3$ and $A_3'$ are each independently $NR^8$, O, or S;
$A_4$ and $A_4'$ are each independently N or $CR^9$;
$A_5$ and $A_5'$ are each independently N or $CR^{10}$;
$A_6$ and $A_6'$ are each independently N or $CR^{11}$;
$R^1$, $R^{1'}$, $R^2$, $R^{2'}$, $R^3$, $R^{3'}$, $R^4$, $R^{4'}$, $R^5$, $R^6$, $R^7$, $R^8$, $R^9$, $R^{10}$, and $R^{11}$ are each independently selected from the group consisting of hydrogen; alkyl; halo; trifluoromethyl; dialkylamino wherein each alkyl is independently selected; —$NH_2$; alkylamino; arylalkyl; heteroarylalkyl.; heterocycloalkyl; substituted heterocycloalkyl substituted with 1 to 2 substituents independently selected from the group consisting of —C(O)OH, —C(O)O($C_1$ to $C_6$)alkyl, ($C_1$ to $C_6$)alkyl, —$CF_3$, F, Cl, and Br; and substituted heteroarylalkyl;
wherein the substituted heteroarylalkyl is substituted with 1 to 3 substituents independently selected from the group consisting of —$NH_2$; —NH($C_1$ to $C_6$)alkyl; —N(($C_1$ to $C_6$)alkyl)$_2$ wherein each alkyl is independently selected; alkyl; halo; aryl; substituted aryl substituted with 1 to 3 substituents independently selected from the group consisting of —$SO_2R^{12}$, —$OR^{13}$, -halo, —CN, —$CF_3$, aminoalkyl-, —$S(O)R^{14}$, and alkyl; heterocycloalkyl; heteroaryl; substituted aryl substituted with 1 to 3 substituents independently selected from the group consisting of alkyl, —$CF_3$, F, Cl, and Br; alkylamino-; heterocycloalkyl-alkyl-amino-; alkylaminoalkylamino-; —$NHC(O)OR^{15}$; —$NHC(O)NR^{16}R^{17}$; —$C(O)NR^{16}R^{17}$; and substituted heteroaryl substituted with 1 to 3 substituents selected from the group consisting of alkyl, halo, CN, $NH_2$, —NH($C_1$-$C_6$ alkyl), —N($C_1$-$C_6$ alkyl)$_2$ wherein each alkyl is independently selected, —$CF_3$, and substituted aryl substituted with 1 to 3 substituents independently selected from the group consisting of —$S(O)_2R^{15}$ and —CN;
wherein $R^{12}$, $R^{13}$, $R^{14}$, $R^{15}$, $R^{16}$, and $R^{17}$ are each independently selected from the group consisting of $C_1$-$C_6$ alkyl, dialkylamino comprising independently selected $C_1$-$C_6$ alkyl, —$NH_2$, alkylamino, heterocycloalkyl, and substituted heterocycloalkyl substituted with one to two substituents independently selected from the group consisting of —C(O)O($C_1$-$C_6$ alkyl) and $C_1$-$C_6$ alkyl.

In some compounds, at least one of $A_3$ and $A_3'$ is O or S. In some compounds, one or both of $A_1$ and $A_1'$ is N. In some compounds, one or both of $A_2$ and $A_2'$ is CH, $A_3$ is NH, $A_4$ is N, $A_5$ is CH, and $A_6$ is CH. In some compounds, one or both of $A_2$ and $A_2'$ is CH, one or both of $A_3$ and $A_3'$ is NH, one or both of $A_4$ and $A_4'$ is N, one or both of $A_5$ and $A_5'$ is CH, and one or both of $A_6$ and $A_6'$ is CH. In some compounds, Q is piperazine-1,4-diyl; 2,5-diazabicyclo[2.2.1.]heptane-2,5-diyl; 2,5-diazabicyclo[2.2.2]octane-2,5-diyl; 1,4-diazepane-1,4-diyl; $N^1,N^2$-dialkylethane-1,2-diamine-$N^1,N^2$-diyl; $N^1,N^3$-dialkylpropane-1,3-diamine-$N^1,N^3$-diyl; 1,4-diaminoanthracene-9,10-dione-1,4-diyl; $C_6$ arene-1,4-diamine-$N^1,N^4$-diyl wherein the arene is substituted with one to four substituents in the 2, 3, 5, or 6 positions and each substituent is independently selected from the group consisting of —C(O)O($C_1$ to $C_6$)alkyl, OH, O($C_1$ to $C_6$)alkyl, ($C_1$ to $C_6$)alkyl, $CF_3$, F, Cl, and Br; or substituted piperazine-1,4-diyl wherein the piperazine is substituted with one to eight substituents in the 2, 3, 5, or 6 positions and each substituents is independently selected from the group consisting of ($C_1$ to $C_6$)alkyl, aryl, aryl($C_1$ to $C_6$)alkyl, C(O)OH, and C(O)O($C_1$ to $C_6$)alkyl.

In some compounds, the formula Z—Y-Q-Y'—Z' is:

III-55

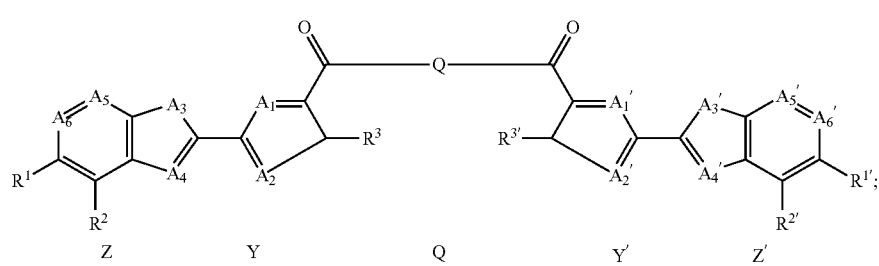

-continued

III-65

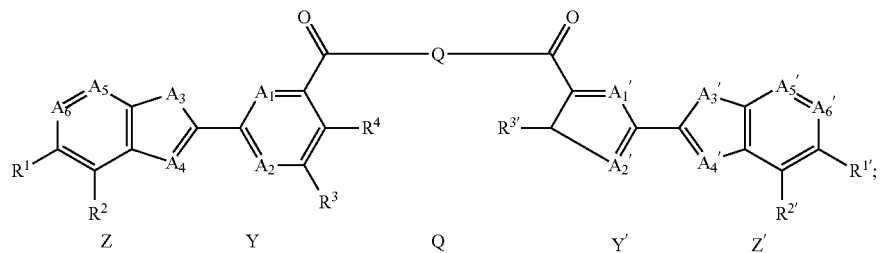

III-66

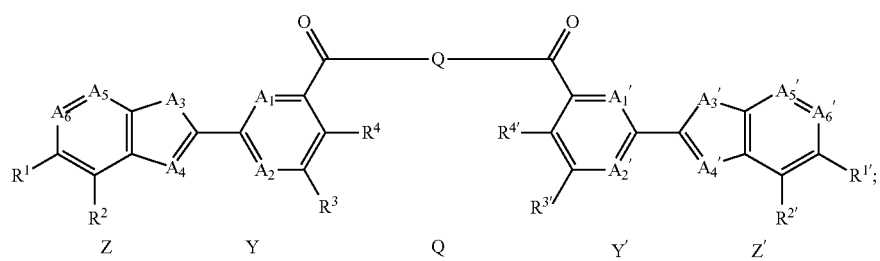

or salts thereof. In some compounds, members of one or more pairs selected from the group consisting of $A_1$ and $A_1'$, $A_2$ and $A_2'$, $A_3$ and $A_3'$, $A_4$ and $A_4'$, $A_5$ and $A_5'$, $A_6$ and $A_6'$, $R_1$ and $R_1'$, $R_2$ and $R_2'$, $R_3$ and $R_3'$, and $R_4$ and $R_4'$ are the same. In some compounds, members of one or more pairs selected from the group consisting of $A_1$ and $A_1'$, $A_2$ and $A_2'$, $A_3$ and $A_3'$, $A_4$ and $A_4'$, $A_5$ and $A_5'$, $A_6$ and $A_6'$, $R_1$ and $R_1'$, $R_2$ and $R_2'$, $R_3$ and $R_3'$, and $R_4$ and $R_4'$ are different. In some compounds, members of each pair selected from the group consisting of $A_1$ and $A_1'$, $A_2$ and $A_2'$, $A_3$ and $A_3'$, $A_4$ and $A_4'$, $A_5$ and $A_5'$, $A_6$ and $A_6'$, $R_1$ and $R_1'$, $R_2$ and $R_2'$, $R_3$ and $R_3'$, and $R_4$ and $R_4'$ are the same. In some compounds, members of each pair selected from the group consisting of $A_1$ and $A_1'$, $A_2$ and $A_2'$, $A_3$ and $A_3'$, $A_4$ and $A_4'$, $A_5$ and $A_5'$, $A_6$ and $A_6'$, $R_1$ and $R_1'$, $R_2$ and $R_2'$, $R_3$ and $R_3'$, and $R_4$ and $R_4'$ are different.

In some compounds, the formula Z—Y-Q-Y'—Z' is:

IV-55

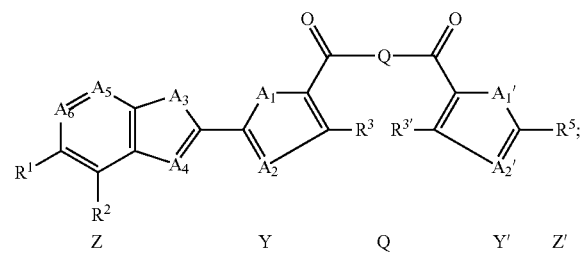

IV-56

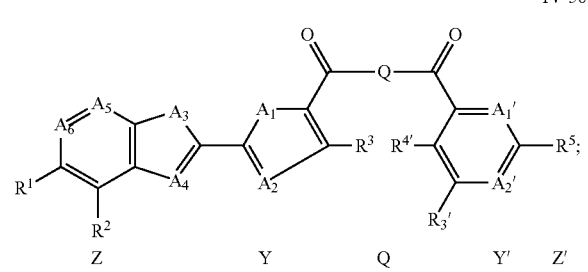

-continued

IV-65

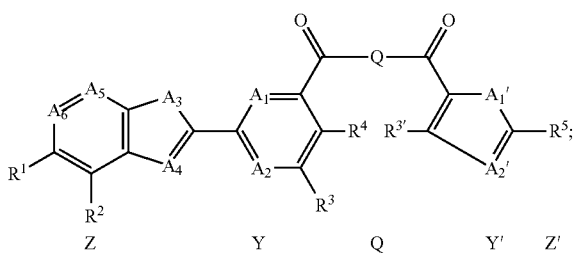

or salts thereof.

Some compounds of the invention have the structure of:

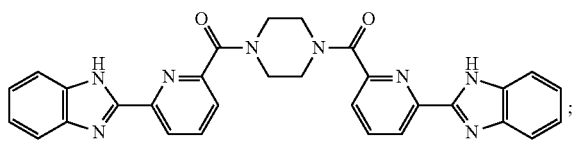

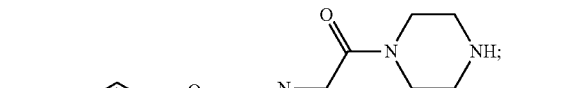

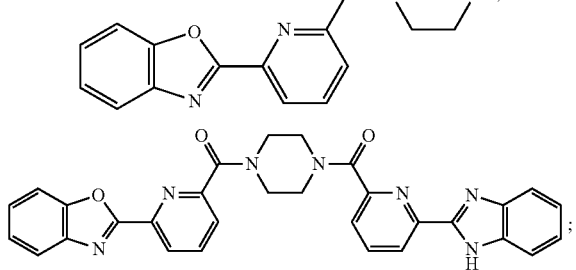

-continued

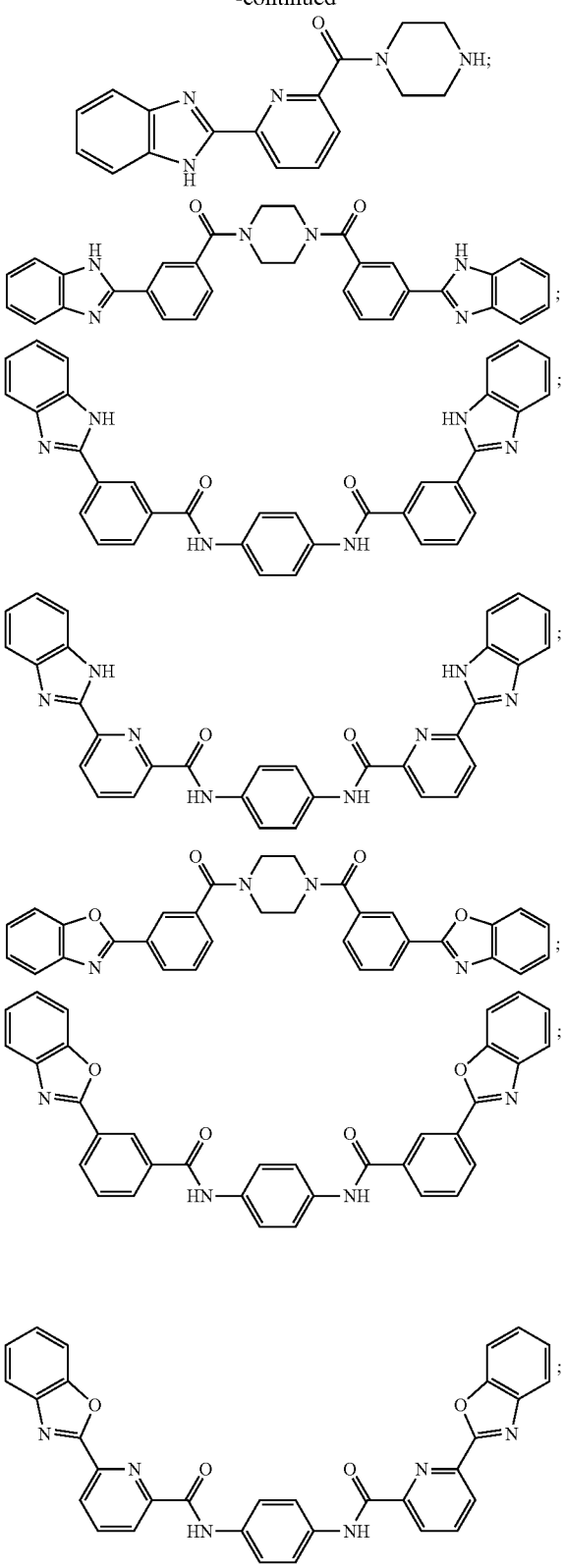

or salts thereof.

The invention also provides compounds comprising formula A-B-C or a pharmaceutically acceptable salt or ester thereof, wherein:
A is:

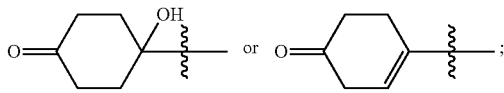 [SMILES: *C1(O)CCC(=O)CC1 ; *C1=CCC(=O)CC1]

B is:

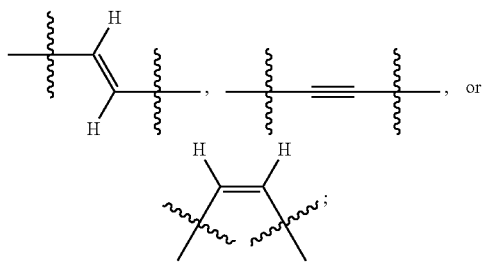

and
C is:

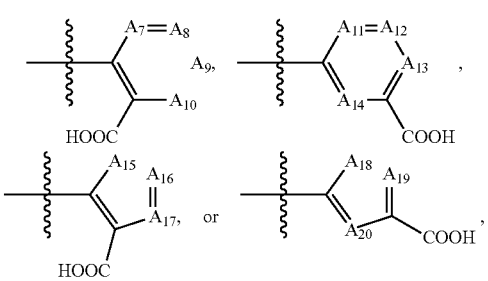

wherein:
$A_7$, $A_8$, $A_9$, $A_{10}$, $A_{11}$, $A_{12}$, $A_{13}$, and $A_{14}$ are each independently selected from CH, $CR^{18}$, and N;
$A_{15}$, $A_{16}$, $A_{17}$, $A_{18}$, $A_{19}$, and $A_{20}$ are each independently selected from CH, $CR^{19}$, N, $NR^{20}$, O, and S, with the proviso that only one of $A_{15}$, $A_{16}$, and $A_{17}$ can be N, $NR^{20}$, O, or S and only one of $A_{18}$, $A_{19}$, and $A_{20}$ can be N, $NR^{20}$, O, or S;
$R^{18}$ and $R^{19}$ are each independently selected from $C_1$-$C_6$ alkyl; $C_1$-$C_6$ dialkylamino, wherein each $C_1$-$C_6$ alkyl is independently selected; —$NH_2$; alkylamino; heterocycloalkyl; and substituted heterocycloalkyl, wherein the substituted heterocycloalkyl is substituted with one to two substituents independently selected from the group consisting of: —C(O)O($C_1$-$C_6$ alkyl) and $C_1$-$C_6$ alkyl; wherein in compounds with more than one $CR^{18}$ each $R^{18}$ is independently selected, and in compounds with more than one $CR^{19}$ each $R^{19}$ is independently selected; and
$R^{20}$ is $C_1$-$C_6$ alkyl.

In some compounds B is:

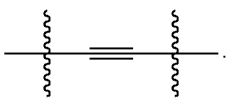

Some compounds have a structure of:

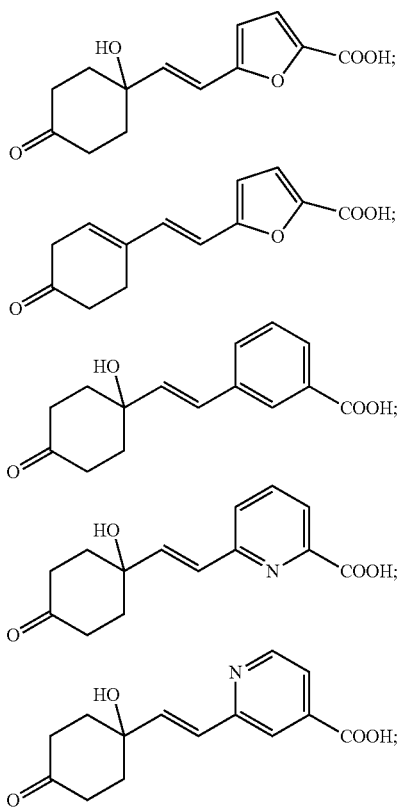

or salts thereof.

The invention also provides methods of treating a condition in an animal with any one or more of the compounds described herein. The methods comprise administering an effective amount of one or more of the compounds described herein to the animal. The condition may be selected from the group consisting of an infectious disease, an autoimmune disease, diabetes, and a chronic inflammatory disease. In some methods, the infectious disease comprises a viral disease, such as influenza infection. In some methods, the autoimmune disease comprises an autoimmune inflammatory disease, such as inflammatory bowel disease, including ulcerative colitis and/or Crohn's disease. In some methods, the diabetes is selected from the group consisting of type 1 diabetes and type 2 diabetes. In some methods, the chronic inflammatory disease comprises metabolic syndrome. In some methods, the methods comprise administering an amount of a compound effective to increase activity of LANCL2, decrease inflammation, and/or increase anti-inflammatory effects.

The invention also provides compounds for use in treating a condition in an animal with any one or more of the compounds described herein. The compounds for such use include any compounds described herein. The use may comprise administering an effective amount of one or more of the compounds described herein to the animal, wherein the condition is selected from the group consisting of an infectious disease, an autoimmune disease, diabetes, and a chronic inflammatory disease. In some versions, the infectious disease comprises a viral disease, such as influenza infection. In some versions, the autoimmune disease comprises an autoimmune inflammatory disease, such as inflammatory bowel disease, including ulcerative colitis and/or Crohn's disease. In some versions, the diabetes is selected from the group consisting of type 1 diabetes and type 2 diabetes. In some versions, the chronic inflammatory disease comprises metabolic syndrome. In some versions, the compound is effective to increase activity of LANCL2, decrease inflammation, and/or increase anti-inflammatory effects.

The objects and advantages of the invention will appear more fully from the following detailed description of the preferred embodiment of the invention made in conjunction with the accompanying drawings.

BRIEF DESCRIPTION OF THE DRAWINGS

FIGS. 1A and 1B. Computational prediction of binding of compounds to LANCL2 and biochemical experimental validation using SPR.

DETAILED DESCRIPTION OF THE INVENTION

General Definitions

Figure 2:
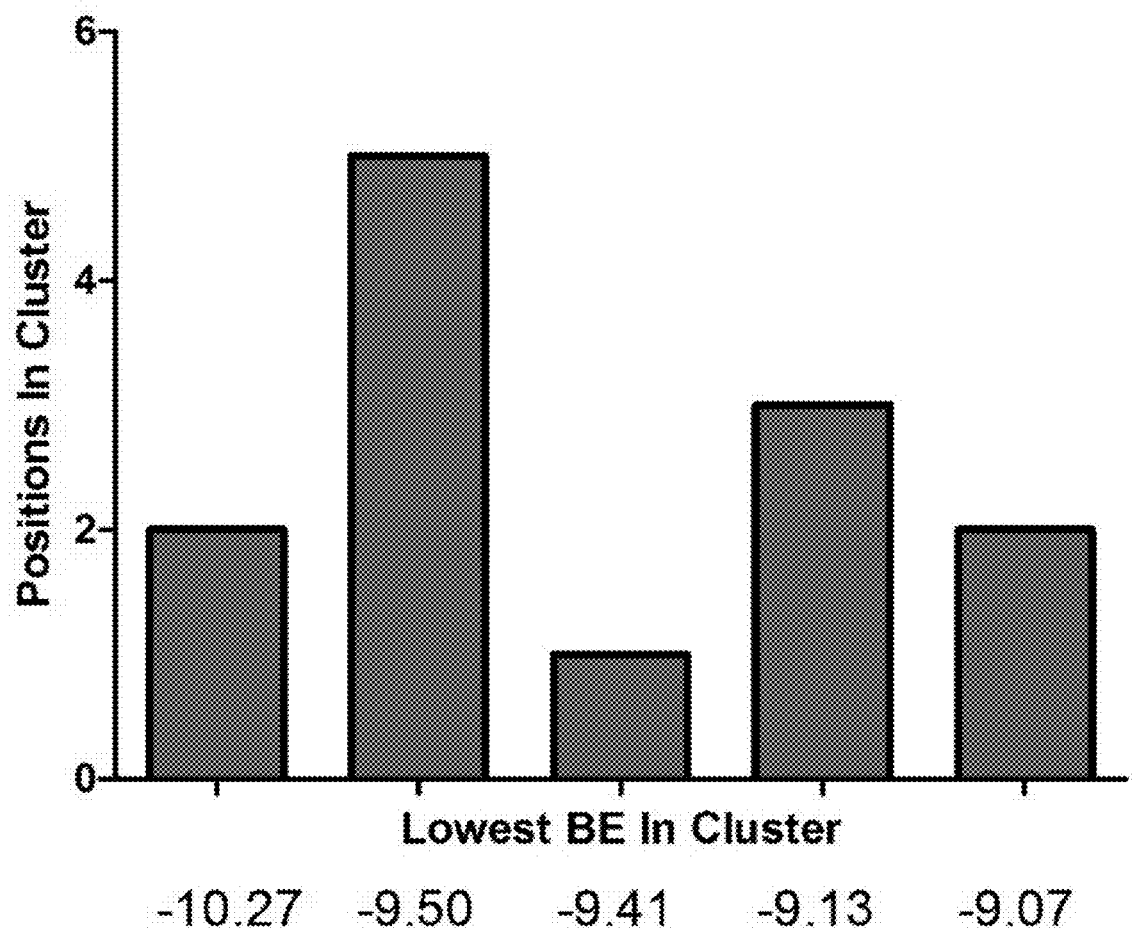
FIG. 2. Clustering histogram for the top five clusters of NSC6160. One hundred docking runs were performed with NSC6160 docked to LANCL2 using AutoDock Tools. The RMSD cluster tolerance was 2 Å. Binding energies are listed in kJ/mol.

Unless otherwise stated, the following definitions are used throughout he present application:

Analysis of Variance (ANOVA): Arithmetic process for partitioning the overall variation in data sets into specific components based on sources of variation. It has been used to determine whether numerical differences between treatment groups are statistically significant.

Adipogenesis: The process by which new adipocytes or fat storage cells are generated.

Allele: One of a number of viable DNA coding of the same gene.

Conjugated diene: A molecule containing two double bonds separated by a single bond.

Db/db mice: Term used to define a type of mouse which lacks both alleles of a long isoform of leptin receptor. This deficiency results in a high predisposition to developing type 2 diabetes. See examples below for further discussions on Db/db mice.

Enantiomer: Optical isomer; chemical classification of molecules based on their ability to rotate the plain of polarization clockwise (+) or anti-clockwise (-).

Glycemia: Concentration of glucose in blood.

Hyperglycemia: Increased concentrations of glucose in blood beyond the normal ranges.

Hyperinsulinemia: Increased concentrations of insulin in blood beyond the normal ranges.

Insulinemia: Concentration of insulin in blood.

Insulin resistance: Inability of tissues to respond to insulin and take up glucose from the blood.

Substantially pure: Having a purity of at least 90% by weight, preferably at least 95% by weight such as at least 98%, 99% or about 100% by weight.

Type 2 diabetes or non-insulin dependent diabetes mellitus: Term referring to a common type of diabetes caused by an unresponsiveness of cells to the actions of insulin. If the cells do not respond to insulin, they are unable to take up glucose from blood, which results in glucotoxicity. In addition, the cells are deprived from the energy derived from glucose oxidation.

IBD: Inflammatory bowel disease (IBD) involves chronic inflammation of all or part of your digestive tract. IBD primarily includes ulcerative colitis and Crohn's disease. Both usually involve severe diarrhea, pain, fatigue and weight loss. IBD can be debilitating and sometimes leads to life-threatening complications.

Ulcerative colitis (UC): UC is an IBD that causes long-lasting inflammation and sores (ulcers) in the innermost lining of your large intestine (colon) and rectum.

Crohn's Disease: Crohn's disease is an IBD that cause inflammation of the lining of your digestive tract. In Crohn's disease, inflammation often spreads deep into affected tissues. The inflammation can involve different areas of the digestive tract—the large intestine, small intestine or both.

IL-10: Interleukin-10 (IL-10), also known as human cytokine synthesis inhibitory factor (CSIF), is an anti-inflammatory cytokine. In humans, IL-10 is encoded by the IL10 gene.

FOXP3: FOXP3 (forkhead box P3) also known as scurfin is a protein involved in immune system responses. A member of the FOX protein family, FOXP3 appears to function as a master regulator (transcription factor) in the development and function of regulatory T cells.

TNT-alpha: Tumor necrosis factor (TNF, cachexin, or cachectin, and formerly known as tumor necrosis factor alpha or TNFα) is cytokine involved in systemic inflammation and is a member of a group of cytokines that stimulate the acute phase reaction.

MCP 1: Monocyte chemoattractant protein-1. An older term for a CC cytokine which is critical for development of atherosclerotic lesions, found in endothelial cells, macrophages and in vascular smooth muscle cells of patients undergoing coronary artery bypass procedures. The officially preferred term is now chemokine (C—C motif) ligand 2.

Interferon gamma: Interferon gamma is a pro-inflammatory dimerized soluble cytokine that is the only member of the type II class of interferons.

Type 1 diabetes: Type 1 diabetes, once known as juvenile diabetes or insulin-dependent diabetes, is a chronic condition in which the pancreas produces little or no insulin, a hormone needed to allow sugar (glucose) to enter cells to produce energy.

Leukocytic infiltration: Leukocyte infiltration refers to the process of moving or infiltrating of the leukocytes into the injured tissue to begin the repair process.

Chemical Definitions

The term "alkyl," by itself or as part of another substituent, means, unless otherwise stated, a fully saturated, straight,branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above except that it contains one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above except that it contains one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

Typically, alkyl, alkenyl, alkynyl, alkylene, alkenylene, and alkynylene groups will have from 1 to 24 carbon atoms. Those groups having 10 or fewer carbon atoms are preferred in the present invention. The term "lower" when applied to any of these groups, as in "lower alkyl" or "lower alkylene," designates a group having 10 or fewer carbon atoms.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, and alkynylene moieties. Additionally, these groups may be pendent from, or integral to, the carbon chain itself.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., $CF_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "halogen" or "halo" is used herein to refer to fluorine, bromine, chlorine, and iodine atoms.

The term "hydroxy" is used herein to refer to the group —OH.

The term "amino" is used to designate NRR', wherein R and R' are independently H, alkyl, alkenyl, alkynyl, aryl, or substituted analogs thereof. "Amino" encompasses "alkylamino," denoting secondary and tertiary amines, and "acylamino" describing the group RC(O)NR'.

Administration

In the course of the methods of the present invention, a therapeutically effective amount of compounds of the invention can be administered to an animal, including mammals and humans, in many ways. While in the preferred embodiment, the compounds of the invention are administered orally or parenterally, other forms of administration such as through medical compounds or aerosols are also contemplated.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used. The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may he used. Included among these is the non-limiting example of water.

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of for example, dichlorofluoromethane, propane or nitrogen may be used as the spraying agent.

The compounds of the invention may be administered to an animal, including mammals and humans, in need thereof as a pharmaceutical composition, such as tablets, capsules, solutions, or emulsions. Administration of other forms of the compounds described in this invention, including but not limited to esters thereof, pharmaceutically-suitable salts thereof, metabolites thereof, structurally related compounds thereof, analogs thereof, and combinations thereof, in a single dose or a multiple dose, are also contemplated by the present invention.

The compounds of the invention may also be administered to an animal in need thereof as a nutritional additive, either as a food or nutraceutical supplement.

The terms "preventing," "treating," or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. It is preferably from about 0.0001 g to about 20 g (more preferably 0.01 g to 1 g, such as 0.05 g to 0.5 g) of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, heads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Preferably the unit dosage of compounds described in the present invention is from 1 mg to 1000 mg (more preferably from 50 mg to 500 mg). The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. Preferably, the unit dosage of compounds in the food supplements is from 1 mg to 1000 mg (more preferably from 50 mg to 500 mg).

In general, the term carrier may be used throughout this application to represent a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention.

Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans.

For instance, an amount of a compound effective to treat or prevent type 2 diabetes, prediabetes, type 1 diabetes, impaired glucose tolerance, insulin resistance, ulcerative colitis, or Crohn's disease, or any other condition described herein in an animal can range from 0.1-10,000 mg/kg/day. A preferred effective amount of compound is 1 to 5,000 mg/kg/day, with a more preferred dose being 2 to 100 mg/kg/day. The upper limit of the effective amount to be administered is not critical, as the compounds are relatively non-toxic as our toxicology data demonstrates. The effective amount of compound is most effective in treating or preventing ulcerative colitis, Crohn's disease, type 2 diabetes, type 1 diabetes, pre-diabetes, metabolic syndrome, impaired glucose tolerance, and insulin resistance of an animal when administered to an animal for periods ranging from about 7 to 100 days, with a preferred period of 15 to 50 days, and a most preferred period of 30 to 42 days.

An amount of compound most effective in preventing over-activation of the immune system can range from 0.1 to 500 mg/kg/day, with a preferred dose of 1 to 150 mg/kg/day.

When the effective amount of the compound of the present invention is administered in a nutritional, therapeutic, medical, or veterinary composition, the preferred dose ranges from about 0.01 to 2.0% wt/wt to the food or nutraceutical product.

In certain other embodiments, the present invention provides for use of LANCL2-binding compounds and also structurally related compounds, such as a compound selected from the group consisting the compound, esters thereof, pharmaceutically suitable salts thereof, metabolites thereof, structurally related compounds thereof, or combinations thereof in the treatment and prevention of IBD and GI tract inflammation.

In addition, in general, the present invention relates to inhibition of inflammation in the GI tract, wherein the relevant components include the stomach, small intestine, large intestine, and rectum. The effect results from the exposure of compound to various cells types in the body that induces a biological effect. The cells may include those from GI tract tissues, immune cells (i.e. macrophages, monocytes, lymphocytes), or epithelial cells. In certain embodiments, the invention provides for treating subjects with a compound of the invention, for example as a dietary supplement, to reduce or prevent inflammation related to inflammatory bowel disease, either Crohn's Disease or Ulcerative Colitis. The present invention also contemplates administering the compounds of the invention to the GI tract in order to suppress the expression of cellular adhesion molecules in the gut.

When practiced, the methods of the invention can be by way of administering the compounds to a subject via any acceptable administration route using any acceptable form, as is described above, and allowing the body of the subject to distribute the compounds to the target cell through natural processes. As is described above, administering can likewise be by direct injection to a site (e.g., organ, tissue) containing a target cell (i.e., a cell to be treated).

Furthermore, administering can follow any number of regimens. It thus can comprise a single dose or dosing of experimental compound, or multiple doses or dosings over a period of time. Accordingly, treatment can comprise repeating the administering step one or more times until a desired result is achieved. In certain embodiments, treating can continue for extended periods of time, such as weeks, months, or years. Those of skill in the art are fully capable of easily developing suitable dosing regimens for individuals based on known parameters in the art. The dosage amounts for compounds of the invention may be used in the methods of these embodiments of the invention. For the treatment of IBD, GI tract inflammation or suppressing expression of cellular adhesion molecules in the gut, it is preferred that the compounds be administered at amounts of about 1 mg/day to 9,000 mg/day.

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation in the GI tract, which with IBD is often related to the amount of pain an individual is experiencing. With patients not currently experiencing IBD symptoms, the change one might look for may involve immune cell parameters such as TNFα expression on immune-cells or the percent of regulatory T-cells in the blood. Suitable amounts are disclosed herein, and additional suitable amounts can he identified by those of skill in the art without undue or excessive experimentation, based on the amounts disclosed herein.

In one aspect, the invention provides a method of treating or preventing a subject suffering from IBD, or otherwise healthy individuals, perhaps with a genetic predisposition for Crohn's Disease or ulcerative colitis, from developing IBD. The method may also involve treating those with a remissive form of IBD. According to the invention, the term "a subject suffering from IBD" is used to mean a subject (e.g., animal, human) having a disease or disorder showing one or more clinical signs that are typical of IBD. In general, the method of treating or preventing according to this aspect of the invention comprises administering to the subject an amount of compound therapy that is effective in treating or preventing one or more symptoms or clinical manifestations of IBD, or in preventing development of such symptom(s) or manifestation(s).

Thus, according to the methods of the invention, the invention can provide methods of treatment of IBD, inflammation associated with enteric infection and inflammation associated with autoimmune diseases. The methods of treatment can be prophylactic methods. In certain embodiments, the method is a method of treating IBD, inflammation associated with enteric infection and inflammation associated with autoimmune diseases. In other embodiments, the method is a method of preventing IBD. In embodiments, the method is a method of preventing a remissive form of IBD from becoming active. In still other embodiments, the method is a method of improving the health status of a subject suffering from IBD, inflammation associated with enteric infection and inflammation associated with autoimmune diseases. Organisms causing gastroenteric infections include but are not limited to: *Escherichia coli, Shigella, Salmonella,* pathogenic *Vibrios, Campylobacter jejuni, Yersina enterocolitica, Toxoplasma gondii, Entamoeba histolytica* and *Giardia lamblia.* Accordingly, in certain embodiments, the invention provides a method of protecting the health, organs, and/or tissues of a subject suffering from IBD, inflammation associated with enteric infection and inflammation associated with autoimmune diseases or at risk from developing IBD, inflammation associated with enteric infection and inflammation associated with autoimmune diseases.

In one embodiment of the invention, the method of treating IBD comprises treating IBD without causing discernable side-effects, such as significant weight gain, systemic immune suppression, cushingoid appearance, osteopenia/osteoporosis, or pancreatitis that is common of currently available IBD treatments (i.e. corticosteroids, tumor necrosis factor alpha inhibitors). That is, it has been found that the method of treating according to the present invention, which provides the treatment effect, at least in part, by affecting the expression and/or activation of LANCL2 in some cells, provides the beneficial effect without causing a significant gain in weight, for example by fluid retention, in the subject being treated, as compared to other similar subjects not receiving the treatment.

As such, the methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating the intestine. Another may be the increase in regulatory immune cell populations, such as CD4$^+$CD25$^+$FoxP3$^+$ regulatory T-cells, or an increase in regulatory properties of lymphocytes or macrophages (e.g. increased interleukin 4 (IL-4) or IL-10 or decreased TNF-$\alpha$ and IL-6). Another may be the decreased presence of inflammatory genes and/or adhesion molecules. The methods can thus also be considered methods of affecting or altering the immune response of a subject to whom the compound therapy is administered. The subject may have inflammatory bowel disease or another condition in which the immunomodulation of T cells or downregulation of cellular adhesion molecules is a desired outcome.

The invention also provides methods of treating an infectious disease with the compounds described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the familyhepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabiá virus; viruses in the family bunyaviridae such as Crimean-Congo hemorrhagic fever virus; viruses in the family filoviridae such as ebola virus and marburg virus; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracis, Bacillus cereus, Bordetella pertussis, Borrelia burgdorferi, Brucella abortus, Brucella canis, Brucella melitensis, Brucella suis Campylobacter jejuni Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis, Yersinia enterocolitica, Yersinia pseudotuberculosis,* and other species from the genera of the above-mentioned organisms.

Non-limiting examples of fungal infections include infection with fungi of the genus *Aspergillus,* such as *Aspergillus fumigatus,* which cause aspergillosis; fungi of the genus *Blastomyces,* such as *Blastomyces dermatitidis,* which cause blastomycosis; fungi of the genus *Candida,* such as *Candida albicans,* which cause candidiasis; fungi of the genus *Coccidioides,* which cause coccidioidomycosis (valley fever); fungi of the genus *Cryptococcus,* such as *Cryptococcus neoformans* and *Cryptococcus gattii,* which cause cryptococcosis; dermatophytes fungi, which cause ringworm; fungi that cause fungal keratitis, such as *Fusarium* species, *Aspergillus* species, and *Candida* species; fungi of the genus *Histoplasma,* such as *Histoplasma capsulatum,* which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause pneumocystis pneumonia; and fungi of the genus *Sporothrix*, such as *Sporothrix schenckii*, which cause sporotrichosis.

The invention also provides methods of treating an autoimmune inflammatory disease with the compounds described herein. Non-limiting examples of autoimmune inflammatory diseases include inflammatory bowel disease (IBD), systemic lupus, rheumatoid arthritis, type 1 diabetes, psoriasis, and multiple sclerosis, among others.

The invention also provides methods of treating chronic inflammatory diseases with the compounds described herein. Non-limiting examples of chronic inflammatory diseases includes metabolic syndrome, obesity, prediabetes, cardiovascular disease, and type 2 diabetes, among others.

The invention also provides methods of treating diabetes with the compounds described herein, including type 1 diabetes, type 2 diabetes, and other types of diabetes. The term "diabetes" or "diabetes mellitus" is used to encompass metabolic disorders in which a subject has high blood sugar (i.e., hyperglycemia). Hyperglycemic conditions have various etiologies, such as the pancreas does not produce enough insulin, or cells do not respond to the insulin that is produced. There are several recognized sub-types of diabetes. Type 1 diabetes is characterized by the complete failure of the body to produce insulin or the failure of the body to produce enough insulin. Type 2 diabetes generally results from insulin resistance, a condition in which cells fail to use insulin properly. Type 2 diabetes sometimes co-presents with an insulin deficiency. Gestational diabetes occurs when pregnant women without a previous diagnosis of diabetes develop hyperglycemia. Less common forms of diabetes include congenital diabetes (due to genetic defects relating to insulin secretion), cystic fibrosis-related diabetes, steroid diabetes induced by high doses of glucocorticoids, and several forms of monogenic diabetes (including maturity onset diabetes of the young). Monogenic diabetes encompasses several hereditary forms of diabetes caused by mutations in a single, autosomal dominant gene (as contrasted to more complex, polygenic etiologies resulting in hyperglycemia).

In view of the above methods, it should be evident that the present invention provides LANCL2-binding compound therapy for use in contacting cells, such as in treating cells of a subject. The above discussion focuses on the use of the compounds of the present invention as part of a composition for use in what could generally be considered a pharmaceutical or medical setting.

The compounds described in this invention for the treatment of IBD, GI tract inflammation, and other conditions described may be formulated as a pharmaceutical, nutritional composition, functional food composition, or dietary aid, as are described in greater detail above.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

MOLECULAR MODELING EXAMPLES

Example 1

Molecular Modeling of LANCL2 Ligand Binding

Introduction

Established LANCL2 agonists such as abscisic acid (ABA) and NSC61610 exert anti-inflammatory activity in a broad range of diseases models ranging from IBD to diabetes and influenza. The value of LANCL2 as a novel therapeutic target merits efforts to discover and develop a new class of orally active drugs for the treatment of chronic metabolic, immune-mediated, and infectious disease. As discussed in the present example, additional LANCL2 agonists were developed through rational drug design that iteratively combines computational modeling and experimental validation. The present example shows approaches to increase rational drug design and medicinal chemistry efforts to increase solubility, increase binding to LANCL2, lower cost, and understand the LANCL2 protein itself.

Methods

Structure of LANCL2. No crystal structure for LANCL2 exists. Therefore in order to understand the structure and function of LANCL2, homology modeling of human LANCL2 was performed using the crystal structure of LANCL1 as a template. Model quality was assessed and refinements were made through energy minimization procedures. Homology modeling predicts the 3D structure of a protein via identifying its homologous proteins from other members of the protein family whose structures have been solved experimentally [52]. When proteins have more than 35% sequence identity, they are likely to be homologous. LANCL1 shares 54% sequence identify with LANCL2 [15].

Compound generation and ligand structure. Structures of LANCL2 agonists were generated (FIGS. 1A and 1B). SMILES of these agonists were generated using the NIH's online SMILES Translator and Converter [53]. Concurrently, individual structural .pdb files were generated and downloaded. AutoDock Tools was using to convert pdb files into the .pdbqt necessary for virtual screening.

Virtual screening. The docking of the generated derivative files was performed with AutoDock Tools. A search space was defined, including grid box center and x, y, and z dimensions. The docking applied to the whole protein target, with a grid covering the whole protein surface. The grid was a regular cuboid (77.8 Å×77.8 Å×77.8 Å) with grid points separated by 0.608 Å. This grid was centered in the middle of the protein. These dimensions and spacing allowed the grid to cover the entire surface of LANCL2. The genetic algorithm was used in stochastic global optimization. One hundred bound conformations were generated by AutoDock Tools for each compound. The 100 resulting poses of each derivative were clustered with an RMSD cluster tolerance of 2.0 Å.

Analyzing virtual screening results. The search for the best way to fit each compound into LANCL2 using AutoDock Vina resulted in docking log files that contained records of docking, including binding energy of each predicted binding mode for all the compounds. Binding energies represent the sum of the total intermolecular energy, total internal energy and torsional free energy minus the energy of the unbound system. Compounds were ranked by the most negative energy value. The lowest binding energy pose in the first cluster was considered as the most favorable docking pose. A lower binding free energy indicates a more stable protein-ligand system and a higher affinity between protein and ligand. Exemplary compounds are further validated by in vitro testing and pre-clinical studies using mouse models of human diseases.

Results

NSC61610 docking summary. A histogram of NSC61610's top five clusters with the energy of the lowest energy position is given in FIG. 2. NSC61610 has very high affinity for the 'central cleft.' The top two clusters, representing 7% of total runs, each direct to this site. Due to the two angstrom tolerance, it is likely other clusters direct to this site. The next two clusters direct to an 'allosteric site' near the blue random coil.

Figure 3:
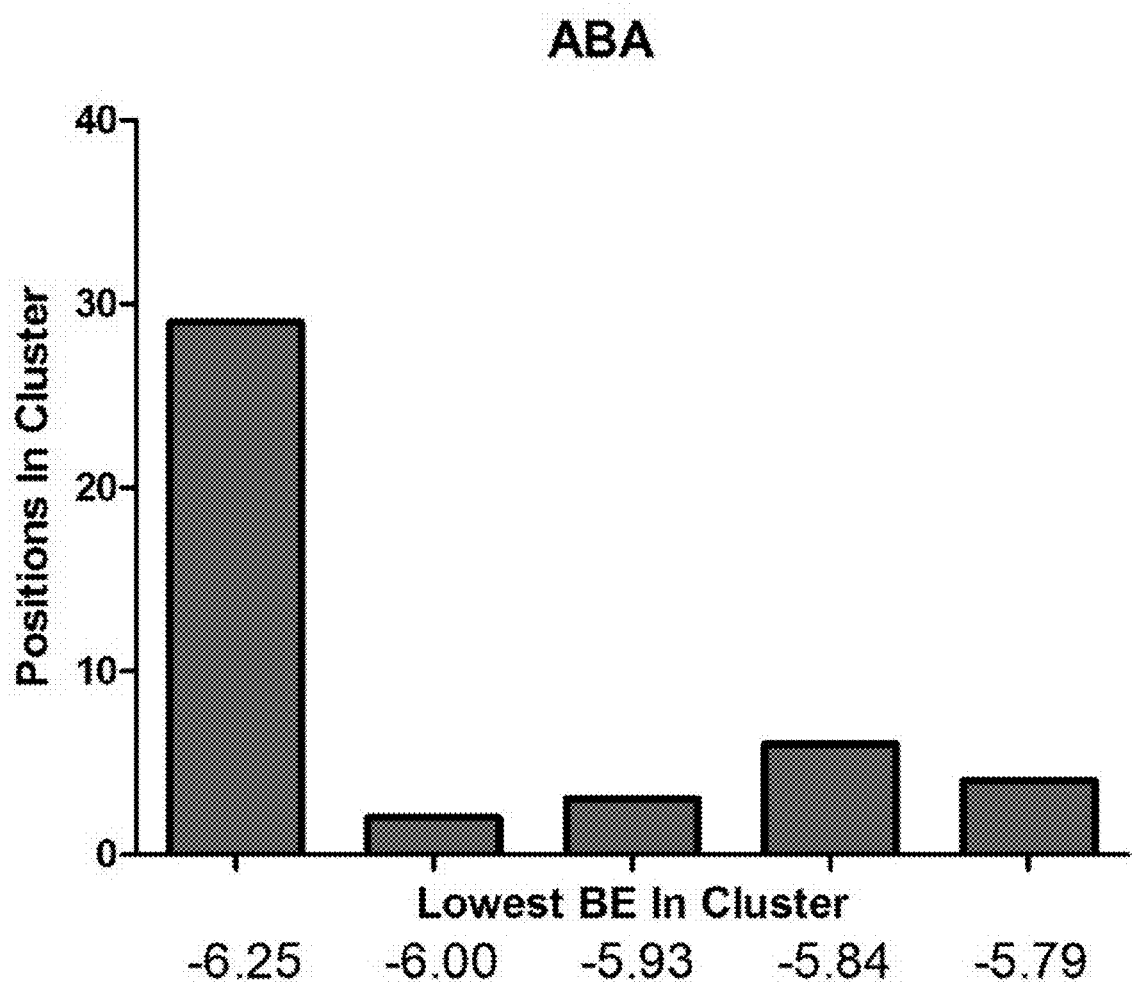
FIG. 3. Clustering histogram for the top five clusters of ABA. One hundred docking runs were performed with ABA docked to LANCL2 using AutoDock Tools. The RMSD cluster tolerance was 2 Å. Binding energies are listed in kJ/mol.

ABA docking summary. A histogram of ABA's top five clusters with the energy of the lowest energy position is given in FIG. 3. ABA has moderate affinity but very high specificity for the 'allosteric' site between the light green helix and light green random coil. 29% of runs directed to this top cluster. The second cluster also directed to this site. Due to the two angstrom tolerance, it is likely other cluster direct to this site. The fourth cluster appears to be in the 'central cleft.' This leaves open the question of the true therapeutic site of ABA.

Figure 4:
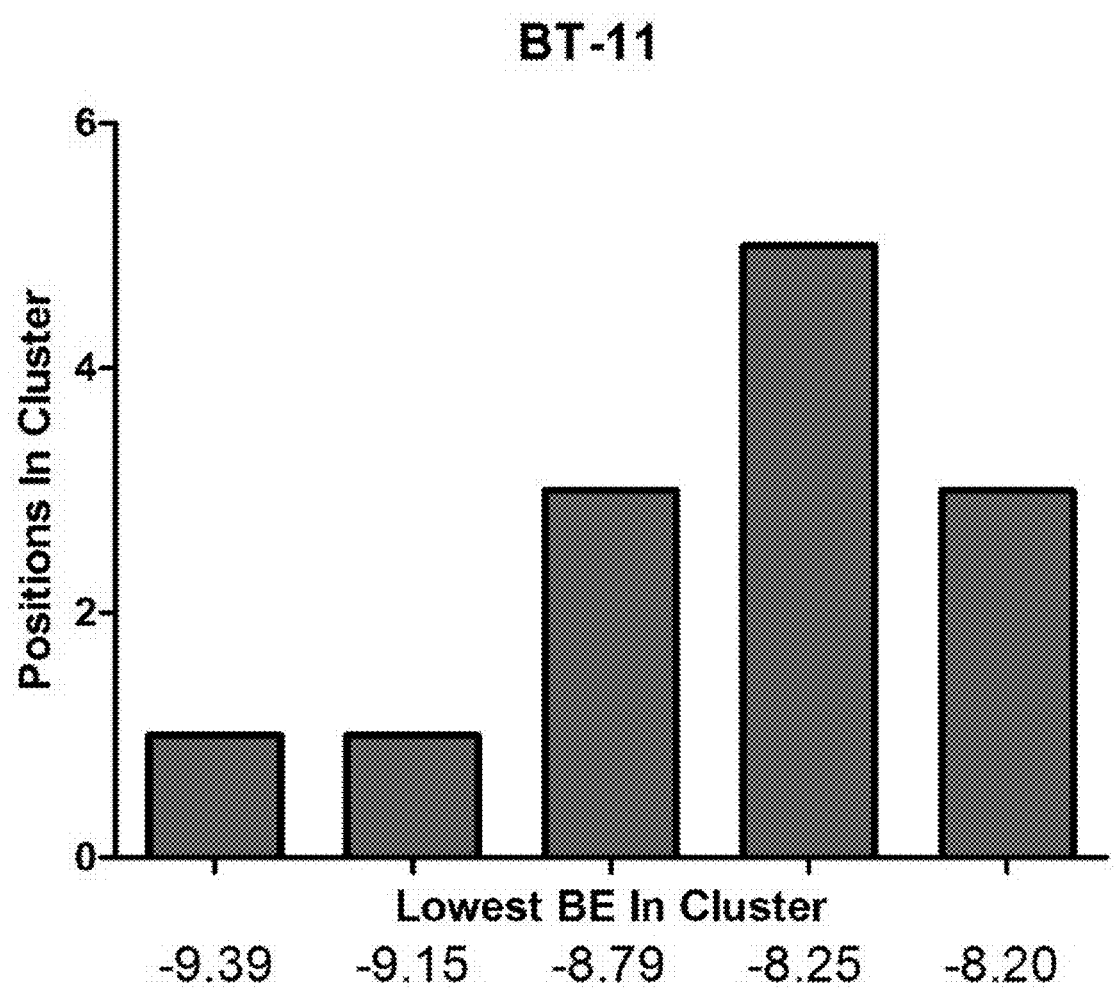
FIG. 4. Clustering histogram for the top five clusters of BT-11. One hundred docking runs were performed with BT-11 docked to LANCL2 using AutoDock Tools. The RMSD cluster tolerance was 2 Å. Binding energies are listed in kJ/mol.

BT-11 docking summary. A histogram of BT-11's top five clusters with the energy of the lowest energy position is given in FIG. 4. BT-11's top two clusters direct to the 'central cleft' but represent only 2% of runs. However, due to the two angstrom tolerance, it is likely other clusters direct to this site. BT-11 has slightly less affinity for this site than NSC61610 but more than ABA. BT-11 has demonstrated therapeutic efficacy (see examples below).

Figure 5:
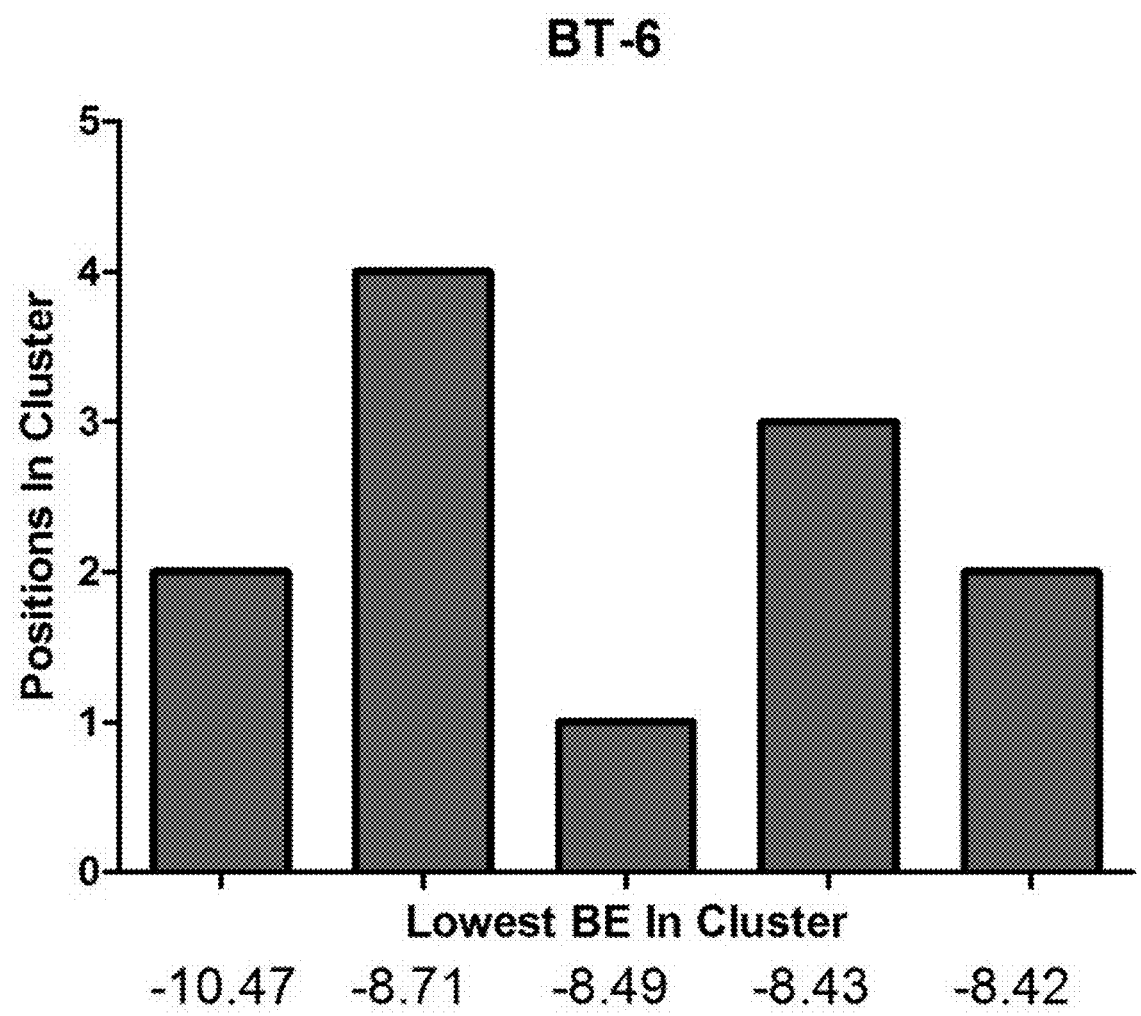
FIG. 5. Clustering histogram for the top five clusters of BT-6. One hundred docking runs were performed with BT-6 docked to LANCL2 using AutoDock Tools. The RMSD cluster tolerance was 2 Å. Binding energies are listed in kJ/mol.

BT-6 docking summary. A histogram of BT-6's top five clusters with the energy of the lowest energy position is given in FIG. 5. BT-6 has the highest affinity of any compound docked. The top two, perhaps three, clusters direct to the 'central cleft.' Due to the two angstrom tolerance, it is likely other clusters direct to this site. Cluster 4 directs to the 'allosteric' site along the blue random coil.

Figure 6:
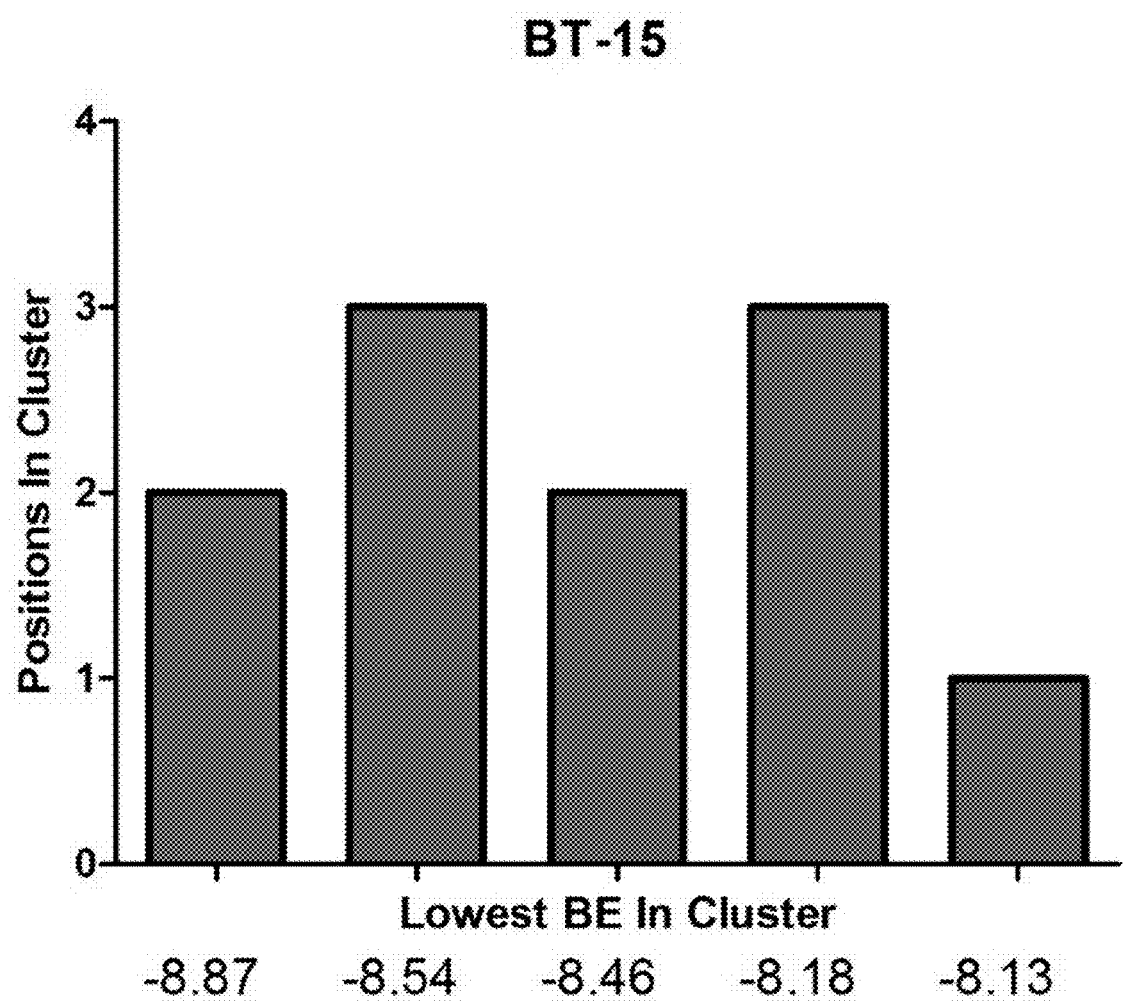
FIG. 6. Clustering histogram for the top five clusters of BT-15. One hundred docking runs were performed with BT-15 docked to LANCL2 using AutoDock Tools. The RMSD cluster tolerance was 2 Å. Binding energies are listed in kJ/mol.

BT-15 docking summary. A histogram of BT-15's top five clusters with the energy of the lowest energy position is given in FIG. 6. BT-15 does not have the binding affinity of either NSC61610 or BT-11. While it does appear to direct toward the 'central cleft,' this effect does not appear to be as pronounced as NSC61610 or BT-11.

Figure 7:
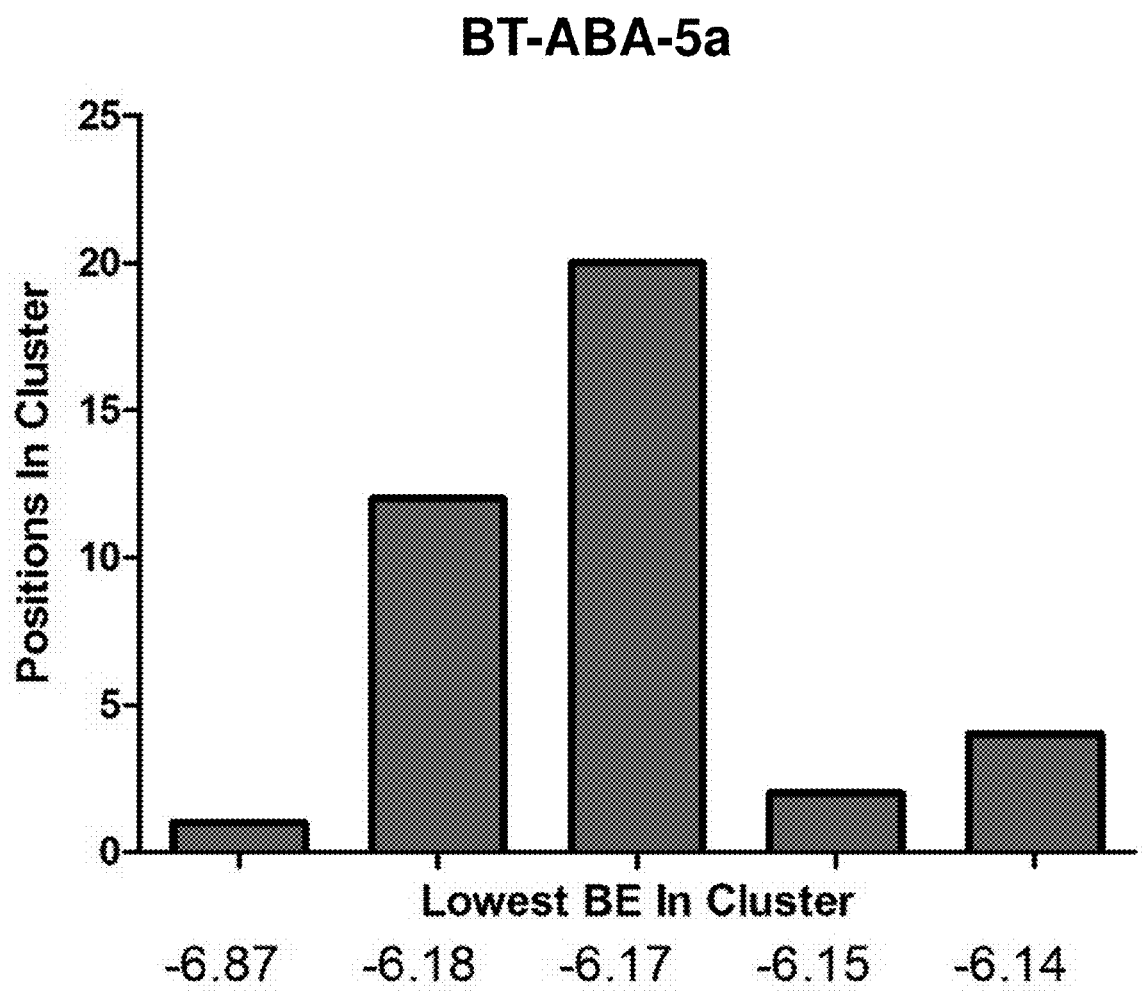
FIG. 7. Clustering histogram for the top five clusters of BT-ABA-5a. One hundred docking runs were performed with BT-ABA-5a docked to LANCL2 using AutoDock Tools. The RMSD cluster tolerance was 2 Å. Binding energies are listed in kJ/mol.

BT-ABA-5a docking summary. A histogram of BT-ABA-5a's top five clusters with the energy of the lowest energy position is given in FIG. 7. BT-ABA-5a's highest affinity is in a spot not seen in any previous docking examined. However, clusters 2 and 3 represent the vast majority of runs, at 32%. Cluster 2 directs to an allosteric site in the back right. Cluster 3 directs to the 'allosteric' site of ABA. Cluster 4 also directs to this site. Due to the two angstrom tolerance, it is likely other clusters direct to this site.

Discussion

Both ABA and NSC61610 exert LANCL2-dependent immune-modulatory, anti-inflammatory, and anti-diabetic effects, however computational predictions suggest that they bind at different sites of LANCL2. As expected, the rationally designed ligands direct primarily to the primary binding sites of ABA and NSC61610. The BT-ABA compounds are smaller in size and have —COOH functional groups; it makes intuitive sense they would direct toward a hydrophilic surface pocket. The BT compounds are much more hydrophobic; therefore it makes intuitive sense they would direct to the more hydrophobic central cleft surrounded by alpha-helices.

The binding affinities have a moderate correlation with SPR data (FIGS. 1A and 1B; see examples below). SPR data (with $K_D$ value) suggests an order of binding strength of NSC61610 (2.3 & 6.3), BT-11 (6.3 & 7.7), BT-15 (11.4 & 21.4), BT-6 (18.2). Modeling data (with lowest BE) suggests an order of binding strength of BT-6 (−10.47), NSC61610 (−10.27), BT-11 (−9.39), BT-15 (−8.87). Besides the flip in BT-6 from worst to first, SPR data and modeling data suggest the same order of binding strength. Molecular modeling data combined with rational drug design is likely to yield better understanding of the LANCL2 protein which will allow for further development of analogs that target and activate the LANCL2 pathway to exploit its potent anti-diabetic and anti-inflammatory properties.

MEDICINAL CHEMISTRY EXAMPLES

Example 2

BT-11 and Salt

As shown in Scheme 2-1, A solution of 6-(1H-Benzimidazol-2-yl)pyridine-2-carboxylic acid (12 g) in DMF (100 mL) was cooled to 0° C., and then sequentially added EDC.HCl (1.5 eq), HOBt (1.5 eq) and DIPEA (1.2 eq, taken in volumes with density presumed). The mixture was stirred for 10 min at 0° C. Piperazine (0.5 eq) was added and the reaction mixture was allowed to warm to RT gradually and stirred for 16 h. After completion of the reaction (monitored by TLC, eluent: 10% MeOH in DCM), the reaction mixture was poured into ice-cold water (~300 mL), the precipitated solid was filtered, washed with ice-cold water and dried to get BT-11 (10 g, 75%) as pale brown solid. $^1$H NMR (400 MHz, DMSO-$d_6$), δ 13.0 (s, 1H), 12.8 (s, 1H), 8.38 (dd, 2H), 8.13 (dt, 2H), 7.73 (dd, 2H), 7.67 (d, 2H), 7.57 (dd, 2H), 7.25 (m, 4H), 3.90 (bs, 2H), 3.80 (bdd, 2H), 3.65 (bdd, 2H), 3.56 (bs, 2H). LCMS-ES 529.44 [M+H]$^+$, 265.46 [(M+2H)/2]$^{++}$.

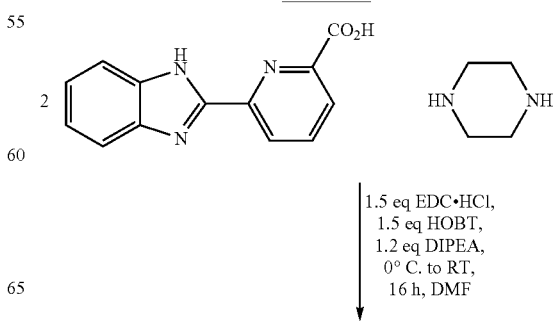

Scheme 2-1

-continued

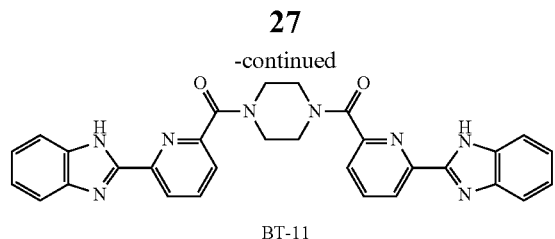

BT-11

As shown in Scheme 2-2, a suspension of BT-11 (1.0 eq) in minimal amount of MeOH (5 mL) was cooled to 0° C., was added 4 M methanolic HCl (excess, 15 mL/1g) dropwise over a period of 15-20 min. The mixture was allowed gradually to warm to RT for 3 h. After completion of the reaction (monitored by TLC, eluent: 10% MeOH in $CH_2Cl_2$), the volatiles were evaporated under reduced pressure. The crude material was washed with 10% MeOH in $CH_2Cl_2$ and lyophilized to get an off-white solid (850 mg, 75%). $^1$H NMR (400 MHz, DMSO-$d_6$), δ 8.58 (dd, 2H), 8.29 (dt, 2H), 7.83 (m, 6H), 7.44 (bd, 4H), 3.91 (bs, 2H), 3.81 (bm, 2H), 3.64 (bm, 2H), 3.55 (bs, 2H). LCMS-ES 529.56 [M+H]$^+$.

Scheme 2-2

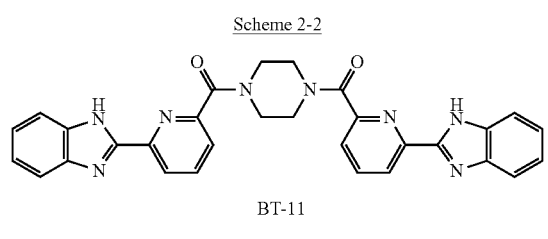

BT-11

↓ 4M HCl in MeOH,
0° C. to RT, 3 h,

BT-11 salt

Example 3

BT-12

As shown in Scheme 3-1, a solution of 6-(benzoxazol-2-yl)pyridine-2-carboxylic acid (4.05 g) in 10% DMF in $CH_2Cl_2$ was treated with EDC.HCl (1.5 eq), HOBt (1.5 eq) and DIPEA (1.2 eq, taken in volumes with density presumed) and 0.5 eq. of piperazine at 0° C. The mixture was allowed to warm to RT for 16 h. A light brown solid formed and was filtered in a sinter-glass funnel, washed with water, and lyophilized to give a light brown solid (3.2 g). $^1$H NMR (300 MHz, CDCl$_3$), δ 8.45 (dd, 2H), 8.05 (m, 2H), 7.9 (d, 2H), 7.8 (dd, 2H), 7.6 (dd, 2H), 7.4 (m, 2H), 7.35 (m, 2H), 4.0 (bm, 8H).

Scheme 3-1

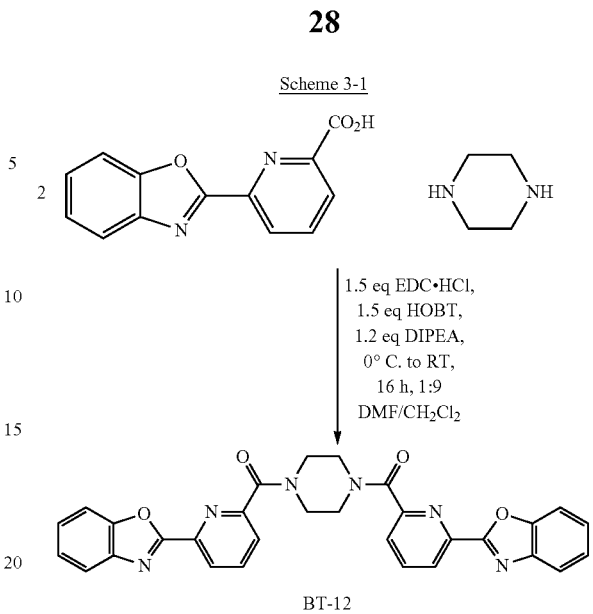

BT-12

Example 4

BT-14 and Salt

As shown in Scheme 4-1, a solution of 6-(benzoxazol-2-yl)pyridine-2-carboxylic acid (500 mg) of in DMF (10 mL) was treated with EDC.HCl (1.5 eq), HOBt (1.5 eq), DIPEA (3 eq), and tert-butyl piperazine-1-carboxylate (1.1 eq) at 0° C. The mixture was allowed to warm to RT for 16 h. After evaporation of the solvent, the residue was extracted into EtOAc and washed with water. The organic layer was evaporated under vacuum, crude residue washed with pentane gave light brown solid (120 mg, 48%). $^1$H NMR (400 MHz, DMSO-$d_6$), δ 8.4 (d, 1H), 8.2 (t, 1H), 7.9 (t, 2H), 7.8 (d, 1H), 7.5 (dt, 2H), 3.7 (bm, 2H), 3.5 (bm, 4H), 3.4 (bm, 2H), 1.4 (s, 9H). LCMS-ES 409.49 [M+H]$^+$, 431.37 [M+Na]$^+$, 447.36 [M+K]$^+$.

Scheme 4-1

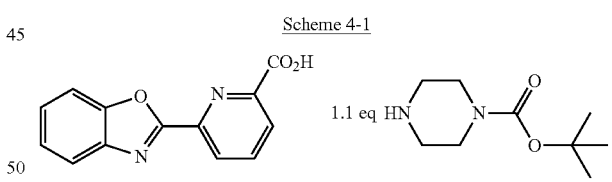

↓ 1.5 eq EDC•HCl,
1.5 eq HOBT,
3.0 eq DIPEA,
0° C. to RT,
16 h, DMF

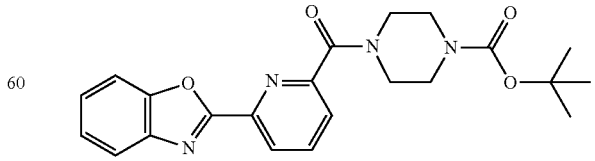

As shown in Scheme 4-2, the resulting compound from Scheme 4-1 (200 mg) was treated with methanolic HCl (6 mL) at 0° C. The mixture was allowed to warm to RT for 3 h. Evaporation of the solvent and washings with pentane and ether gave of a light brown solid (160 mg, quant.). $^1$H NMR (300 MHz, DMSO-d$_6$), δ 9.30 (bs, 2H), 8.45 (d, 1H), 8.25 (t, 1H), 7.9 (m, 3H), 7.5 (quin, 2H), 3.7 (bm, 2H), 3.5 (bm, 2H), 3.3 (bm, 4H), 1.4 (s, 9H). LCMS-ES 309.26 [M+H]$^+$.

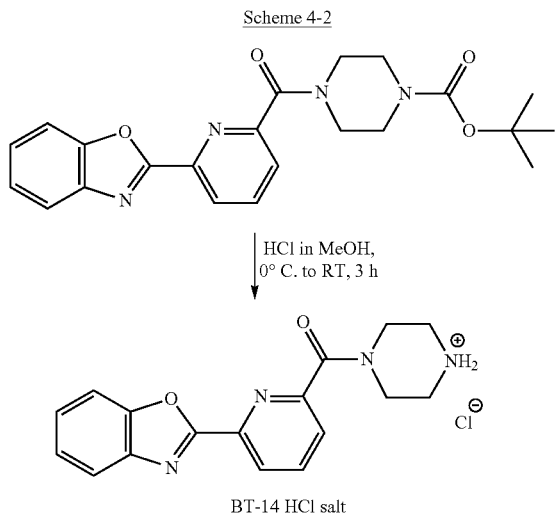

Scheme 4-2

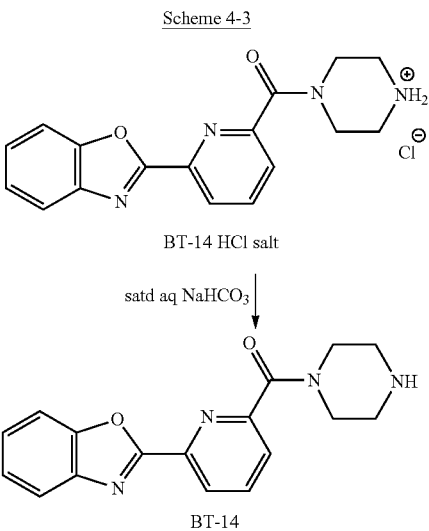

Scheme 4-3

As shown in Scheme 4-3, the resulting salt (25 mg) from Scheme 4-2 was neutralized with satd. Aq. NaHCO$_3$ followed by diving in lyophilizer to give 20 mg/96% of BT-14 in hand. The yield was 90%. $^1$H NMR (300 MHz, DMSO-d$_6$), δ 8.4 (d, 1H), 8.2 (t, 1H), 7.90 (t, 2H), 7.75 (d, 1H), 7.5 (quin, 2H), 3.95 (bm, 2H), 3.8 (bm, 2H), 3.3 (bm, 2H), 3.2 (bm, 2H); 309.37 LCMS-ES [M+H]$^+$.

Example 5

BT-15

As shown in Scheme 5-1, 6-(1H-Benzimidazol-2-yl)pyridine-2-carboxylic (50 mg) in DMF (5 mL) was treated with EDC.HCl (1.5 eq), HOBt (1.5 eq), DIPEA (3 eq), and 0.9 eq. of BT-14 HCl salt at 0° C. The mixture was allowed to warm to RT for 16 h. Filtering over sintered funnel followed by water wash and lyophilizing for moisture removal gave 20 mg of BT-15. $^1$H-NMR (400 MHz, DMSO-d$^6$), δ 12.93 (d, 1H), 8.44 (dd, 1H), 8.36 (t, 1H) 8.25 (t, 1H), 8.17 (m, 2H), 7.87 (m, 3H), 7.72 (m, 2H), 7.54 (m, 2H), 7.31 (m, 3H), 3.90 (s, 2H), 3.82 (bm, 2H), 3.67 (bm, 2H), 3.58 (bm, 2H). LCMS-ES 530.48 [M+H]$^+$, 265.94 [(M+2H)/2]$^{++}$.

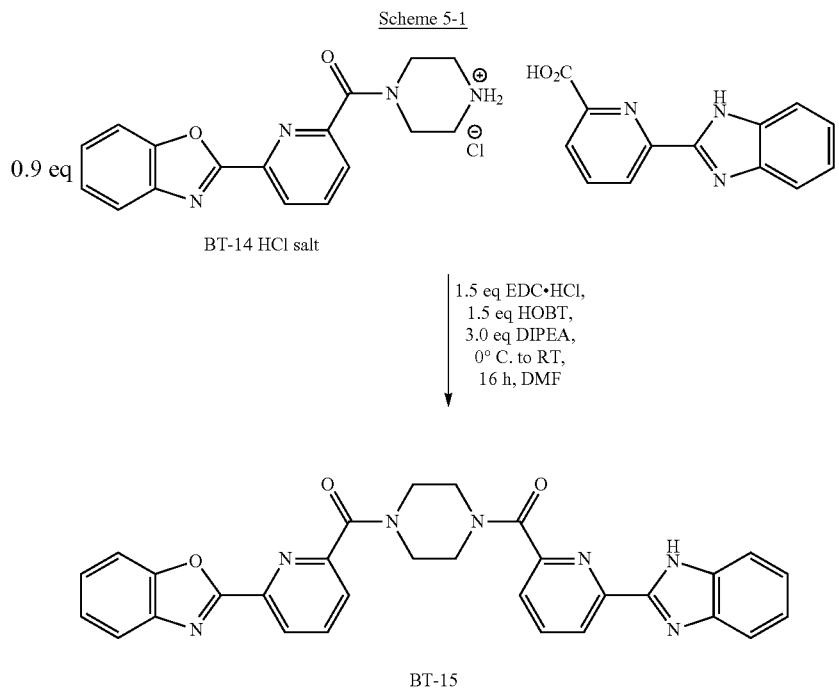 [SMILES: O=C(c1cccc(-c2nc3ccccc3o2)n1)N1CC[NH2+]CC1 ; [Cl-] ; O=C(O)c1cccc(-c2nc3ccccc3[nH]2)n1 ; O=C(c1cccc(-c2nc3ccccc3[nH]2)n1)N1CCN(C(=O)c2cccc(-c3nc4ccccc4o3)n2)CC1 ; "BT-15"]

BT-15 has shown LANCL2 binding (FIG. 1A). Its predictive binding affinity to LANCL2 is −9.9 and the affinity confined by SPR has a Kd value of 21.4.

Example 6

BT-13 Salt

As shown in Scheme 6-1, 6-(1H-Benzimidazol-2-yl)pyridine-2-carboxylic (500 mg) in DMF (10 mL) was treated with EDC.HCl (1.5 eq), HOBt (1.5 eq), DIPEA (3 eq), and tert-butylpiperazine-1-carboxylate (1.1 eq) at 0° C. The mixture was allowed to warm to RT for 16 h. After pouring the reaction mixture into ice-cold water, the precipitate was filtered and dried to give a pale brown solid (600 mg, 70%). TLC (100% ethyl acetate). HNMR & LCMS complies. (Yield: 70%). $^1$H NMR (300 MHz, DMSO-$d_6$), δ 12.90 (s, 1H), 8.4 (d, 1H), 8.15 (t, 1H), 7.65 (td, 3H), 7.25 (quin, 2H), 3.7 (bm, 2H), 3.5 (bm, 2H), 3.3 (bm, 4H), 1.4 (s, 9H). LCMS-ES 408.35 [M+H]$^+$.

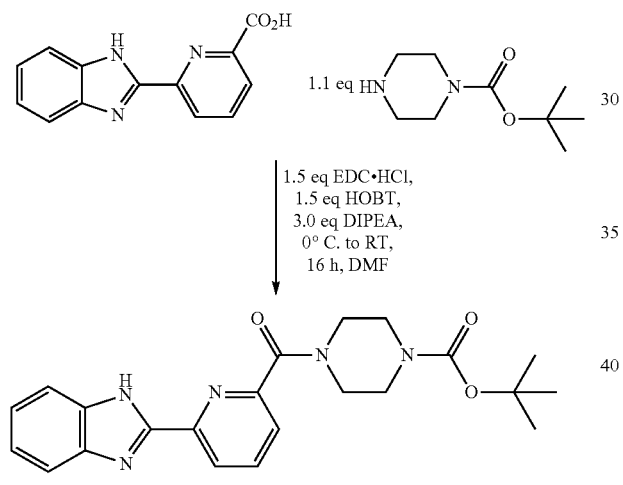

Scheme 6-1

As shown in Scheme 6-2, the resulting compound from Scheme 6-1 (600 mg) was treated with methanolic HCl (6 mL) for 3 h at 0° C. The mixture was allowed to gradually warm to RT for 3 hours. Evaporation of the excess methanolic HCl gave BT-13 HCl (500 mg) as a light brown solid.

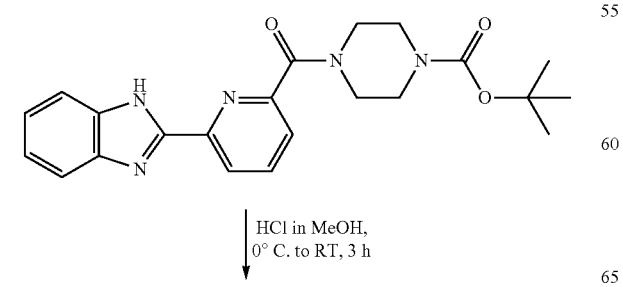

Scheme 6-2

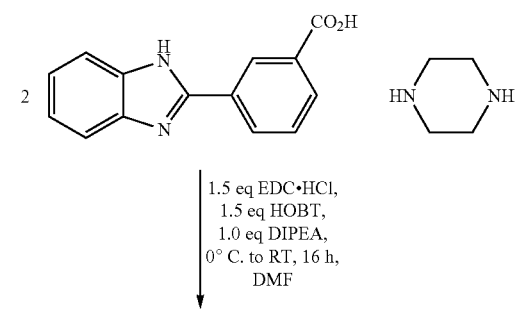

BT-13 HCl salt

Example 7

BT-4 and Salt

As shown in Scheme 7-1, 3-(1H-Benzimidazol-2-yl)benzoic acid (100 mg) in DMF (6 mL) was treated with EDC.HCl (1.5 eq), HOBt (1.5 eq), DIPEA (1 eq), and 0.5 eq. of piperazine at 0° C. The mixture was allowed to warm to RT for 16 h. TLC (10% methanol:DCM) shows formation of non-polar spot and absence of starting material. After workup and washings with ether 30 mg/95% of BT-4 was isolated. $^1$H NMR (400 MHz, DMSO-$d_6$), δ 13.0 (s, 2H), 8.3 (bm, 4H), 7.75 (bm, 4H), 7.60 (bm, 4H), 7.2 (bm, 4H), 3.65 (bm, 8H). LCMS-ES 527.36 [M+H]$^+$, 264.50 [(M+2H)/2]$^{++}$.

Scheme 7-1

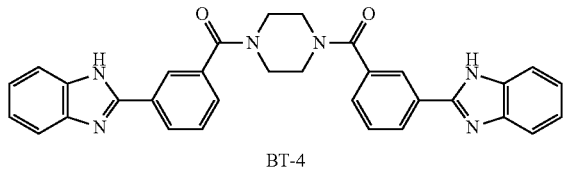

BT-4

As shown in Scheme 7-2, 30 mg/95% of BT-4 was treated with 4 M HCl in dioxane for 3 h. Evaporation of the solvent and washing with ether gave 10 mg/97% of BT-4 HCl salt. $^1$H NMR (400 MHz, DMSO-$d_6$), δ 8.45 (bm, 4H), 7.80 (bm, 8H), 7.50 (bm, 4H), 3.65 (bm, 8H). LCMS-ES 527.44 [M+H]$^+$, 264.50 [(M+2H)/2]$^{++}$.

Scheme 7-2

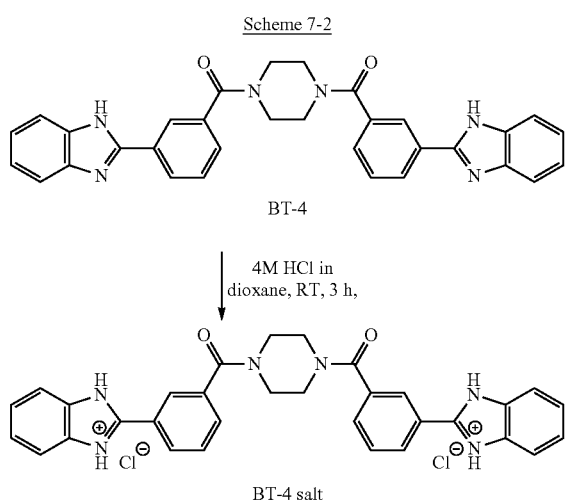

BT-4

4M HCl in dioxane, RT, 3 h,

BT-4 salt

Example 8

BT-6 and Salt

As shown in Scheme 8-1, 3-(1H-Benzimidazol-2-yl)benzoic acid (100 mg) in DMF (6 mL) was treated with EDC·HCl (1.5 eq), HOBt (1.5 eq), DIPEA (1 eq), and benzene-1,4-diamine (0.5 eq) at 0° C. The mixture was allowed to warm to RT for 16 h. TLC (10% methanol:DCM) shows formation of non-polar spot and absence of starting material. After workup and washings with ether, a light brown solid (60 mg) was isolated. $^1$H NMR (300 MHz, DMSO-d$_6$), δ 13.1 (s, 2H), 10.45 (s, 2H), 8.75 (s, 2H), 8.40 (d, 2H), 8.05 (d, 2H), 7.85 (s, 4H), 7.70 (t, 4H), 7.55 (d, 2H) 7.25 (quin, 4H). LCMS-ES 549.0 [M+H]$^+$ 275.1 [(M+2H)/2]$^{++}$.

Scheme 8-1

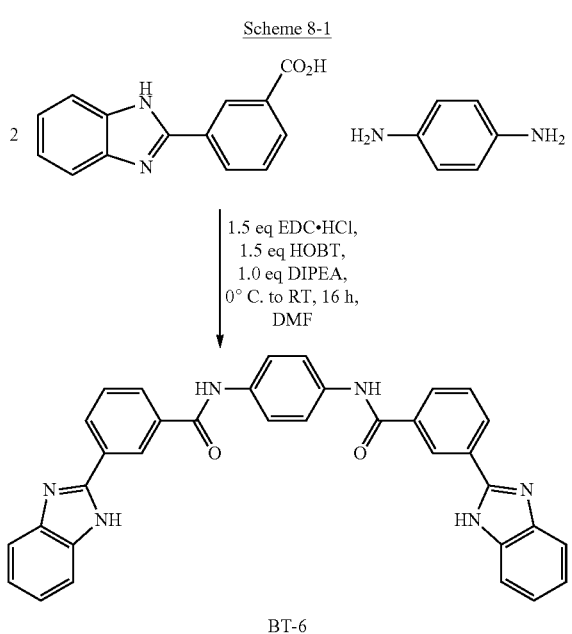

BT-6

As shown in Scheme 8-2, 60 mg/98% of BT-6 was treated with 4 M HCl in dioxane for 3 h. After evaporation of the solvent and washed with ether gave 50 mg/96% of BT-6 HCl salt. $^1$H NMR (300 MHz, DMSO-d$_6$), δ 10.60 (s, 2H), 9.00 (s, 2H), 8.55 (d, 2H), 8.30 (d, 2H), 7.90 (s, 4H), 7.85 m, 6H), 7.50 (m, 4H). LCMS-ES 549.3 [M+H]$^+$ 275.3 [(M+2H)/2]$^{++}$.

Scheme 8-2

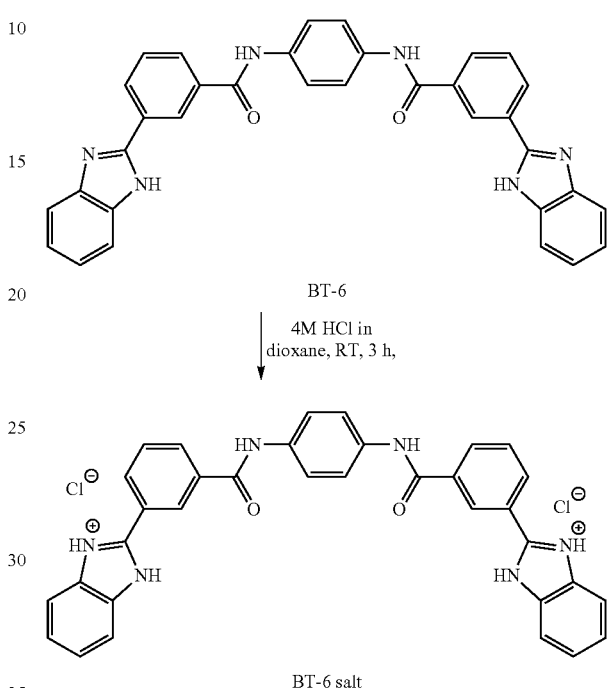

BT-6

4M HCl in dioxane, RT, 3 h,

BT-6 salt

Example 9

BT-16 and Salt

As shown in Scheme 9-1, 6-(1H-Benzimidazol-2-yl)pyridine-2-carboxylic (100 mg) in DMF (10 mL) was treated with EDC·HCl (1.5 eq), HOBt (1.5 eq), DIPEA (3 eq), and benzene-1,4-diamine (0.5 eq) at 0° C. The mixture was allowed to warm to RT for 16 h. After pouring the reaction mixture into ice-cold water, the precipitate was filtered and dried to give a pale brown solid (60 mg).

Scheme 9-1

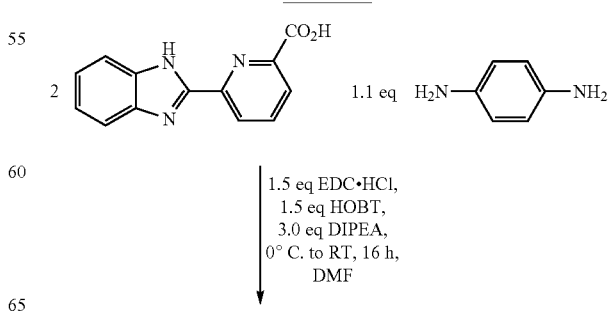

1.5 eq EDC·HCl,
1.5 eq HOBT,
3.0 eq DIPEA,
0° C. to RT, 16 h,
DMF

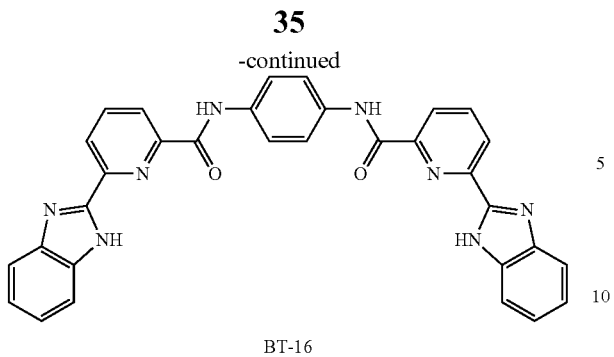

BT-16

As shown in Scheme 9-2, compound BT-16 (50 mg) was treated with HCl in dioxane (3 mL) at 0° C. The mixture was allowed to warm to RT for 4. Evaporation of the excess dioxane HCl gave 30 mg of a brown solid (30 mg). $^1$H NMR (300 MHz, DMSO-$d_6$), δ 11.00 (s, 2H), 8.6 (bm, 2H), 8.35 (bm, 4H), 8.05 (s, 4H), 7.85 (bm, 4H), 7.40 (bm, 4H). LCMS-ES 551.84 [M+H]$^+$.

Scheme 9-2

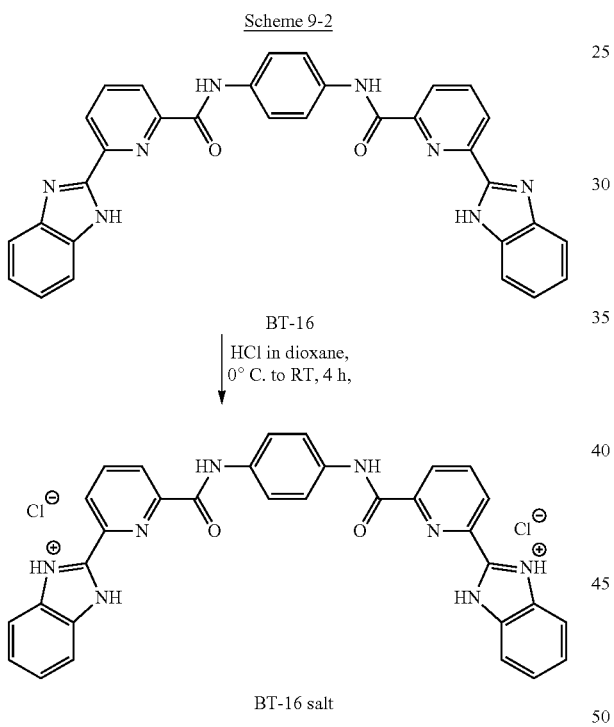

Example 10

BT-3 and Salt

As shown in Scheme 10-1, 3-(2-Benzoxazolyl)benzoic acid (50 mg) in DMF (10 mL) was treated with EDC.HCl (1.25 eq), HOBt (1.25 eq), DIPEA (1 eq), and piperazine (1 eq) at 0° C. The mixture was allowed to warm to RT for 16 h. After diluting the reaction mixture with ice cold water, resulting solid thrown out, filtration, followed by drying gave 30 mg of BT-3. $^1$H NMR (300 MHz, DMSO-$d_6$), δ 8.2 (bm, 4H), 7.8 (bm, 4H), 7.7 (bm, 4H), 7.45 (bm, 4H), 3.6 (bm, 8H). LCMS-ES 529.32 [M+H]$^+$.

Scheme 9-1

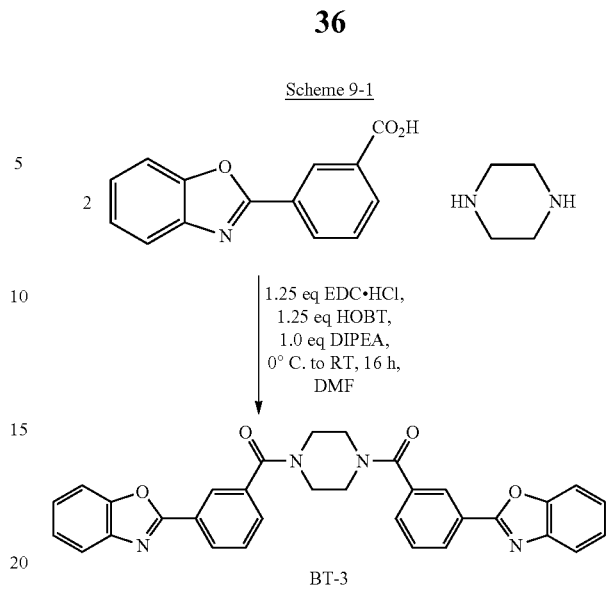

As shown in Scheme 10-2, BT-3 (30 mg) was treated in methanolic HCl (5 L) at 0° C. The mixture was allowed to warm to RT for 4 h. After evaporation of the excess methanolic HCl at vacuum, a brown solid (15 mg) formed.

Scheme 10-2

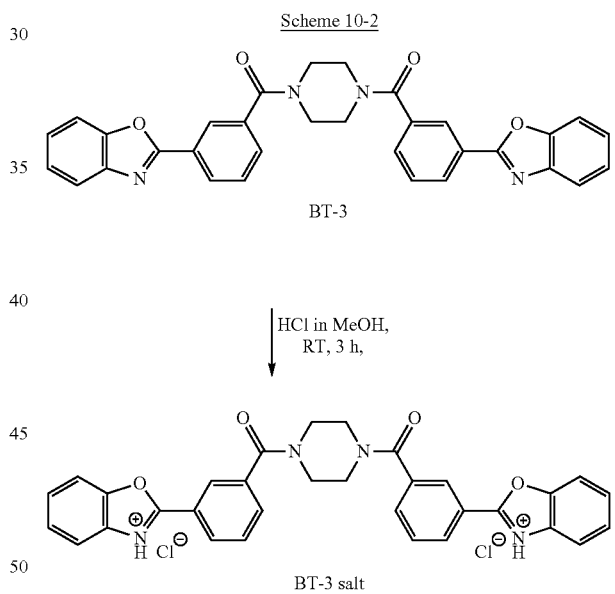

Example 11

BT-5 and Salt

As shown in Scheme 11-1, 3-(2-benzoxazolyl)benzoic acid (50 mg) in DMF (10 mL) was treated with EDC.HCl (1.25 eq), HOBt (1.25 eq), DIPEA (1 eq), and benzene-1, 4-diamine (0.5 eq) at 0° C. The mixture was allowed to warm to RT for 16 h. Diluting the reaction mixture with ice cold water, throwing out solids, filtering, followed by drying gave a light brown solid (30 mg). $^1$H NMR (300 MHz, TFA), δ 9.2 (bs, 2H), 8.8 (bm, 2H), 8.6 (bm, 2H), 7.9 (bm, 14H).

Scheme 11-1

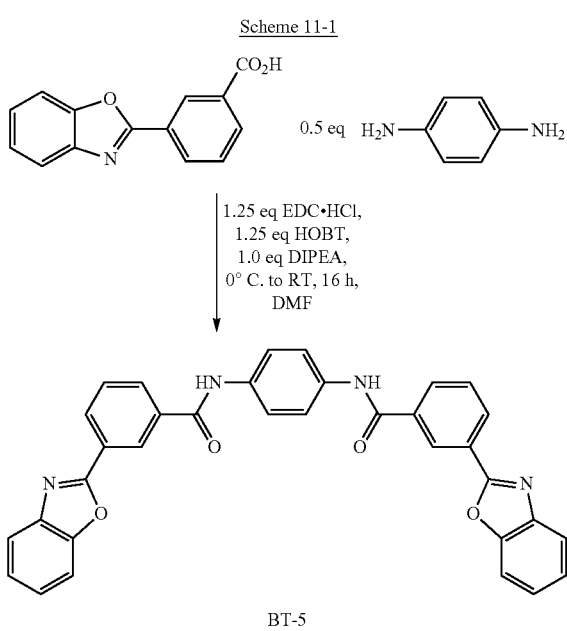

BT-5

As shown in Scheme 11-2, 35 mg of BT-5 was treated in HCl dioxane (5 mL) at 0° C. The mixture was allowed to warm to RT for 4 h. After evaporation of the excess dioxane at vacuum, a light brown solid (15 mg) formed. ¹H NMR (300 MHz, TFA), δ 9.3 (bs, 2H), 8.8 (bm, 2H), 8.6 (bm, 2H), 7.9 (bm, 14H).

Scheme 11-2

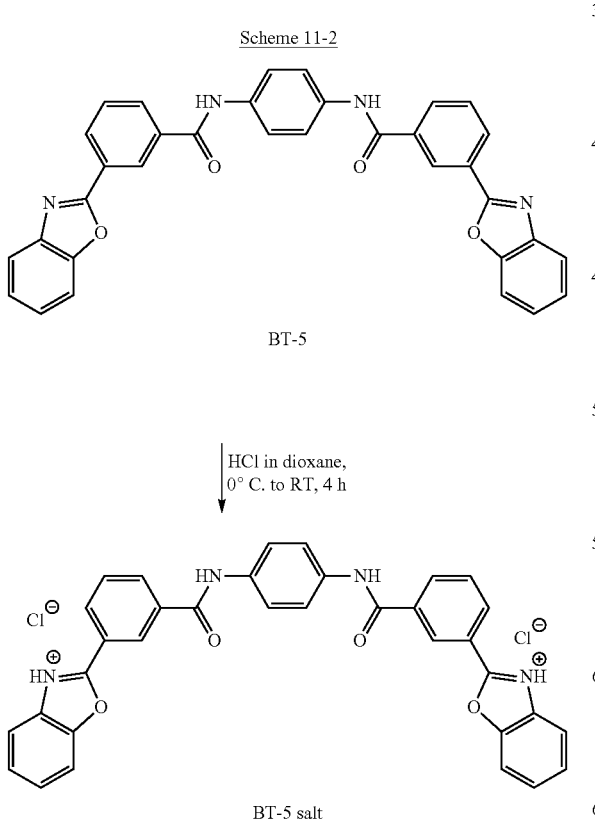

BT-5 salt

Example 12

BT-17 and Salt

As shown in Scheme 12-1, 6-(Benzoxazol-2-yl)pyridine-2-carboxylic acid (100 mg) in DMF (10 mL) was treated with EDC.HCl (1.5 eq), HOBt (1.5 eq), DIPEA (1.2 eq), and benzene-1,4-diamine (0.5 eq) at 0° C. The mixture was allowed to warm to RT for 16 h. Diluting the reaction mixture with ice cold water, throwing out solids, filtering, followed by drying gave a light brown solid (70 mg). ¹H NMR (400 MHz, TFA), δ 8.85 (dd, 4H), 8.55 (t, 2H), 8.1 (bm, 4H), 7.95 (m, 4H), 7.85 (s, 4H). LCMS-ES 553.28 [M+H]⁺.

Scheme 12-1

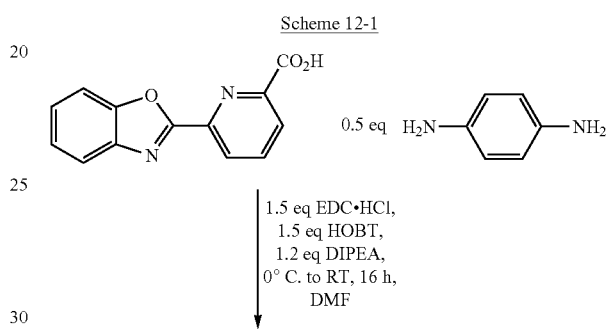

BT-17

As shown in Scheme 1.2-2, BT-17 (60 mg) was treated in dioxane HCl (10 ML) at 0° C. to RT for 4 h. After evaporation of the solvent by using a lyophiliser, a light brown solid (45 mg) formed. ¹H NMR (400 MHz, TFA), δ 8.90 (bm, 4H), 8.6 (bm, 2H), 8.0 (bm, 10H).

Scheme 12-2

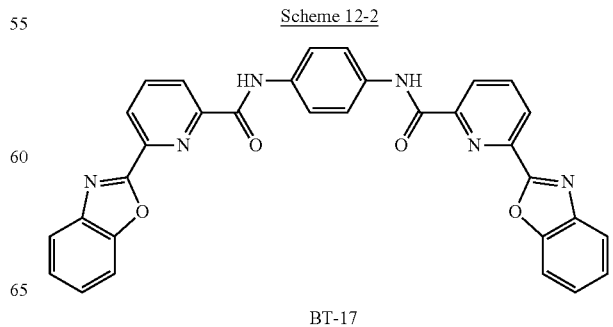

BT-17

-continued

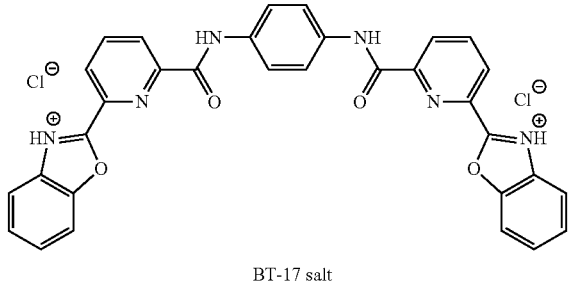

BT-17 salt

Example 13

BT-ABA-25

The structure of BT-ABA-25 is shown in Scheme 13-1. BT-ABA-25 is a ligand of LANCL2 (FIG. 1B). Its predictive binding affinity to LANCL2 is −7.5 and the affinity confirmed by SPR has a Kd value of 1.77e-04.

Scheme 13-1

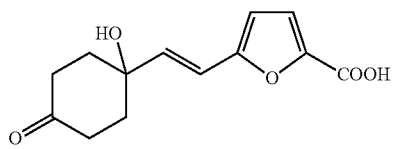

Example 14

BT-ABA-5a

As shown in Scheme 14-1, a solution of 8-vinyl-1,4-dioxaspiro[4.5]decan-8-ol (200 mg, 1 eq) and methyl 5-bromofuran-2-carboxylate (1.5 eq) in Et3N (2 mL) was degassed with argon for 10 min. Then, Pd(OAc)2 (0.025 eq), DPPF (0.05 eq) were added and again degassed for 10 min. The resulting reaction mixture was heated at 100° C. for 16 h. A light brown solid (130 mg) was isolated by column chromatography (EtOAx/Hexane 3:7). $^1$H NMR (400 MHz, DMSO-d$_6$), δ 7.30 (d 1H), 6.60 (d 1H), 6.45 (dd, 2H), 4.75 (s, 1H), 3.85 (s, 4H), 3.80 (s, 3H), 1.85 (m, 2H), 1.65 (m, 2H), 1.50 (m, 4H), LCMS-ES 291.34 [M+H]$^+$.

Scheme 14-1

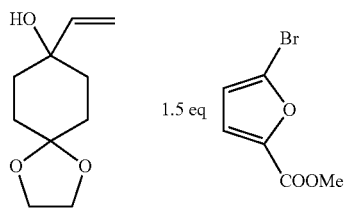

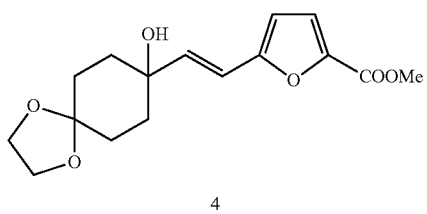

As shown in Scheme 14-2, LiOH (3 eq) was added to a solution of 100 mg of the resulting compound in Scheme 14-1 (compound 4) in THF:H$_2$O:MeOH (2:1:0.5 mL), and the mixture was stirred at RT for 16 h. The mixture was then concentrated under reduced pressure, and the crude was dissolved in minimum amount of water and acidified with 2 N HCl up to pH 4. Compounds were extracted with EtOAc and concentrated to yield a light brown solid (54 mg) which was used for next reaction (Scheme 14-3) without further purification. $^1$H NMR (400 MHz, DMSO-d$_6$), δ 7.50 (d 1H), 6.60 (d 1H), 6.45 (dd, 2H), 4.75 (s, 1H), 3.85 (s, 4H), 3.80 (s, 3H), 1.85 (m, 2H), 1.65 (m, 2H), 1.50 (m, 4H). LCMS-ES 277.26 [M+H]$^+$.

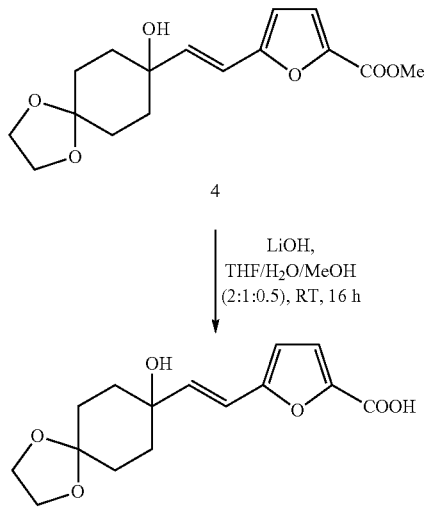

As shown in Scheme 14-3, 3 N HCl, 0.1 mL was added to compound 5 (50 mg) in THF at 0° C. with stirring. The mixture was allowed to warm to RT for 6 h. TLC shows absence of SM and a non-polar spot. The mixture was concentrated under reduced pressure, diluted with water, extracted with EtOAc, and re-concentrated to yield a brown solid (20 mg). $^1$H NMR (400 MHz, DMSO-d$_6$), δ 13.00 (bs 1H), 7.20 (d 1H), 6.95 (d 1H), 6.60 (d 1H), 6.45 (d, 1H), 6.10 (t, 1H), 3.05 (m, 2H), 2.65 (t, 2H), 2.5, (2H). LCMS-ES 233.21 [M+H]$^+$ LCMS-ES 231.27 [M−H]$^−$ 463.15 [2M−H]$^−$.

Scheme 14-3

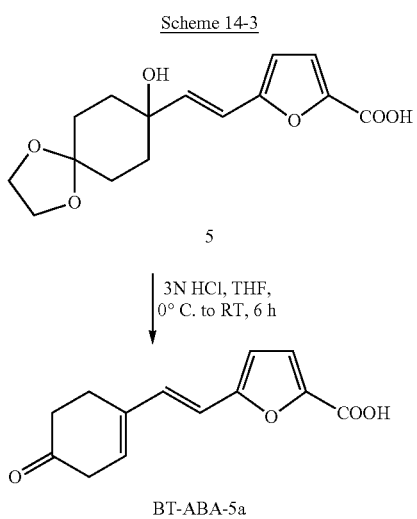

Example 15

BT-ABA-6

As shown in Scheme 15-1, a solution of 8-vinyl-1,4-dioxaspiro[4.5]decan-8-ol (500 mg, 1 eq), ethyl 3-iodobenzoate (0.8 eq), and PPh$_3$ (0.02 eq) in Et$_3$N (8 mL) was degassed with argon for 10 min. Then, Pd(OAc)$_2$ (0.02 eq) was added and again degased for 10 min. The resulting reaction mixture was heated at 95° C. for 16 h. After workup, a pale brown solid (500 mg) was isolated by column chromatography (EtOAc/hexane 3:7). $^1$H NMR (400 MHz, DMSO-d$_6$), δ 7.95 (s 1H), 7.80 (d 1H), 7.71 (d 1H), 7.47 (t 1H), 6.65 (d 1H), 6.49 (d, 1H), 4.65 (bs 1H), 4.32 (q, 2H), 3.68 (s, 4H), 1.99-1.68 (m, 4H), 1.55-1.50 (m, 4H), 1.33 (t 3H). LCMS-ES 315.38 [M−17]$^+$.

Scheme 15-1

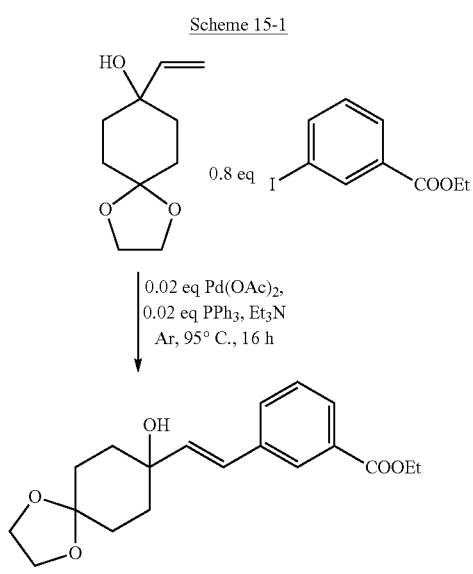

As shown in Scheme 15-2, a solution of compound 4 (500 mg) in THF/H$_2$O/EtOH (4:2:1, 17.5 mL) was cooled to 0° C.; LiOH (2.5 eq) was added, and the mixture was stirred while rising to RT over 16 h. The mixture concentrated under reduced pressure, and the crude was dissolved in minimum amount of water and acidified with 1 N HCl up to pH 3-4. Purification by column chromatography (EtOAc/hexane 1:1) gave a pale yellow solid (220 mg). $^1$H NMR (400 MHz, DMSO-d$_6$), δ 13.00 (bs 1H), 7.95 (s 1H), 7.78 (d 1H), 7.67 (d 1H), 7.44 (t 1H), 6.64 (d 1H), 6.48 (d, 1H), 4.65 (s 1H), 3.86 (s, 4H), 1.87-1.61 (m, 4H), 1.55-1.50 (m, 4H). LCMS-ES 287.34 [M−17]$^+$.

Scheme 15-2

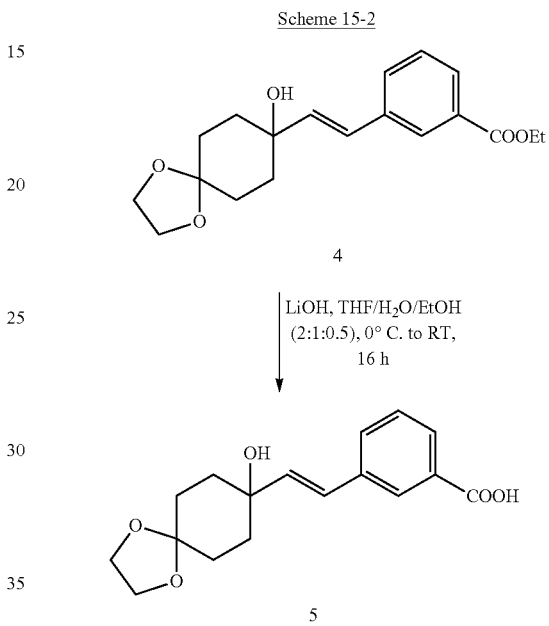

As shown in Scheme 15-3, 2 N HCl (1.5 mL) was added to a mixture of 100 mg of compound 5 (100 mg) in THF at 0° C. with stirring. The mixture was allowed to warm to RT for 6 h. The solution was then concentrated under reduced pressure, diluted with water, extracted with EtOAc, and re-concentrated to get a pale yellow solid (20 mg). $^1$H NMR (400 MHz, DMSO-d$_6$), δ 13.00 (bs 1H), 8.00 (s, 1H), 7.80 (d 1H), 7.65 (d 1H), 7.45 (t 1H), 6.75 (d 1H), 6.45 (d, 1H), 6.10 (t, 1H), 5.15 (s 1H), 2.65 (m, 2H), 2.15 (m, 2H), 1.90 (m, 4H), LCMS-ES 259.37 [M−H]$^-$ 519.48 [2M−H]$^-$.

Scheme 15-3

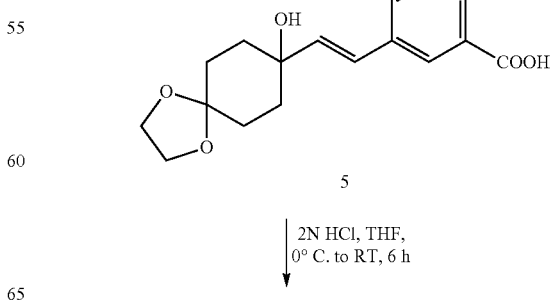

-continued

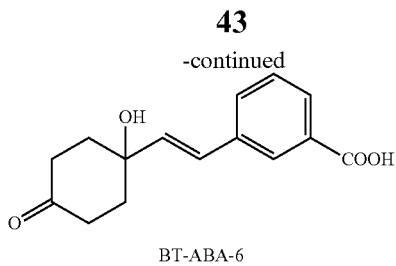

BT-ABA-6

Example 16

BT-ABA-13

As shown in Scheme 16-1, dihydropyran (1.3 eq) and TsOH (0.1 eq) was added to a solution of compound 2 (2.5 g, 1 eq) in $CH_2Cl_2$ (50 mL) at 0° C. with stirring. The resulting solution was allowed to gradually warm to RT for 14 h. A pale yellow liquid was isolated by column chromatography (EtOAc/hexane 1:9). The compound was used in the next step without further purification.

Scheme 16-1

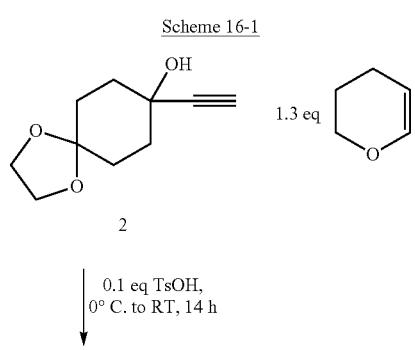

As shown in Scheme 16-2, compound 3 (2.5 g, 1.0 eq), 4,4,5,5-tetramethyl-[1,3,2]dioxaborolane (1.2 eq), and bis(cyclopentadienyl)zirconium chloride hydride (0.15 eq) were added to $Et_3N$. The resulting reaction mixture was heated at 60-70° C. for 16 h. The reaction mixture was diluted with hexanes. The precipitate was removed by filtration over short pad of silica gel and washed with hexanes. Upon concentration of the hexane solutions, a colorless oily liquid (1.3 g) was obtained. $^1H$ NMR (400 MHz, $CDCl_3$), δ 6.60 (d 1H), 5.60 (d 1 H), 6.35 (d, 1H), 4.75 (s, 1H), 3.85 (s, 3H), 2.80 (m, 2H), 2.35 (m, 2H), 2.05 (m, 4H).

Scheme 16-2

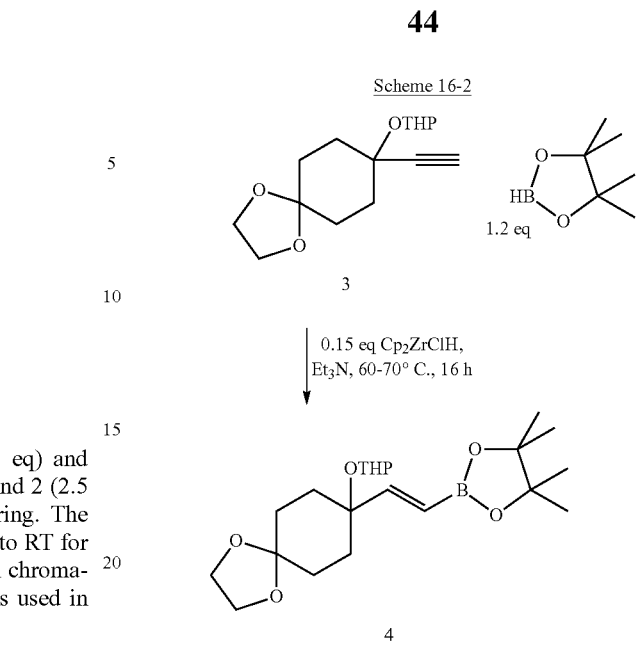

As shown in Scheme 16-3, a solution of compound 4 (550 mg, 1.1 eq), methyl 6-bromopicolinate (1.0 eq), $K_2CO_3$ (2.0 eq) in mixture of $DME/H_2O$ 9:1 (8 mL) was degassed with argon for 10 min. Then, $Pd[(P(Ph)_3]_4$ (0.04 eq) was added. The resulting reaction mixture was heated at 100° C. for 16 h. Concentration of the reaction solution followed by column chromatography (EtOAc/hexane 1:3) yielded a pale yellow solid (230 mg). LCMS -ES 404.39 $[M+H]^+$, 302.26 $[M-H]^+$.

Scheme 16-4

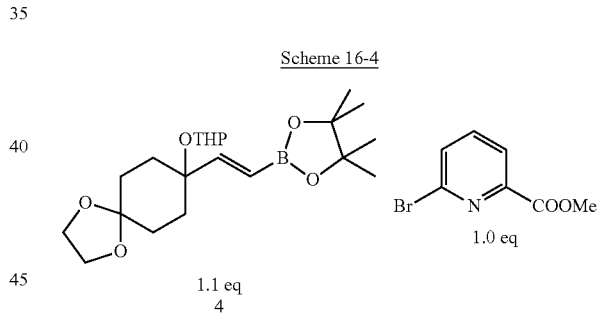

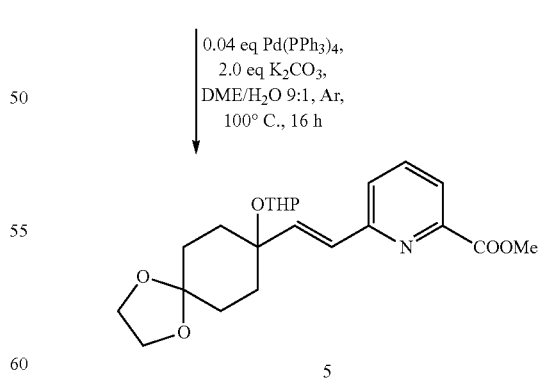

As shown in Scheme 16-5, TsOH (0.1 eq) was added to a solution of compound 5 (230 mg, 1.0 eq) in acetone/$H_2O$ 1:1 (6 mL). The resulting reaction mixture was stirred at room temperature for 16 h. Concentration of the reaction mixture followed by column chromatography (EtOAc/ hexane 7:3) gave a pale yellow liquid (110 mg). ¹H NMR (400 MHz, CDCl3), δ 8.00 (d 1H), 7.80 (t, 1H), 7.50 (d, 1H), 6.90 (m 2H), 4.00 (s, 3H), 2.80 (m, 2H), 2.35 (m, 2H), 2.10 (m, 4H), LCMS-ES 276.38 [M+H]⁺.

Scheme 16-5

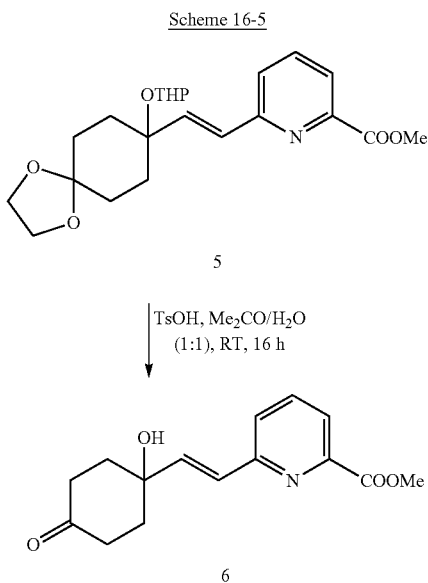

As shown in Scheme 16-6, LiOH (2.5 eq) was added to a solution of compound 6 (75 mg) in THF/H₂O 3:1 (3 mL) 0° C. with stirring. The mixture was allowed to warm to RT for 6 h. The reaction mixture was acidified with citric acid and extracted with a mixture of THF and EtOAc. Concentration of the organic solution gave an off-white solid (10 mg). ¹H NMR (300 MHz, DMSO-d₆), δ 13.05 (bs, 1H), 7.90 (m, 2H), 7.65 (d, 1H), 7.05 (d, 1H), 6.80 (d, 1H), 5.20 (s, 1H), 2.65 (m, 2H), 2.20 (bd 2H), 2.10-1.90 (m, 4H), LCMS-ES 262.27 [M+H]⁺.

Example 17

BT-ABA-16

As shown in Scheme 17-1, a solution of compound 4 (437 mg, 1.2 eq), methyl 2-bromoisonicotinate (1.0 eq), K₂CO₃ (2.0 eq) in mixture of DME/H₂O 9:1 (8 mL) was degassed with argon for 10 min. Then, Pd[(P(Ph)₃]₄ (0.04 eq) was added. The resulting reaction mixture was heated at 90° C. for 12 h. Concentration of the reaction solution followed by column chromatography (EtOAc/hexane 1:3) yielded a pale yellow liquid (300 mg). ¹H NMR (300 MHz, CDCl₃), δ 8.70 (d, 1H), 7.85 (s, 1H), 7.65 (d, 1H), 6.85 (d, 1H), 6.65 (d, 1H), 4.70 (m, 1H), 3.95 (m, 4H), 2.20-1.40 (m, 16H), LCMS-ES 404.54 [M+H]⁺, 302.53 [M−101]⁺.

Scheme 17-1

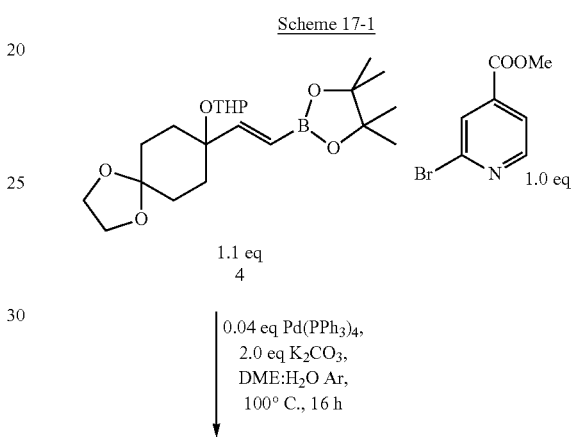

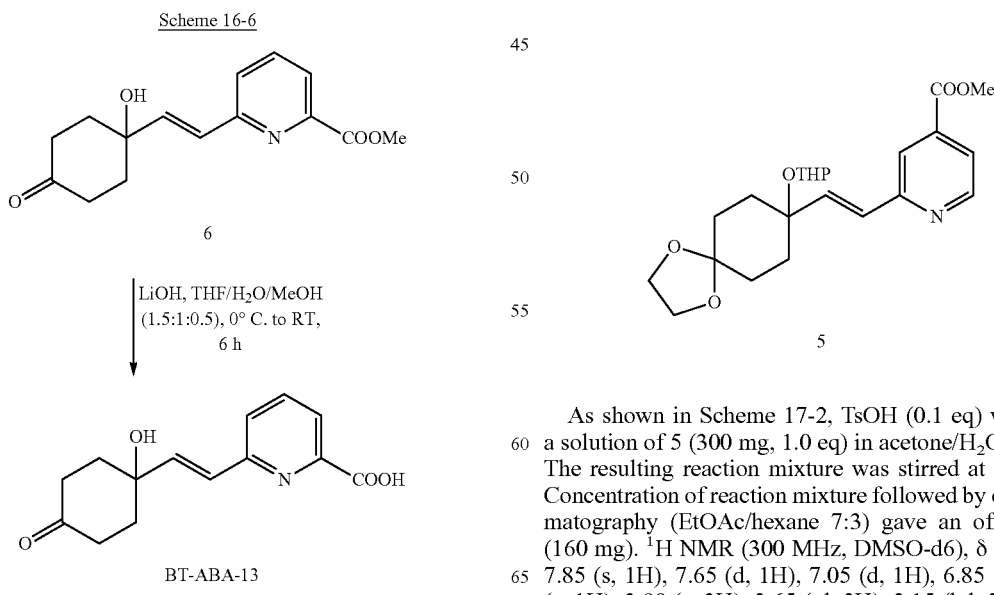

As shown in Scheme 17-2, TsOH (0.1 eq) was added to a solution of 5 (300 mg, 1.0 eq) in acetone/H₂O 1:1 (6 mL). The resulting reaction mixture was stirred at RT for 48 h. Concentration of reaction mixture followed by column chromatography (EtOAc/hexane 7:3) gave an off-white solid (160 mg). ¹H NMR (300 MHz, DMSO-d6), δ 8.70 (d, 1H), 7.85 (s, 1H), 7.65 (d, 1H), 7.05 (d, 1H), 6.85 (d, 1H), 5.20 (s, 1H), 3.90 (s, 3H), 2.65 (td, 2H), 2.15 (bd, 2H), 2.00 (m, 2H), 1.85 (m, 2H), LCMS-ES 276.22 [M+H]⁺.

Scheme 17-2

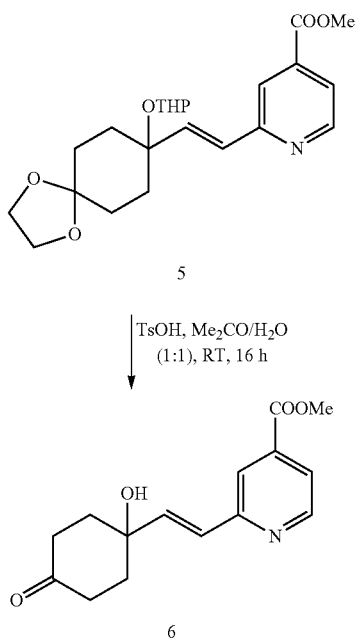

As shown in Scheme 17-3, LiOH (2.5 eq) was added to a solution of compound 6 (100 mg) in THF/H₂O 3:1 (3 mL) at 0° C. with stirring. The mixture was allowed to warm to RT for 16 h. The reaction mixture was acidified with citric acid and extracted with mixture of THF and EtOAc. Concentration under reduced pressure gave an off-white solid (20 mg). ¹H NMR (300 MHz, DMSO-d6), δ 13.60 (bs, 1H), 8.70 (d, 1H), 7.85 (s, 1H), 7.60 (d, 1H), 7.00 (d, 1H), 6.85 (d, 1H), 5.20 (s, 1H), 2.65 (m, 2H), 2.20-1.80 (m, 6H), LCMS-ES 262.28 [M+H]⁺.

Scheme 17-3

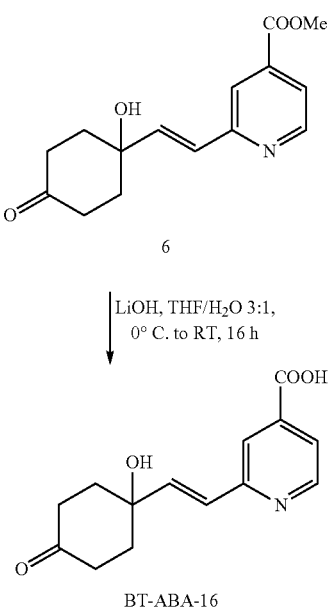

Example 18

BT-ABA-14

As shown in Scheme 18-1, a solution of compound 4 (300 mg, 1.2 eq), methyl 4-bromopicolinate (1.0 eq), K₂CO₃ (2.0 eq) in mixture of DME/H₂O 9:1 (8 mL) was degassed with argon for 10 min. Then, Pd[(P(Ph)₃]₄ (0.04 eq) was added. The resulting reaction mixture was heated at 90° C. for 12 h. Concentration of the reaction solution followed by column chromatography (EtOAc/hexane 1:3) yielded a pale yellow liquid (200 mg). ¹H NMR (300 MHz, CDCl₃), δ 8.50 (d, 1H), 8.20 (bs, 1H), 7.45 (d, 1H), 6.70 (d, 1H), 6.50 (d, 1H), 4.60 (m, 1H), 3.95 (m, 4H), 2.20-1.40 (m, 16H), LCMS-ES 390.35 [M+H]⁺.

Scheme 18-1

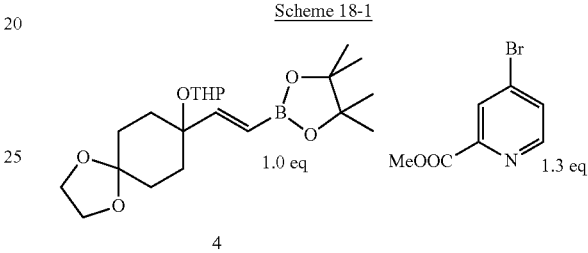

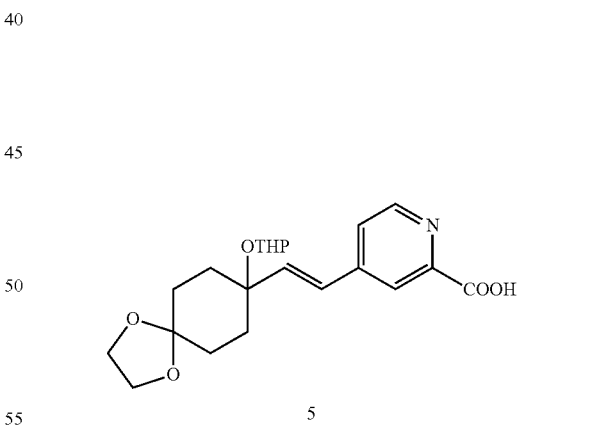

As shown in Scheme 18-2, TsOH (0.1 eq) was added to a solution of 5 (200 mg, 1.0 eq) in acetone/H₂O 1:1 (6 mL). The resulting reaction mixture was stirred at room temperature for 48 h. The reaction mixture was acidified with citric acid and extracted with mixture of THF and EtOAc. The solution was concentrated to give an off-white solid (18 mg). ¹H NMR (300 MHz, DMSO-d₆), δ 8.60 (d, 1H), 8.05 (s, 1H), 7.60 (d, 1H), 6.90 (d, 1H), 6.70 (d, 1H), 5.20 (bs, 1H), 2.65 (m, 2H), 2.15 (bd, 2H), 2.05-1.80 (m, 4H), LCMS-ES 262.27 [M+H]⁺.

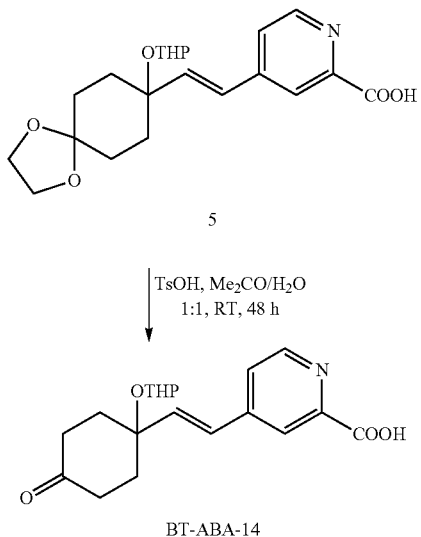

BT-ABA-14

RECEPTOR BINDING EXAMPLES

Example 19

LANCL2 Binding Example

Computational modeling studies and biochemical validation were combined to guide the selection on compounds that bind to LANCL2. Latest iterations of surface plasmon resonance (SPR) technology provide an in vitro, high throughput, quantitative means to determine molecular interaction between label-free proteins and small molecules (>25 Da) in real time. BIACORE™ T200 (GE Healthcare, Piscataway, N.J.) technology further provides an added benefit of GMP/GLP compliance and autonomous large-scale data acquisition either of screens or detailed titrations in less than 24-hour period. Molecular interactions of interest are routinely validated by BIACORE™ T200 SPR technology.

Methods

High-throughput screening via molecular modeling of LANCL2-compound interactions. Auto-Doc Vina [14] is a state of the art software suite capable of high-throughput parallel computations to ascertain LANCL2-botanical compound binding. The software suite first computes (i) the forces of free energy associated with the bound complex and subsequently (ii) the conformational space available for the complex formation between target and ligand. These methods are stochastic in nature therefore require repeated independent screens to exhaustively search all parameter spaces and provide confidence in predictions. Currently the model of LANCL2 is available through homology modeling of LANCL1 [15]. AutoDockTools, the graphical front-end for AutoDock and AutoGrid, was used to define the search space, including grid box center and x,y,z-dimensions [16]. AutoDock Vina generated five bound conformations for each compound. The docking is applied to the whole protein target, with a grid covering the whole surface of the protein. Docking log files were generated consisting of binding energies of each predicted binding mode for all the compounds for all surfaces.

Kinetic determination of LANCL2-small molecule interaction. BIACORE™ T200 was used to determine the kinetic parameters for the binding of small molecules BT-11, BT-ABA-5a, BT-6, and BT-15 (analytes) to LANCL2 (ligand). Data were generated in a dose dependent (5-8 titration points) manner in triplicate, and analyzed to determine binding model (Langmuir, conformational shift, etc.), real time associated and disassociation constants, and equilibrium dissociation constant. SPR technology allowed validation of specific LANCL2-phytochemical interactions as well as to gain gold-standard insight into mechanism and rate of binding. The experiments were performed on carboxymethyldextran (CM5) sensor chips by covalently attaching LANCL2 to by amine coupling. Flow cells 1 and 2 of the sensor chip were activated for 720 sec at 10 µl/min with of 1:1 mixture of 0.1 M N -hydroxysuccinimide (NHS) and 0.5 M 1-ethyl-3-(-3-dimethylaminopropyl)-carbodiimide hydrochloride (EDC). Stock LANCL2 (0.41 mg/mL) was diluted to 8.2 µg/mL (1:50 dilution) in 10 mM sodium acetate, pH 5.0 and injected over the activated flow cell 2 surface for 1000 sec at a flow rate of 10 µl/min. After the capture of LANCL2 on flow cell 2 (11000 RU), surfaces of flow cells 1 and 2 were deactivated by injecting 1 M ethanolamine for 720 sec at 10 µl/min. The running buffer was 25 mM MOPS containing 0.05% T-20 and 0.15 M NaCl, pH 6.5. Kinetic studies were performed by injecting different concentrations of the BT-11 (25 µM, 12.5 µM, 6.25 µM, 3.13 µM, 1.56 µM, and 0.76 µM), BT-ABA-5a (40 µM, 20 µM, 10 µM, 5 µM, 2.5 µM, and 1.25 µM) and BT-15/BT-6 (20 µM, 10 µM, 5 µM, 2.5 µM, 1.25 µM, 0.625 µM, and 0.313 µM) in triplicates. Each sample was injected for 60 sec (contact time) followed by a dissociation time of 60 sec at a flow rate of 100 µL/min. A stabilization time of 180 sec was used before the next injection. Data was analyzed with BIACORE™ T200 Evaluation Software (version 1) to determine the affinity binding constant (KD) using a 1:1 binding model.

Results

Figure 8:
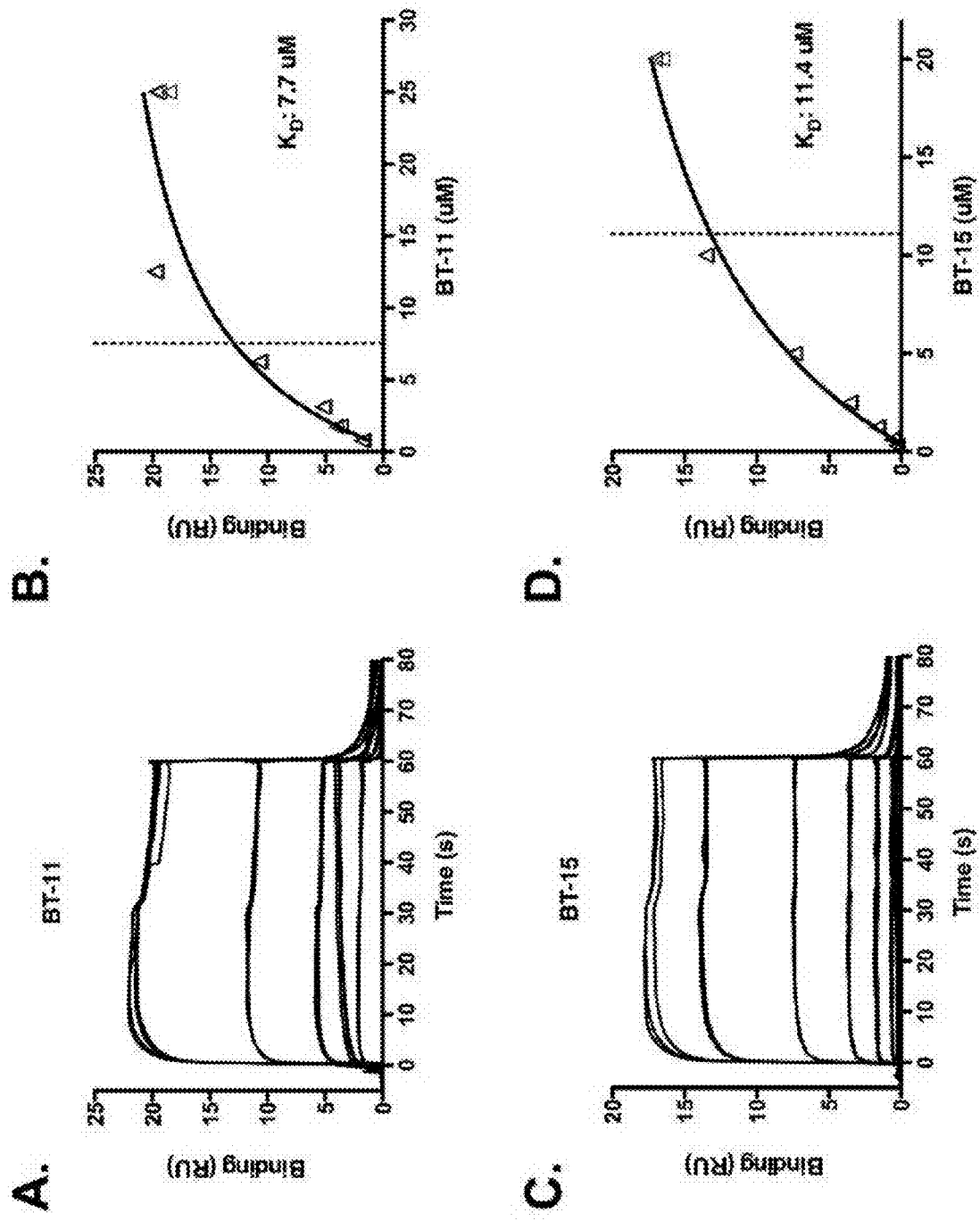
FIG. 8. Binding kinetics of lanthionine synthetase C-like protein 2 (LANCL2) with BT-11 and BT-15. Panels A and C show surface plasmon resonance (SPR) sensorgrams for the binding of varying concentrations of BT-11 (A) and BT-15 (C) to immobilized LANCL2. Panels B and D show plots of maximal resonance unit (RU) versus concentration of BT-11 (B) and BT-15 (D). Steady state dissociation constants ($K_D$) utilizing a 1:1 binding model are indicated.

Both BT-11 and BT-15 strongly bind to LANCL2. In order to confirm binding of BT -11 and BT-15 to the LANCL2 protein, we performed SPR analyses in a BIACORE™ T-200 instrument. SPR, an optical technique utilized for detecting molecular interactions, was used to measure binding affinity between LANCL2 and its ligands (i.e., BT-11 and BT-15). We immobilized purified recombinant LANCL2 protein on BIACORE™ sensor chips and injected small molecules over the protein surface using the microfluidic system of the instrument. Changes in the total mass on chip surface were measured, which corresponds to the small binding to the protein. By injecting a series of small molecule concentrations we were able to calculate steady state binding affinities for BT-11 binding to LANCL2 and BT -15 binding to LANCL2. Binding sensorgrams showed a typical small molecule protein interaction with very fast on rates and very fast off rates (FIG. 8, panels A and C). These fast interactions are beyond the technical abilities of the instrument. Therefore, reliable association rate constant ($k_a$) and dissociation rate constant ($k_d$) were not determined. The equilibrium dissociation constant ($K_D$) is commonly used to describe the affinity between a ligand and a protein, such as how tightly a ligand binds to a particular protein. Ligand-protein affinities are influenced by non-covalent intermolecular interactions between the two molecules such as hydrogen bonding, electrostatic interactions, hydrophobic and Van der Waals forces. By plotting the equilibrium binding level against the compound concentration, we were able to measure the steady state affinity ($K_D$) for each interaction (FIG. 8, panels B and D). Both small molecules showed a similar binding affinity for LANCL2 (BT-11: 7.7 uM, BT-15 11.4 uM).

Figure 9A:
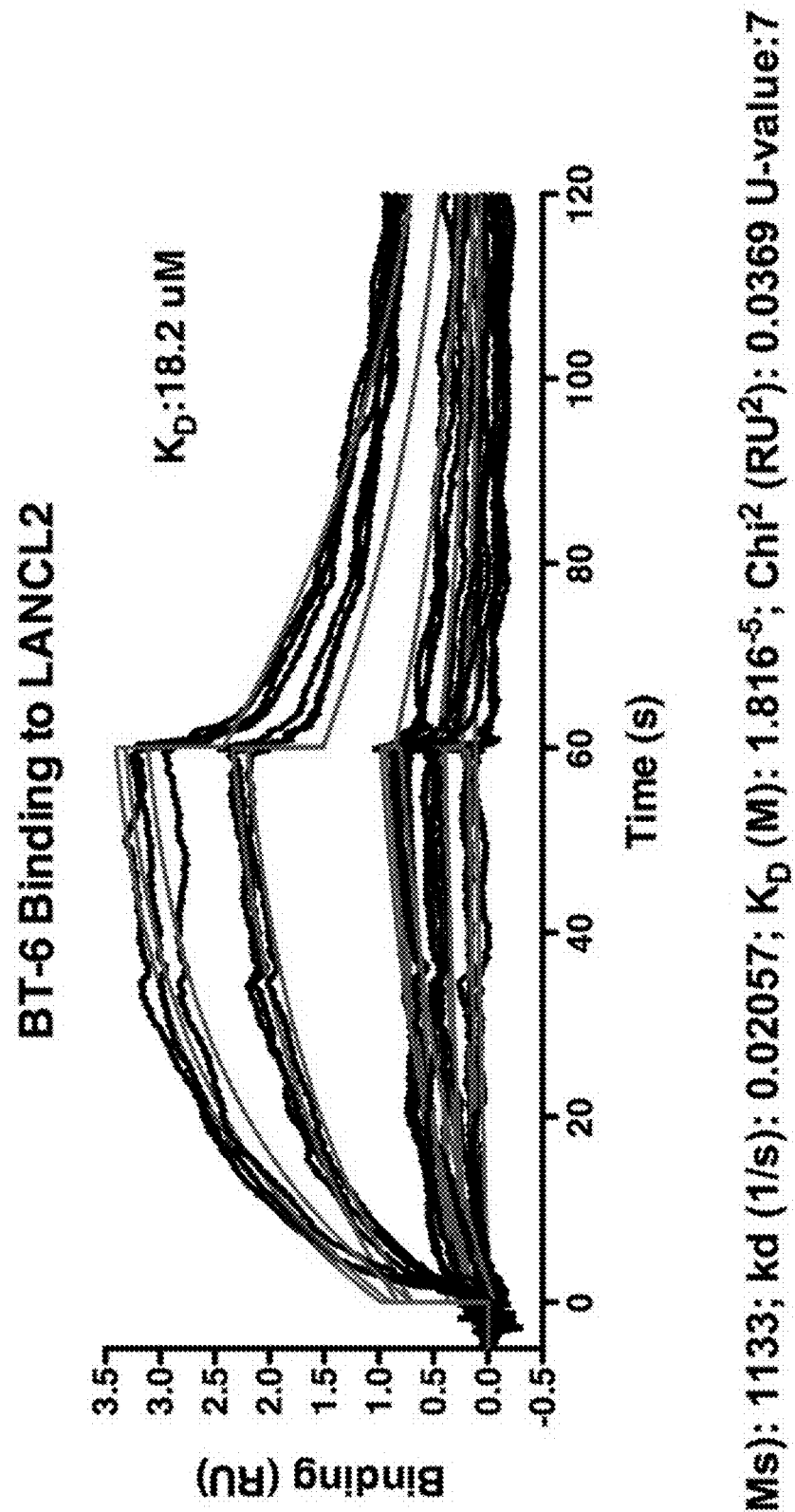
FIGS. 9A and 9B. Binding kinetics of lanthionine synthetase C-like protein 2 (LANCL2) with BT-6 (FIG. 9A) and BT-ABA-5a (FIG. 9B). Surface plasmon resonance (SPR) sensorgrams for the binding of varying concentrations of BT-6 and BT-ABA-5a to immobilized LANCL2 are shown.
Figure 9B:
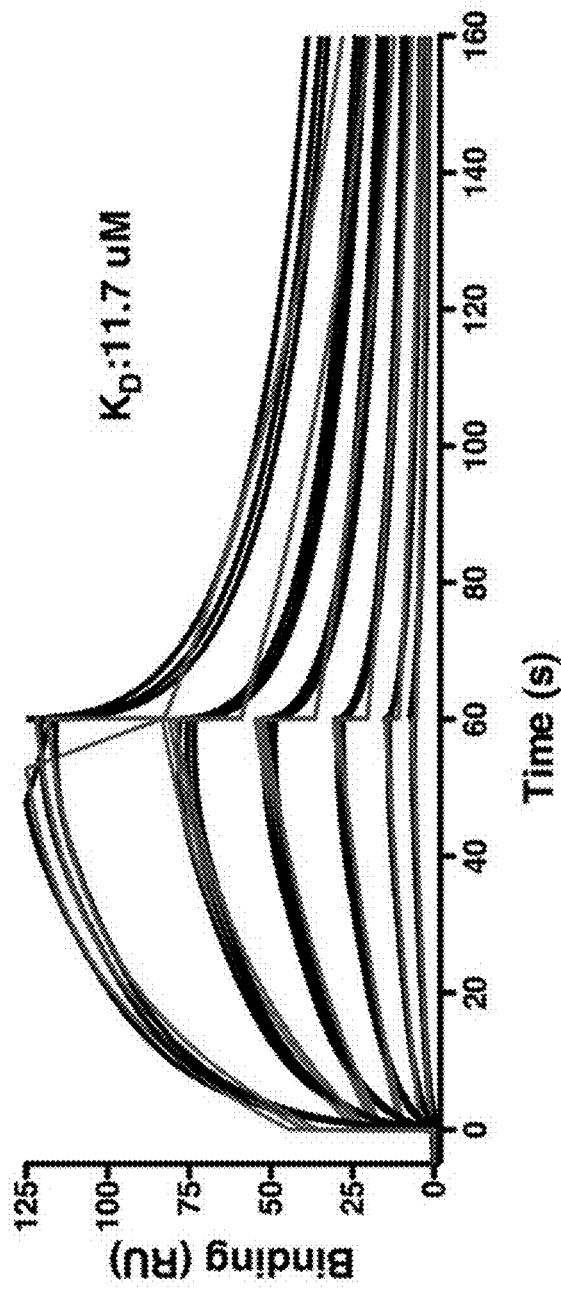

BT-ABA-5a and BT-6 strongly bind to LANCL2. Similar to the results described above and in order to confirm binding of BT-6 and BT-ABA-5a to LANCL2, we performed SPR analyses in a BIACORE™ T-200 instrument. In this case we also immobilized purified recombinant LANCL2 protein on BIACORE™ sensor chips and injected small molecules over the protein surface using the microfluidic system of the instrument. Changes in the total mass on chip surface were measured, which corresponds to the small binding to the protein. Taking a closer look at the binding sensorgrams (FIGS. 9A and 9B), our results show how BT-6 and BT-ABA-5a are very fast to bind but not as fast as off, in comparison to BT -11/BT-15, which are very fast on and very fast off. Of note, the occupancy time for BT -ABA-5a shows the slowest off rate, meaning that BT-ABA-5a stays the longest in the binding pocket of LANCL2. This longer binding can potentially impact the activation of the LANCL2 pathway by triggering more efficacious anti-inflammatory and anti-diabetic and other therapeutic responses.

Other compounds have been tested via SPR, and the results are comprehensibly shown in FIGS. 1A and 1B.

EXPERIMENTAL STUDIES EXAMPLES

Example 20

Use of BT-11 on an Acute Model of IBD

Introduction

Inflammatory bowel disease (IBD), a chronic, recurring disease of the gastrointestinal tract, afflicts over 1.4 million people in the U.S. IBD comprises two different manifestations: ulcerative colitis and Crohn's disease. Current therapies against IBD are modestly successful and have significant adverse side effects for the long-term management of the disease [17]. Whereas Crohn's disease represents the chronic stage of the disease, acute ulcerative colitis (UC) is manifested as an early pathology that affects the colonic tissue. UC is a chronic idiopathic inflammatory disorder of the GI tract characterized by mucosal inflammation of the rectum that extends proximally through the colon, in a continuous fashion, but to a variable extent. The disorder is characterized by a relapsing and remitting course of variable severity. The majority of patients present with left-sided or distal disease of mild-to-moderate severity. Most remain in remission for long periods with maintenance medical therapy. However, natural history studies suggest that between 10 and 40% will undergo a colectomy at some point during the course of their disease.

Medical treatment of steroid-refractory severe UC has expanded somewhat in recent years with the availability of both cyclosporin and infliximab as rescue agents; however surgery still remains the only "curative" option. The present invention provides a novel drug product for the treatment of UC by targeting a novel receptor named LANCL2. BT-11, our top lead compound, is administered orally and distributed systemically, and exerts immune modulatory effects in UC by targeting LANCL2 in gut immune cells. Our preclinical efficacy studies in acute UC in mice showed how administration with BT-11 reduces the disease activity index and improves gut inflammation by significantly decreasing leukocytic infiltration in the gut mucosa, as well as decreasing mucosal thickening and epithelial erosion. Gene expression analyses confirmed that oral administration of BT-11 upregulates the expression of IL-10 and LANCL2, and downregulates the expression of TNFα mRNA in a model of acute DSS-induced ulcerative colitis in mice.

Methods

Mice. C57BL/6 were purchased from the Jackson Laboratory and housed under specific pathogen-free conditions in ventilated racks. LANCL2−/− mice were purchased from the KOMP repository at University of California Davis. All mice were maintained in animal facilities. All experimental protocols were approved by an institutional animal care and use committee and met or exceeded guidelines of the National Institutes of Health Office of Laboratory Animal Welfare and Public Health Service policy.

DSS-induced colitis. Colitis was induced in C57BL/6J mice by administration of 5% (w/v) dextran sodium sulfate (DSS; molecular weight 42 kDa; ICN Biochemicals, Aurora, Ohio) added to the drinking water. Colonic inflammation was assessed 7 days after DSS treatment. The groups in the DSS project consisted of i. non-DSS vehicle-treated mice, ii. non-DSS, BT-11 (80 mg/Kg) treated mice, iii. DSS-treated, vehicle-treated mice, and iv. DSS-treated, BT-11 (80 mg/Kg) treated mice. Twelve mice were included in each group.

Histopathology. Colonic sections from IBD studies in mice were fixed in 10% buffered neutral formalin, later embedded in paraffin and then sectioned (5 µm) and stained with H&E stain for histological examination. Colons were graded with a compounded histological score including the extent of (1) leukocyte infiltration, (2) mucosal thickening and (3) epithelial cell erosion. The sections were graded with a score of 0-4 for each of the previous categories, and data were analyzed as a normalized compounded score.

Quantitative Real-Time PCR. Total RNA was isolated from mouse colons using an RNEASY PLUS MINI KIT (Qiagen, Valencia, Calif.) according to the manufacturer's instructions. Total RNA (1 µg) was used to generate a cDNA template using an ISCRIPT™ cDNA Synthesis kit (Bio-Rad, Hercules, Calif.). The total reaction volume was 20 µL, with the reaction incubated as follows in an MJ MINI™ thermal cycler (Bio-Rad): 5 min. at 25° C., 30 min at 52° C., 5 min at 85° C., and hold at 4° C. PCR was performed on the cDNA using Tag DNA polymerase (Life Technologies, Carlsbad, Calif.). Each gene amplicon was purified with the MINELUTE PCR Purification kit (Qiagen) and quantified both on an agarose gel by using a DNA mass ladder (Promega, Madison, Wis.) and with a nanodrop. These purified amplicons were used to optimize real-time PCR conditions and to generate standard curves in the real-time PCR assay. Primers were designed using Oligo 6 software. Primer concentrations and annealing temperatures were optimized for the ICYCLER IQ™ system (Bio-Rad) for each set of primers using the system's gradient protocol. PCR efficiencies were maintained between 92 and 105% and correlation coefficients >0.98 for each primer set during optimization and also during the real-time PCR of sample DNA. cDNA concentrations for genes of interest were examined by real-time qPCR using an ICYCLER IQ™ m System and the IQ™ SYBR® Green Supermix (Bio-Rad). A standard curve was generated for each gene using 10-fold dilutions of purified amplicons starting at 5 pg of cDNA and used later to calculate the starting amount of target cDNA in the unknown samples. SYBR® green I is a general double-stranded DNA intercalating dye and may therefore detect nonspecific products and primer/dimers in addition to the amplicon of interest. To determine the number of products synthesized during the real-time PCR, a melting curve analysis was performed on each product. Real-time PCR was used to measure the starting amount of nucleic acid of each unknown sample of cDNA on the same 96-well plate.

Statistical Analysis. Parametric data were analyzed using the ANOVA followed by Scheffe's multiple comparison method. Nonparametric data were analyzed by using the Mann-Whitney's U test followed by a Dunn's multiple comparisons test. ANOVA was performed by using the general linear model procedure of SAS, release 6.0.3 (SAS Institute). Statistical significance was assessed at a P≤0.05.

Results

Figure 10:
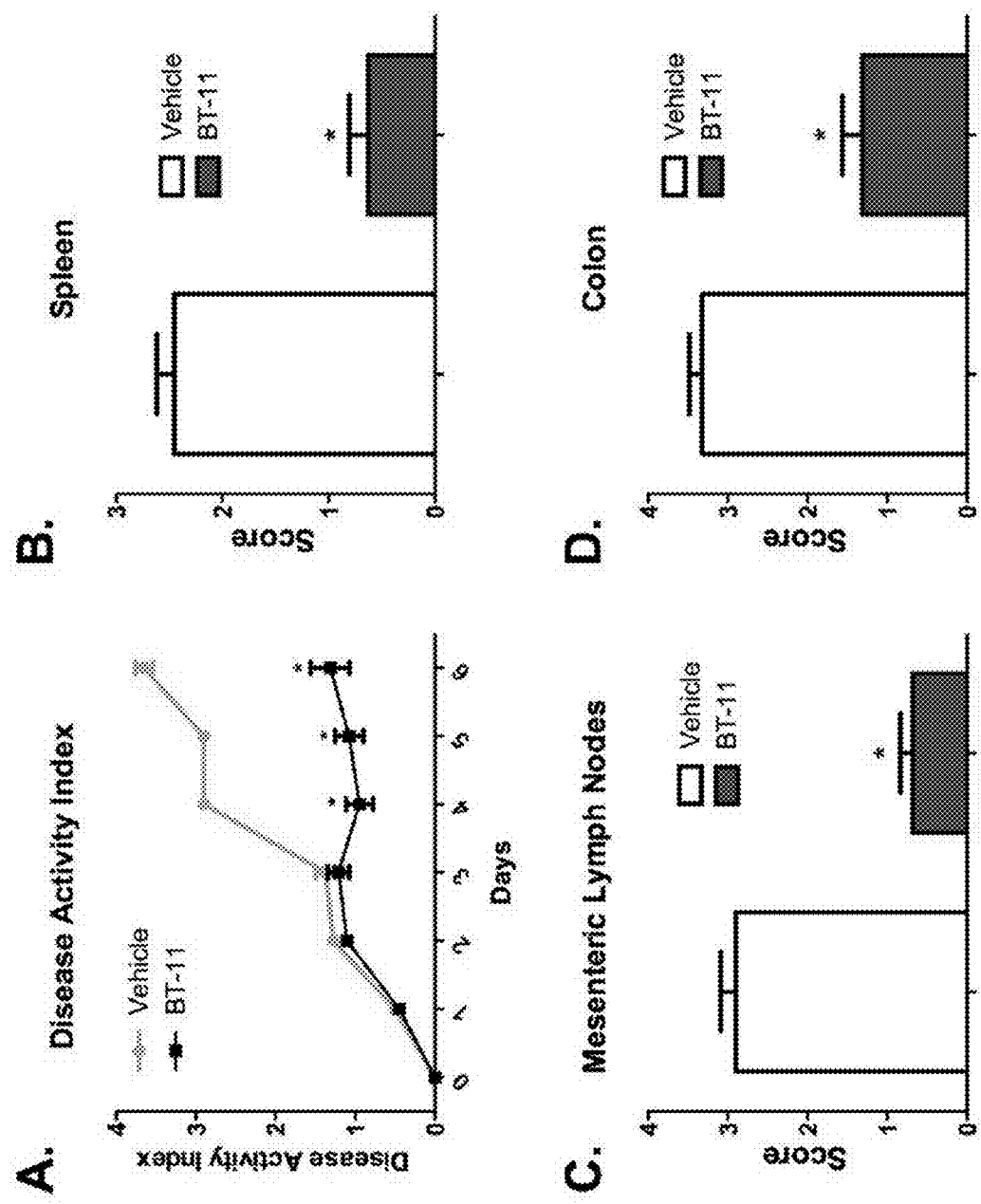
FIG. 10. Effect of oral administration on disease activity and gross pathology of mice with dextran sodium sulfate (DSS) colitis. Panel A shows disease activity index scores in mice treated with either BT-11 or vehicle only. Panels show gross pathology scores from the (B) spleen, (C) mesenteric lymph nodes (MLN), and (D) colon in mice treated with either vehicle or BT-11. Statistically significant differences (P<0.05) are indicated with an asterisk (n=10).

BT-11 improves disease and tissue pathology in a DSS model of colitis. The objective of this study was to investigate whether administration of BT-11 activates LANCL2 and exerts anti-inflammatory properties in the context of IBD. To assess the efficacy of our exemplary compound BT-11 in an acute model of IBD, we treated C57BL/6J mice with 5% DSS on a 7-day challenge. Throughout the challenge period, the treatment with BT-11 significantly improved the score in disease activity (FIG. 10, panel A). Furthermore, the macroscopic lesions in the spleen (FIG. 10, panel B), the MLNs (FIG. 10, panel C) and the colon (FIG. 10, panel D) were also significantly decreased following activation of the LANCL2 pathway by using BT-11 at day 7 post-challenge.

Figure 11:
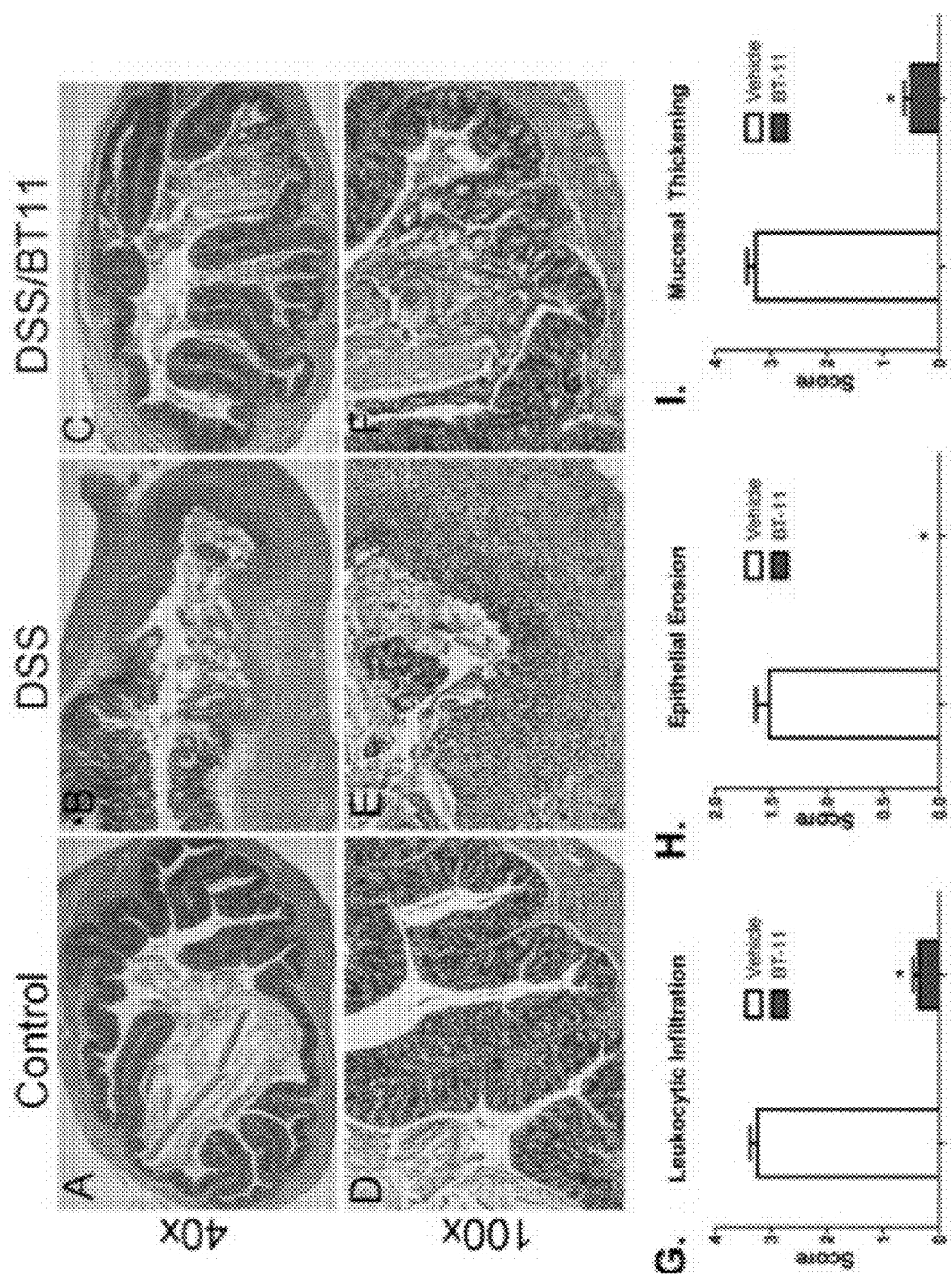
FIG. 11. Effect of oral BT-11 administration on colonic inflammatory lesions in mice with DSS colitis. Representative micrographs of (A, D) control (B, E) DSS, and (C, F) BT-11 treated DSS mice are shown. Histopathological lesions were evaluated based on (G) leukocytic infiltration, (H) epithelial erosion, and (I) mucosal thickening. Statistically significant differences (P<0.05) are indicated with an asterisk (n=10).
Figure 12:
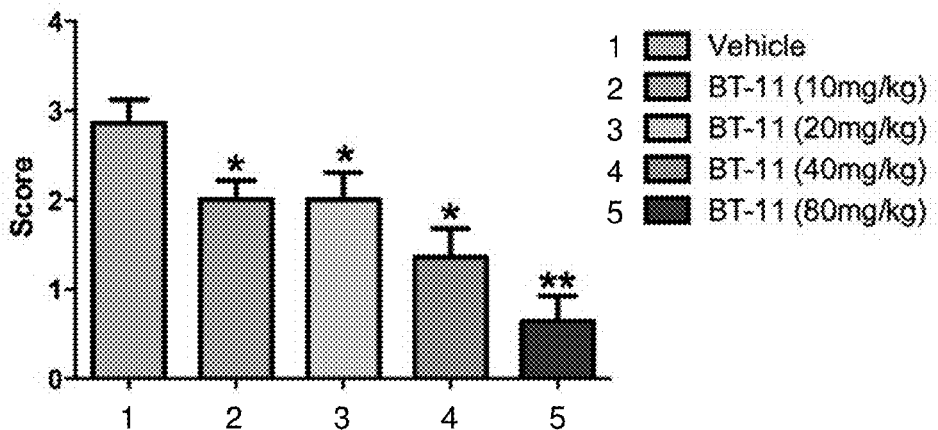
FIG. 12. Dose-Response effect of oral BT-11 administration on colonic inflammatory lesions in mice with DSS colitis. Histopathological lesions were evaluated based on (A) leukocytic infiltration, (B) mucosal thickening, and (C) epithelial erosion. Statistically significant differences (P<0.05) are indicated with an asterisk (n=10).
Figure 12:
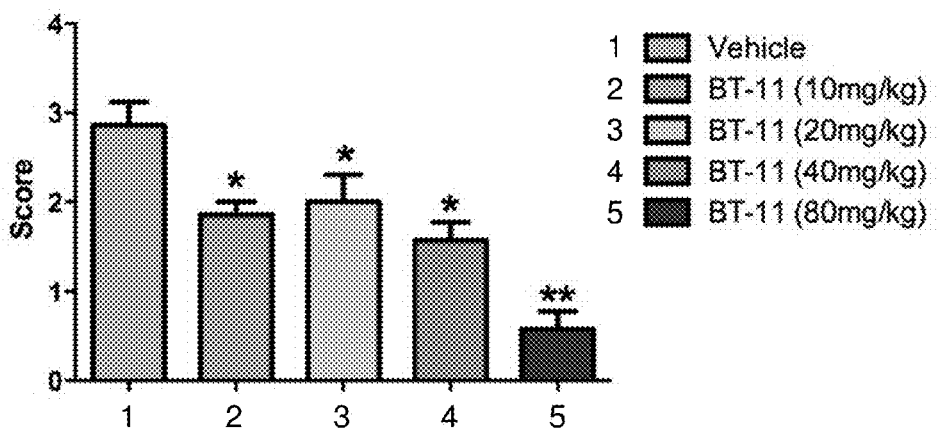
Figure 12:
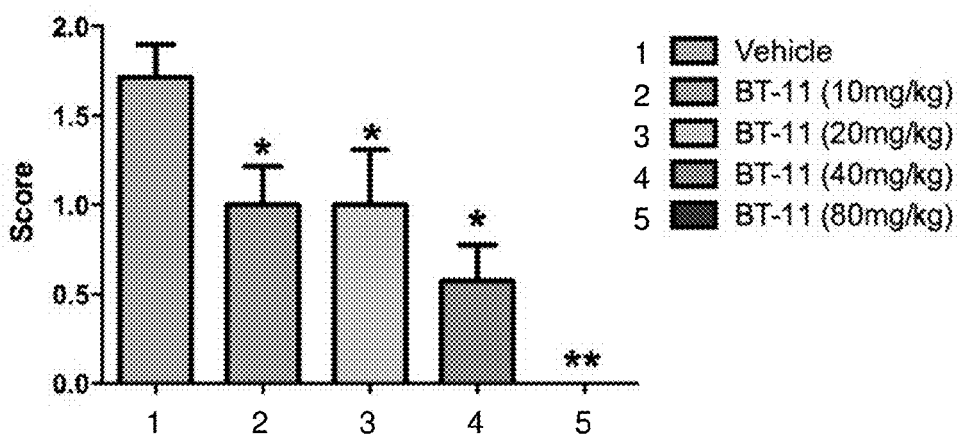

BT-11 improves colonic histopathology in mice with acute inflammatory colitis in a dose response manner. We next examined the effect of BT-11 on histopathological colonic inflammatory lesions. In line with our observations of disease activity and gross lesions, histopathological analyses confirmed that treatment with BT-11 significantly decreased by 5 times the inflammation in the gut mucosa based on assessment of leukocytic infiltration (FIG. 11, panel G), epithelial erosion (FIG. 11, panel H), and mucosal thickening (FIG. 11, panel I). Representative colonic micrographs show how treatment with BT-11 during DSS-induced colitis in mice significantly improves the status of the gut mucosa by improving epithelial cell integrity and reducing the destruction of the gut architecture, as well as the infiltration of several immune subsets (FIG. 11, panels A-F). We performed dose-response studies with BT-11 and we interestingly observed how the three hallmarks of colonic inflammation (leukocytic infiltration, mucosal thickening, and epithelial erosion) were decreased in mice with colitis as the dose of BT-11 was increased from 10 to 80 mg/Kg (FIG. 12, panels A-C).

Figure 13:
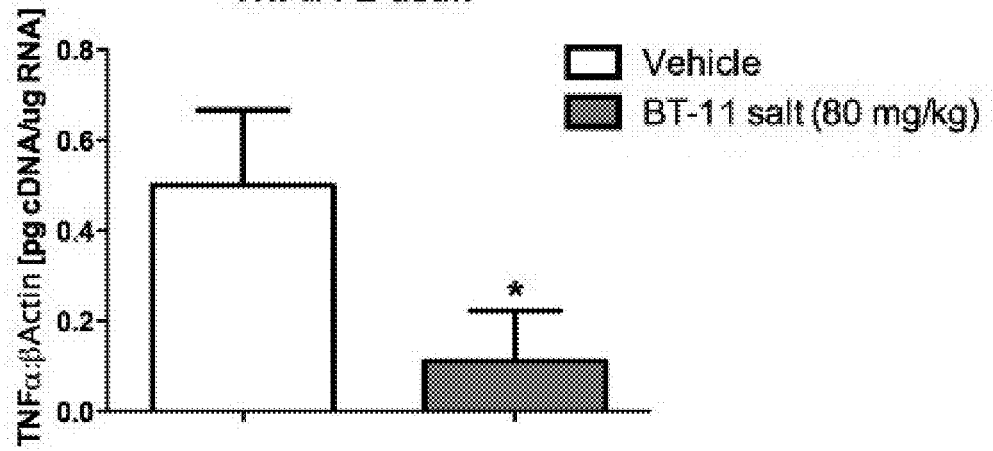
FIG. 13. Colonic gene expression analysis of TNFα, interleukin 10 (IL-10) and LANCL2. Colonic gene expression to assess the levels of (A) proinflammatory TNFα, (B) IL-10, and (C) LANCL2 are shown. Statistically significant differences (P<0.05) are indicated with an asterisk (n=10).
Figure 13:
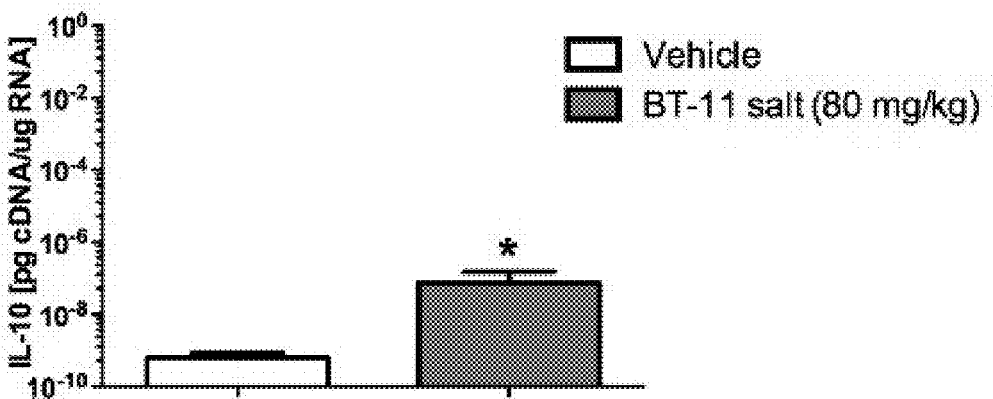
Figure 13:
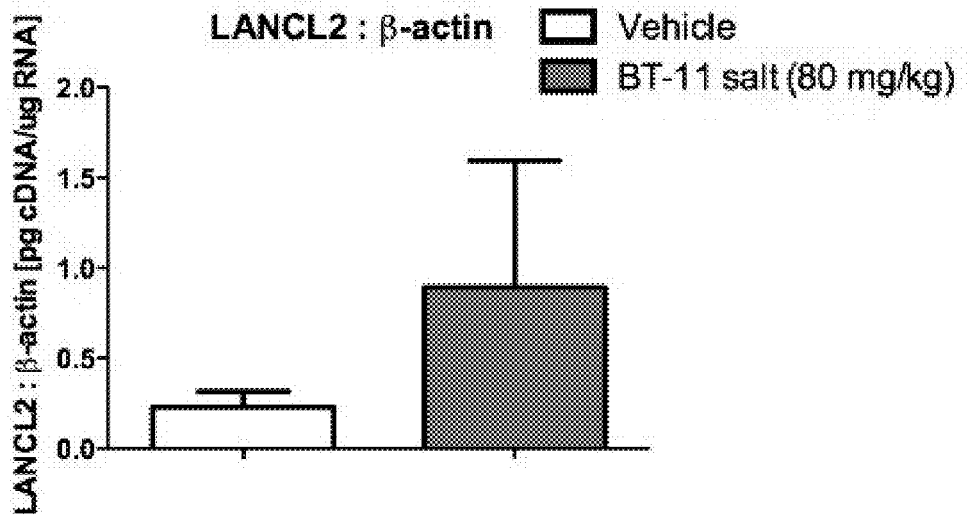
Figure 14:
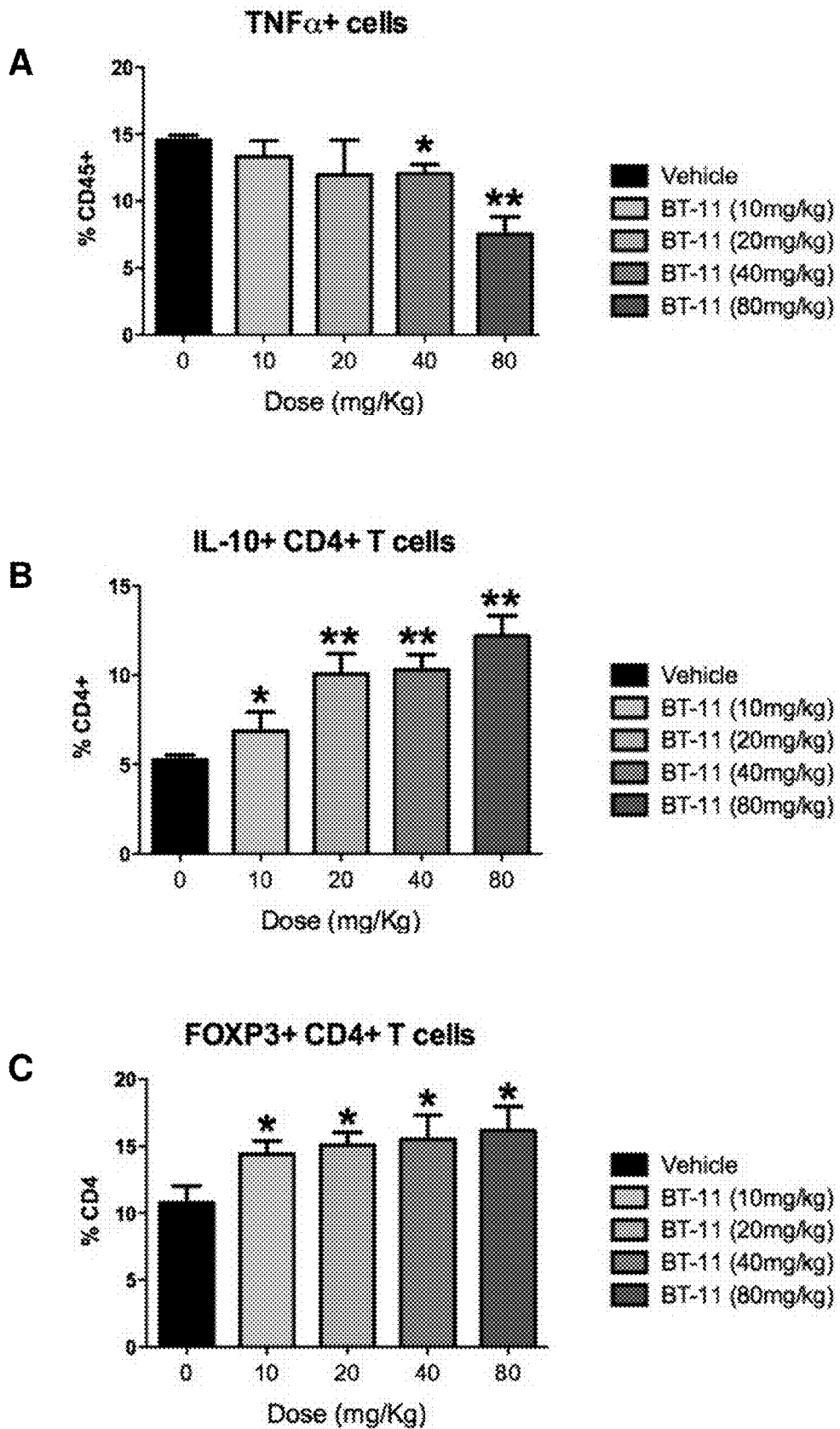
FIG. 14. Dose-Response effect of oral administration of BT-11 on colonic pro- and anti-inflammatory immune cell subsets in mice with DSS colitis. Flow cytometry analyses were used to measure (A) TNFa+ cells, (B) IL-10+ CD4+ T cells, and (C) FOXP3+ CD4+ T cells in the colonic mucosa.

Oral treatment with BT-11 reduces the expression of TNFα and upregulates LANCL2 and IL-10. To more closely investigate the effect of BT-11 on the modulation of the immune system, we assessed genetic expression of IL-10, LANCL2, and TNFα. Results show how treatment with BT-11 down-regulated the expression of tumor necropsis factor alpha (TNFα) (FIG. 13, panel A), as well as upregulated the levels of Interleukin 10 (IL-10) (FIG. 13, panel B) and the LANCL2 receptor (FIG. 13, panel C), therefore creating a positive feedback loop that promotes anti-inflammatory effects and down-regulates the inflammatory response driven by TNFα. By performing a dose-response study we could hypothesize that our ligand BT-11 and the following activation of the LANCL2 pathway directly increases the production of colonic IL-10, as its expression assessed by flow cytometry follows dose-response dynamics with BT-11 (FIG. 14, panel B). We observed that the reduction of colonic TNFα expressing cells was significantly different at both 40 and 80 mg/Kg of BT-11, but not on lower doses, such as 10 or 20 mg/Kg (FIG. 14, panel A). We also observed how FOXP3 expression in the MLN is dose-dependent (FIG. 14, panel C).

Figure 15:
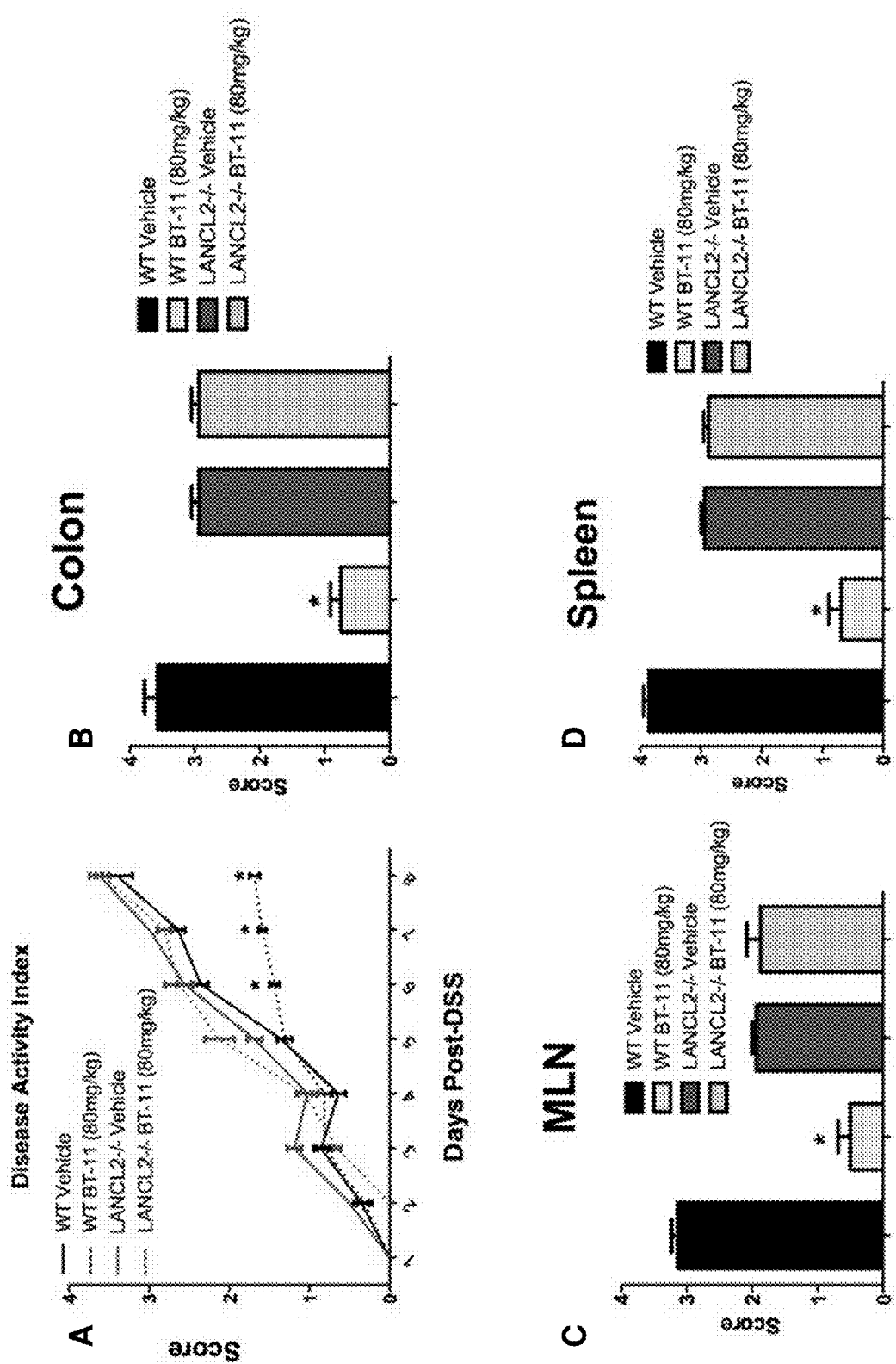
FIG. 15. Effect of oral BT-11 administration on tissue gross pathology lesions in wild-type and LANCL2−/− mice with DSS colitis. Panel A shows disease activity index scores in wild-type versus LANCL2−/− mice treated with either BT-11 or vehicle only. Panels B-D show gross pathology scores from the (B) colon, (C) mesenteric lymph nodes (MLN), and (D) spleen in wild-type and LANCL2−/− mice treated with either vehicle or BT-11. Statistically significant differences (P<0.05) are indicated with an asterisk (n=10).
Figure 16:
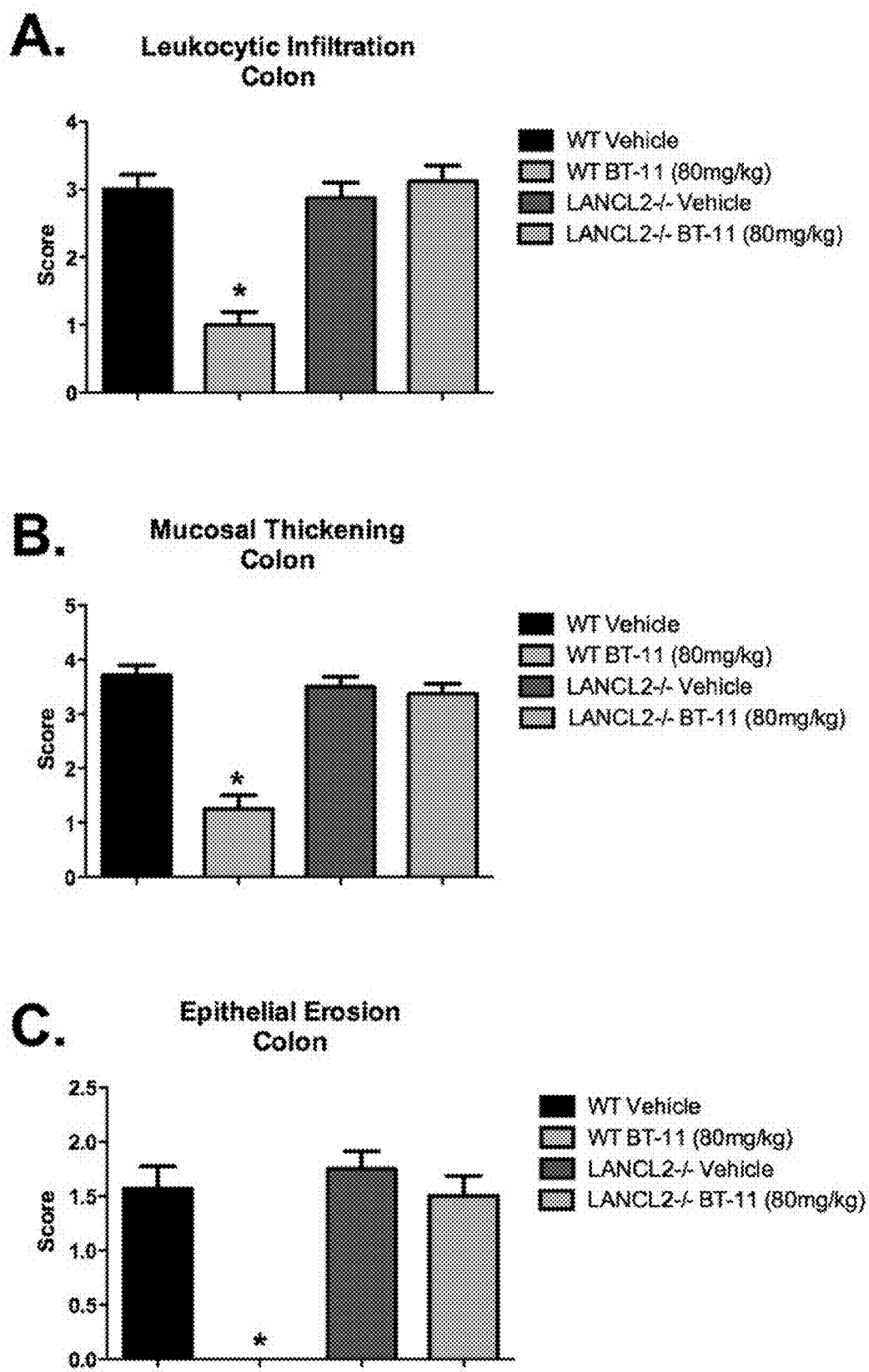
FIG. 16. Effect of oral BT-11 administration on colonic inflammatory lesions in wild-type and LANCL2−/− mice with DSS colitis. Histopathological lesions were evaluated based on (A) leukocytic infiltration, (B) mucosal thickening and (C) epithelial erosion. Statistically significant differences between groups (P<0.05) are indicated with an asterisk.

The effects of BT-11 during acute colitis are dependent on LANCL2. In order to demonstrate how the beneficial effects of administration with BT-11 are exerted during acute colitis in mice, we performed studies comparing such effects in wild-type and LANCL2 knock-out (LANCL2−/−) mice. Our results demonstrate that LANCL2 is necessary for BT-11 to exert its anti-inflammatory benefits, as the loss of LANCL2 prevented the mice to recover from acute DSS-induced colitis (FIG. 15, panel A). Likewise, the loss of LANCL2 abrogated the decrease in macroscopic score in the colon (FIG. 15, panel B), the MLN (FIG. 15, panel C), and the spleen (FIG. 15, panel D) when comparing wild-type and LANCL2−/− littermates. Furthermore, the effect of BT-11 in lesion formation in the colonic mucosa is also LANCL2-dependent, as we assessed histopathological analyses in LANCL2−/− mice treated with either vehicle or BT-11 and we observed how the loss of LANCL2 completely abrogates the effect of BT-11 (FIG. 16).

Figure 17:
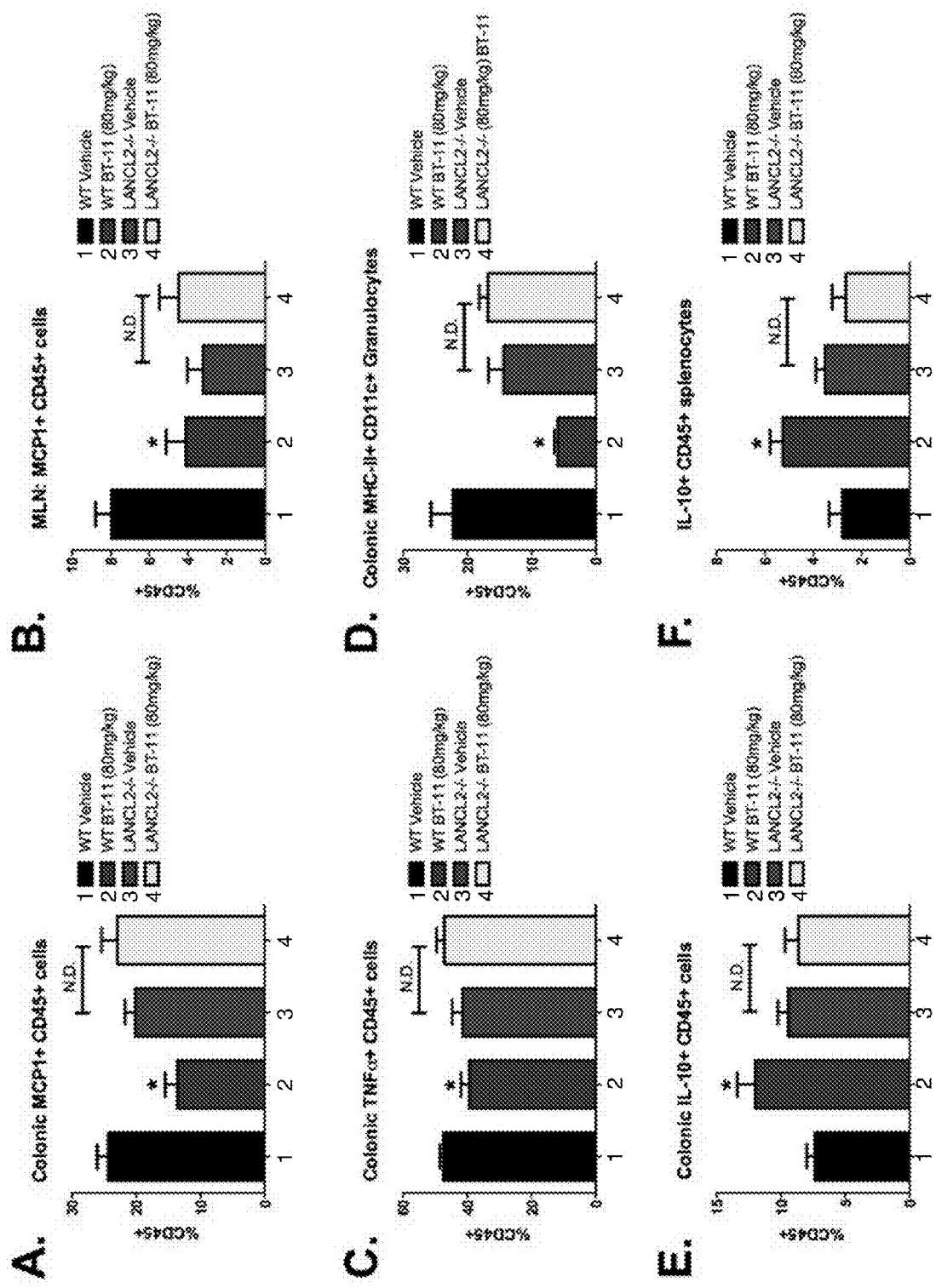
FIG. 17. Effect of oral BT-11 administration on immune cell subsets infiltrating the colonic lamina propria, spleen and mesenteric lymph nodes (MLN) of wild-type and LANCL2−/− mice with chronic colitis. Flow cytometry was used to assay the levels of (A) colonic MCP1+ CD45+ cells, (B) MCP1+ CD45+ cells in the MLN, (C) colonic TNFa+ CD45+ cells, (D) colonic MHC-II+ CD11c+ granulocytes, (E) colonic IL-10+ CD45+ cells, and (F) IL-10+ CD45+ splenocytes after treatment with BT-11. Statistically significant differences between groups (P<0.05) are indicated with an asterisk.

To further characterize the cellular responses following treatment with BT-11, we performed further LANCL2 knockout studies to determine if the decrease of pro-inflammatory proteins and the increase of anti-inflammatory factors were ablated. Our flow cytometry results demonstrate that the reduction of the pro-inflammatory factor MCP1 is LANCL2-dependent in both the colon (FIG. 17, panel A) and the MLN (FIG. 17, panel B), since the loss of the LANCL2 gene abrogates the effect of BT-11. We also found that the secretion of TNFα in the colon is LANCL2-dependent (FIG. 17, panel C) as well as the upregulation of MHC-II+ CD11c+ populations of granulocytes (FIG. 17, panel B). In line with these results, we found that the upregulation of IL-10 secretion after BT-11 treatment is completely abrogated in LANCL2 knockout mice in both the colon (FIG. 17, panel E) and the spleen (FIG. 17, panel F), showing, once again, the dependency of our top lead compound with our target of interest.

Discussion

LANCL2 has emerged as a novel therapeutic target for inflammatory and immune-mediated diseases [18]. Our in vivo results demonstrate for the first time that oral treatment with LANCL2 ligand BT-11 ameliorates gut immunopathology in mouse models of IBD by suppressing inflammation. LANCL2 has received some recent attention as a potential therapeutic target due to its function related to ABA binding and signaling [19] and the recent discovery of an alternative membrane-based mechanism of PPAR γ activation [8]. Furthermore, we determined the LANCL2 expression in a series of mouse tissues, which showed that beside brain and testis, LANCL2 is also expressed in other tissues, such as thymus, spleen, colon, and Peyer's patches, which indicates the possible relationship between LANCL2 and immune responses and suggest the broader potential of LANCL2 as a therapeutic target.

Previously, we have reported that ABA transactivates PPARγ in vitro and suppresses systemic inflammation similar to other PPAR γ agonists. Since both ABA and NSC61610 target LANCL2, NSC61610 might also act via PPAR γ activation. Experimental results show that NSC61610 treatment activates PPAR γ in raw macrophages, thereby providing evidence of a potential signaling relationship between LANCL2 and PPAR γ and indicating that NSC61610 might target the LANCL2-PPAR γ axis in vitro. To investigate the importance of LANCL2 in NSC61610-mediated activation of PPAR γ, we determined whether knocking down LANCL2 in raw macrophages by using siRNA impaired or abrogated the effect of NSC61610 on PPAR γ reporter activity. Our findings indicate that knocking down LANCL2 significantly attenuates the effect of NSC61610 on PPAR γ activity [12]. In this example, we demonstrate how the administration of BT-11 exerts anti-inflammatory properties by decreasing not only the score in disease activity index and the macroscopic scores in spleen, MLN, and colon (FIG. 10) but also significantly reducing histopathological lesions (FIG. 11). We demonstrated how these two specific effects were dependent on LANCL2 (FIG. 15 and FIG. 16). We also demonstrated that BT-11 reduces the levels of TNFa and upregulates both LANCL2 and IL-10 (FIG. 13). We also demonstrated that there effects are LANCL2-dependent as we did not observe these trends in LANCL2-/- mice (FIG. 17). These results confirm that LANCL2 is a novel therapeutic target for inflammatory diseases and BT-11 is a compound that targets it.

Example 21

Use of BT-11 on a Chronic Model of Crohn's Disease

Introduction

As stated above, inflammatory bowel disease (IBD), with its two clinical manifestations, ulcerative colitis and Crohn's disease, is an immune-mediated disease characterized by widespread inflammation and immune cell infiltration of the gastrointestinal tract. The etiology of IBD is multifactorial, and entails interaction among genetic predisposition, environmental factors, and the gut microbiota.

The present example will focus on the chronic manifestation of IBD: Crohn's disease. Whereas the inflammation in ulcerative colitis is characterized by a continuous pattern that involves the superficial mucosal and submucosal layers but is limited to the colon, in Crohn disease this inflammation is transmural and discontinuous, and any region of the gut can be affected beyond the ileum, which is most affected. Crohn's disease pathogenesis is complex and influenced by genetic and environmental factors and immune-mediated injury to the gut mucosa brought about by prolonged activation of the mucosal immune system.

Treatments targeted to downmodulate the immune and inflammatory responses, such as the corticosteroid prednisone or the anti-tumor necrosis factor-α antibody REMICADE® (Janssen Biotech, Inc., Horsham, Pa.) (infliximab), have shown promise in reducing severity and reoccurrence of the disease. These treatments, however, are also associated with various adverse side effects, such as cushingoid appearance, weight gain, and systemic immunosuppression, thus stressing the need to develop safer alternatives for the long-term management of IBD [20].

The present invention provides a novel drug product for the treatment of Crohn's disease by targeting a novel receptor named LANCL2. BT-11, an exemplary compound, is administered orally and distributed systemically, and exerts immune modulatory effects in not only UC but also Crohn's disease by targeting LANCL2 in gut immune cells. Our pre-clinical efficacy studies in chronic models of Crohn's disease in mice showed how administration with BT-11 reduces the disease activity index and improves gut inflammation by significantly decreasing leukocytic infiltration in the gut mucosa, as well as decreasing mucosal thickening and epithelial erosion. Gene expression analyses confirmed that oral administration of BT-11 upregulates the expression of LANCL2, and downregulates the expression of TNFα mRNA in a chronic model of IBD in mice. Furthermore, the administration of BT-11 reduces proinflammatory macrophages and dendritic cell infiltration into the colonic lamina propria as well as upregulated FOXP3-expressing CD4+ T cells and downregulated the number of effector Th1 cells in the colon. We also performed knock-out studies to confirm that these effects are LANCL2-dependent. Finally, in the induction sites, BT-11 is capable of downregulating the generation of Th17 cells as well as upregulating the regulatory CD4+ T cell compartment via upregulation of FOXP3 expression.

Methods

Mice. C57BL/6 and IL-10 knockout mice were purchased from the Jackson Laboratory and housed under specific pathogen-free conditions in ventilated racks. LANCL2-/- mice were purchased from the KOMP repository at University of California Davis. All mice were maintained in animal facilities. All experimental protocols were approved by an institutional animal care and use committee and met or exceeded guidelines of the National Institutes of Health Office of Laboratory Animal Welfare and Public Health Service policy.

CD4+ T cell enrichment and sorting. Splenocytes obtained from C57BL/6J (wild-type) mice were enriched in CD4+ T cells by magnetic negative sorting using the I-Mag cell separation system (BD Pharmingen). Cells were incubated with a mixture of biotinylated Abs followed by a second incubation with streptavidin particles and exposed to a magnet to remove unwanted cells. The purity of the CD4+-enriched cell suspension was between 93 and 96%. CD4-enriched cells were used for adoptive transfer, or further purified by FACS. For FACS sorting, cells were labeled with CD45RB, CD4, and CD25 and separated into CD4+ CD45RBhigh CD25-cells (i.e., effector T cells) in a FACSARIA™ cell sorter (BD Biosciences, San Jose, Calif.). The purity of the FACS-sorted CD4+ subsets was ≥98%.

Adoptive transfer. Six-week-old SCID and RAG2-/- mice were administered intraperitoneally (i.p.) $4 \times 10^5$ CD4+ CD45RBhigh CD25- from C57BL/6J (wild-type) or LANCL2-/- mice. Mice were weighed on a weekly basis and clinical signs of disease were recorded daily for 14 wk. Mice that developed severe signs of wasting disease were sacrificed. Otherwise, mice were sacrificed 90 days after transfer. The groups for adoptive transfer studies went as follows: i. non-transferred vehicle treated, ii. Non-transferred BT-11 (80 mg/Kg) treated, iii. Transferred vehicle treated, iv. Transferred BT-11 (80 mg/Kg) treated. 12 mice were used in each group.

Histopathology. Colonic sections from IBD studies in mice were fixed in 10% buffered neutral formalin, later embedded in paraffin and then sectioned (5 μm) and stained with H&E stain for histological examination. Colons were graded with a compounded histological score including the extent of (1) leukocyte infiltration, (2) mucosal thickening and (3) epithelial cell erosion. The sections were graded with a score of 0-4 for each of the previous categories, and data were analyzed as a normalized compounded score.

Cell Isolation. Spleens and mesenteric lymph nodes (MLN) were excised and crushed in 1× PBS/5% FBS using the frosted ends of two sterile microscope slides. Single cell suspensions were centrifuged at 300× g for 10 min and washed once with 1× PBS. Red blood cells were removed by osmotic lysis prior to the washing step. All cell pellets were resuspended in FACS buffer (1× PBS supplemented with 5% FBS and 0.09% sodium azide) and subjected to flow cytometric analysis. Paralelly, colons were excised and lamina propria leukocytes (LPL) were isolated. Tissue pieces were washed in CMF (1× HBSS/10% FBS/25 mM Hepes), and tissue was incubated twice with CMF/5 mM EDTA for 15 min at 37° C. while stirring. After washing with 1× PBS, tissue was further digested in CMF supplemented with 300 U/ml type VIII collagenase and 50 U/ml DNAse I (both Sigma-Aldrich) for 1.5 hs at 37° C. while stirring. After filtering the supernatants, cells were washed once in 1× PBS, pellets were resuspended in FACS buffer and subjected to flow cytometric analysis.

Immunophenotyping and cytokine analysis by flow cytometry. For fluorescent staining of immune cell subsets 4-6×10$^5$ cells were incubated for 20 min with fluorochrome-conjugated primary mouse specific antibodies: anti-CD3 PE-Cy5 clone 145-2C11 (eBioscience, San Diego, Calif.), anti-CD4 PE-Cy7 clone GK1.5 (eBioscience), anti-CD4 APC clone RM4-5 and anti-CD25 Biotin clone 7D4 (BD Biosciences). Cells were washed with FACS buffer (1× PBS supplemented with 5% FBS and 0.09% sodium azide). For intracellular staining of transcription factors and cytokines, cells were fixed and permeabilized using a commercial kit according to the manufacturer's instructions (eBioscience). Briefly, cells were fixed and permeabilized for 20 minutes, Fc receptors were blocked with mouse anti-CD16/CD32 FcBlock (BD Biosciences) and cells were stained with fluorochrome-conjugated antibodies towards anti-mouse, FOXP3 FITC clone FJK-16s, anti-mouse ROR gamma (t) PE, clone B2B and anti-mouse IL17-A APC, clone eBio17B7 (eBioscience). All samples were stored fixed at 4° C. In the dark until acquisition on a FACS Aria flow cytometer (BD Biosciences). A live cell gate (FSC-A, SSC-A) was applied to all samples followed by single cell gating (FSC-H, FSC-W) before cells were analyzed for the expression of specific markers. Data analysis was performed with FACS DIVA™ (BD Biosciences) and Flow Jo (Tree Star Inc.).

Quantitative Real-Time PCR. Total RNA was isolated from mouse colons using a RNEASY PLUS MINI KIT (Qiagen) according to the manufacturer's instructions. Total RNA (1 µg) was used to generate a cDNA template using an ISCRIPT™ cDNA Synthesis kit (Bio-Rad). The total reaction volume was 20 µL, with the reaction incubated as follows in an MJ MINI™ thermal cycler (Bio-Rad): 5 min at 25° C., 30 min. at 52° C., 5 min at 85° C., and hold at 4° C. PCR was performed on the cDNA using Taq DNA polymerase (Invitrogen). Each gene amplicon was purified with the MINELUTE PCR Purification kit (Qiagen) and quantified both on an agarose gel by using a DNA mass ladder (Promega) and with a nanodrop. These purified amplicons were used to optimize real-time PCR conditions and to generate standard curves in the real-time PCR assay. Primers were designed using Oligo 6 software. Primer concentrations and annealing temperatures were optimized for the ICYCLER IQ™ system (Bio-Rad) for each set of primers using the system's gradient protocol. PCR efficiencies were maintained between 92 and 105% and correlation coefficients >0.98 for each primer set during optimization and also during the real-time PCR of sample DNA. cDNA concentrations for genes of interest were examined by real-time qPCR using an ICYCLER IQ™ System and the IQ™ SYBR® Green Supermix (Bio-Rad). A standard curve was generated for each gene using 10-fold dilutions of purified amplicons starting at 5 pg of cDNA and used later to calculate the starting amount of target cDNA in the unknown samples. SYBR® green I is a general double-stranded DNA intercalating dye and may therefore detect nonspecific products and primer/dimers in addition to the amplicon of interest. To determine the number of products synthesized during the real-time PCR, a melting curve analysis was performed on each product. Real-time PCR was used to measure the starting amount of nucleic acid of each unknown sample of cDNA on the same 96-well plate.

Statistical Analysis. Parametric data were analyzed using the ANOVA followed by Scheffe's multiple comparison method. Nonparametric data were analyzed by using the Mann-Whitney's U test followed by a Dunn's multiple comparisons test. ANOVA was performed by using the general linear model procedure of SAS, release 6.0.3 (SAS Institute). Statistical significance was assessed at a $P \leq 0.05$.

Results

Figure 18:
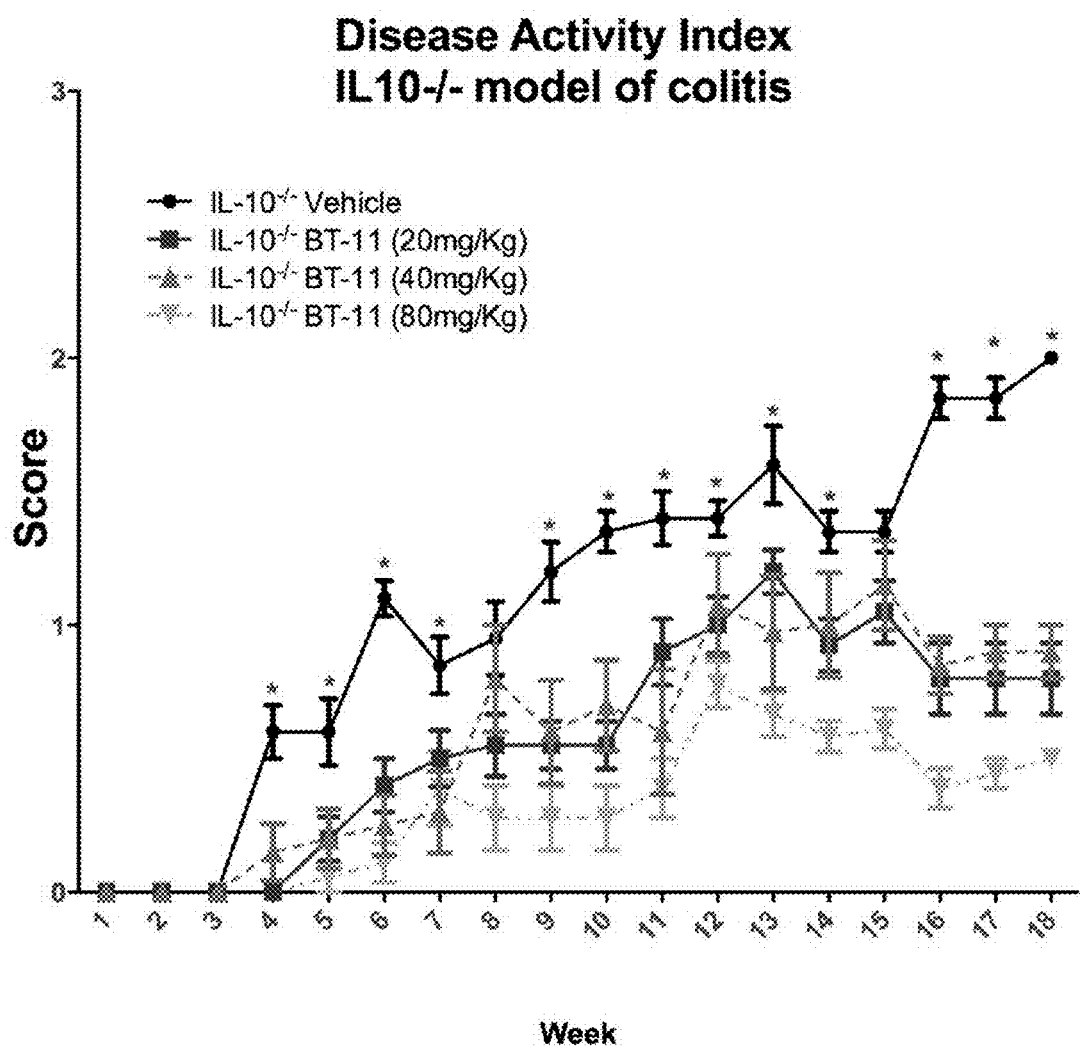
FIG. 18. Effect of oral BT-11 administration on disease activity index (DAI) scores in IL-10−/− mice with chronic colitis. DAI scores on IL-10 null mice that developed spontaneous colitis and that were treated daily with either vehicle alone or with 20, 40, and 80 mg of BT-11/Kg body weight (n=10). Statistically significant differences between groups (P<0.05) are indicated with an asterisk.

BT-11 improves disease activity in a chronic IL-10−/− model of IBD. A number of animal studies to study the chronicity of Crohn's disease have employed the interleukin-10 deficient mice (IL-10−/−) mouse model, given that IL-10 is known to suppresses the secretion of numerous proinflammatory cytokines [21]. To assess the efficacy of BT-11 not only in acute models of colitis but also in chronic models, we set up an IL-11 null mouse model of colitis study and treated the mice with increasing doses of BT-11 (20, 40, and 80 mg/Kg). Treatment with BT-11 significantly decreased the disease activity index scores in treated mice in comparison to their vehicle-treated littermates (FIG. 18). Furthermore, mice treated with the highest dose of BT-11 (80 mg/Kg) significantly reduced the scores in comparison to those treated with either 20 or 40 mg/Kg of BT-11 compound starting at week 13 and until the end of the experiment.

Figure 19:
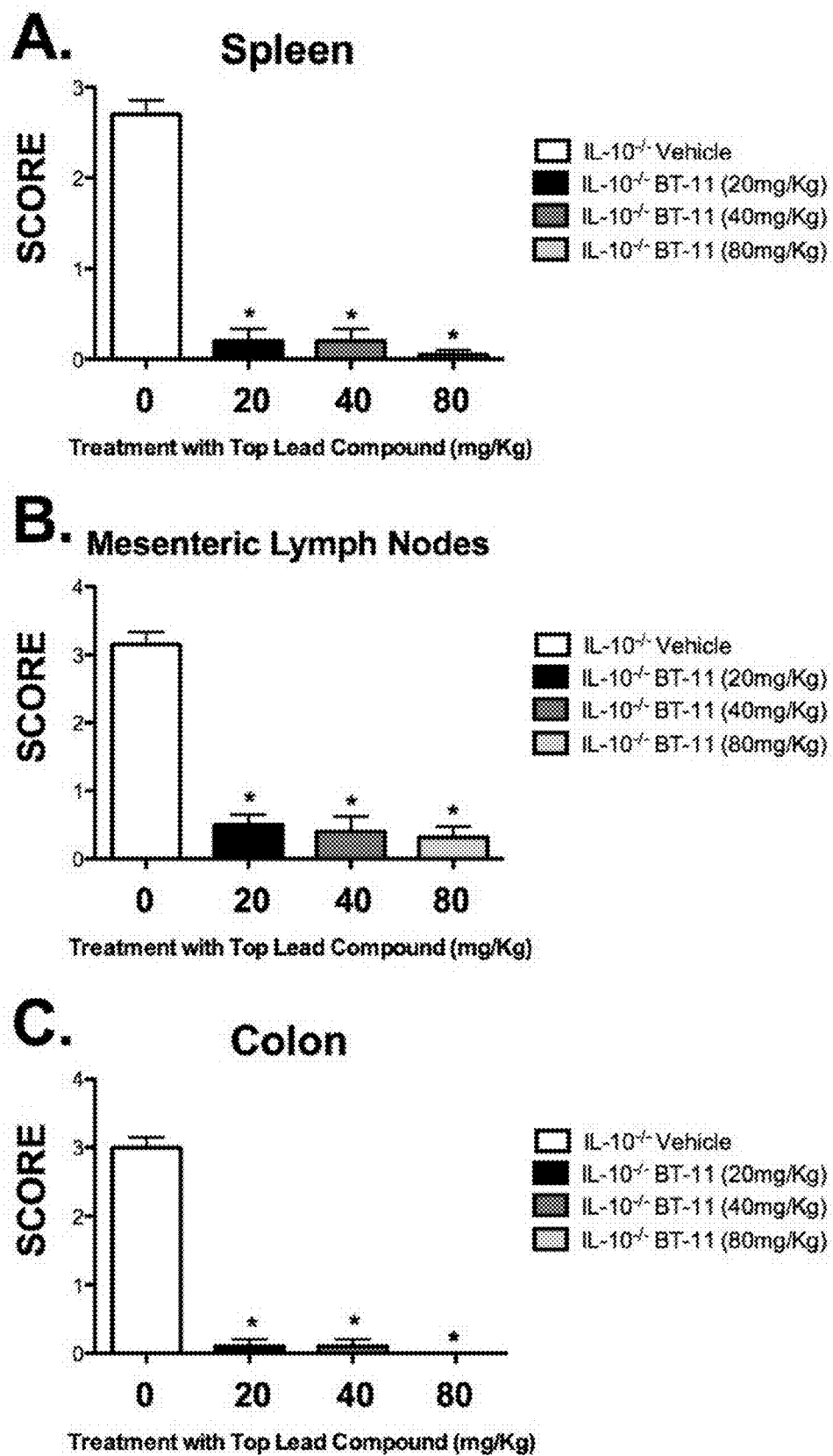
FIG. 19. Effect of oral BT-11 administration on macroscopic tissue scoring in a chronic model of colitis after treatment with BT-11. Macroscopic scores in (A) spleen, (B) mesenteric lymph nodes (MLN), and (C) colon of mice treated with either vehicle or BT-11 at three different concentrations (20, 40, and 80 mg/Kg). Statistically significant differences between groups (P<0.05) are indicated with an asterisk.

BT-11 reduced macroscopic lesions in spleen, MLN, and colon in an IL10−/− chronic model of IBD. To initially determine clinical efficacy we assessed macroscopic tissue lesion after treatment with BT-11 and subsequent LANCL2 pathway activation. We macroscopically scored the spleen (FIG. 19, panel A), the MLNs (FIG. 19, panel B), and the colon (FIG. 19, panel C) right after euthanasia and tissue collection 19 weeks after the start of the study. Treatment with BT-11 at concentrations as low as 20 mg/Kg greatly and significantly reduced the macroscopic scores in the three tissues demonstrating its potent efficacy.

Figure 20:
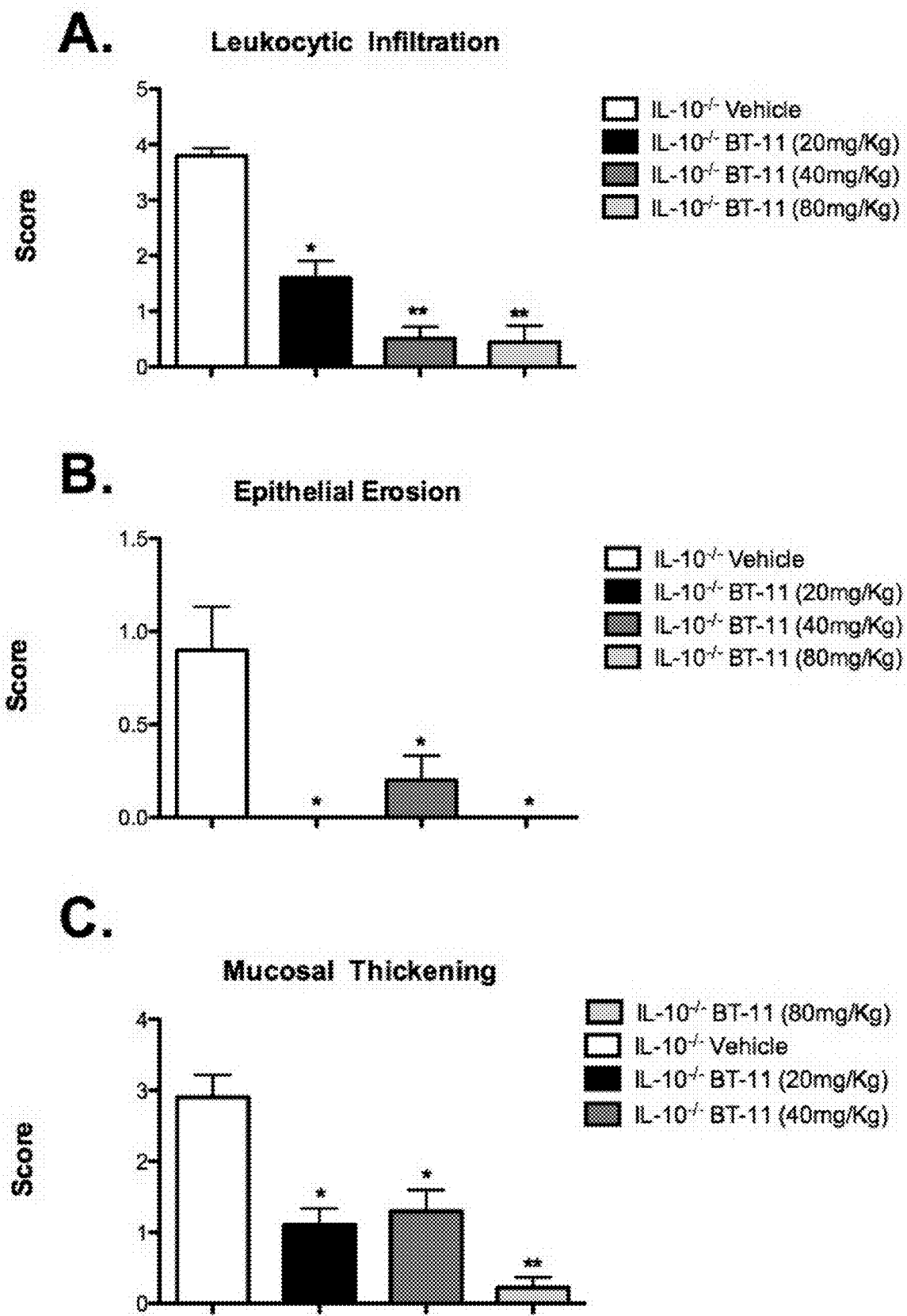
FIG. 20. Effect of oral BT-11 administration on colonic histopathological lesions in chronic IL-10−/− model of IBD. Histopathological lesions were evaluated based on (A) leukocytic infiltration, (B) epithelial erosion, and (C) mucosal thickening. Statistically significant differences between groups (P<0.05) are indicated with an asterisk.

BT-11 improves histopathological lesions and inflammation in a IL-10−/− chronic model of IBD. To assess histopathological lesions and general pathology in the gut mucosa, colon sections were stained with H&E and observed under a microscope. Our results show how treatment with BT-11 significantly reduced inflammation based on the reduction of leukocytic infiltration (FIG. 20, panel A), epithelial erosion (FIG. 20, panel B), and mucosal thickening (FIG. 20, panel C). We also observed a dose-dependent mechanism on the amount of infiltration in the gut mucosa that correlated to the thickening of the mucosa.

Figure 21:
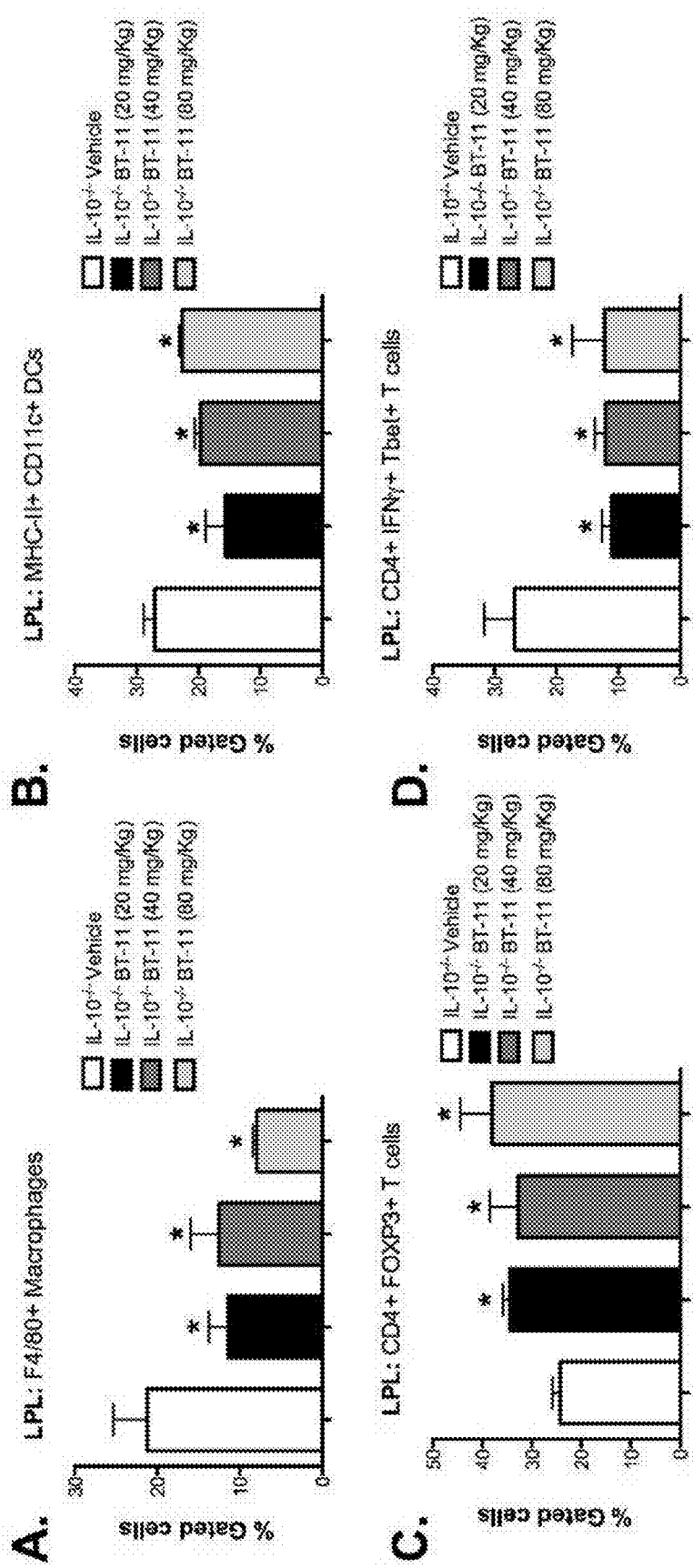
FIG. 21. Effect of oral BT-11 administration on immune cell subsets infiltrating the colonic lamina propria of IL-10−/− with chronic colitis. Flow cytometry was used to assay the levels of (A) F4/80+ macrophages, (B) MHC-II+ CD11c+ dendritic cells (DC), (C) CD4+ FOXP3+ regulatory T cells, and (D) T helper 1 (Th1) cells in the colonic LP after treatment with BT-11. Statistically significant differences between groups (P<0.05) are indicated with an asterisk.

Treatment with BT-11 induces a potent anti-inflammatory response and decreases pro-inflammatory subsets in the colonic lamina propria, spleen, and MLN. To determine the effect of BT-11 on immune cell subsets, we phenotypically characterized cells isolated from the colon, spleen, and MLN. Our analyses indicated that BT-11 significantly decreased the percentage of pro-inflammatory F4/80+ macrophages (FIG. 21, panel A), MHC-II+ CD11c+ dendritic cells (FIG. 21, panel B), and effector Th1 cells (FIG. 21, panel D) in the colonic lamina propria. Furthermore, BT-11 exerted anti-inflammatory properties via the upregulation of FOXP3-expressing CD4+ T cells in the colonic LP (FIG. 21, panel C).

Figure 22:
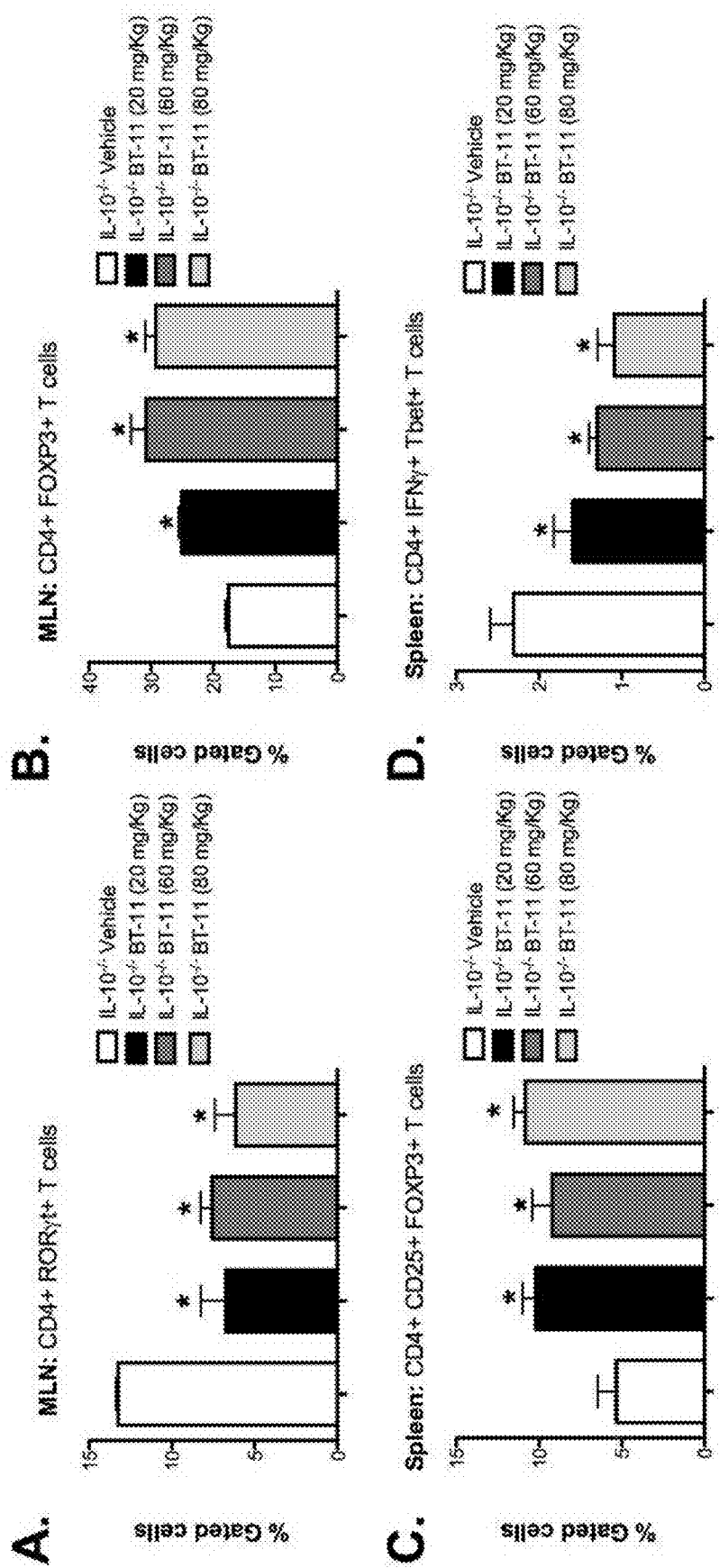
FIG. 22. Effect of oral BT-11 administration on immune cell subsets infiltrating the spleen and mesenteric lymph nodes of IL-10−/− with chronic colitis. Flow cytometry was used to assay the levels of (A) CD4+ RORgt+ T cells, (B) CD4+ FOXP3+ cells, (C) CD4+ CD45+ FOXP3+ regulatory T cells, and (D) T helper 1 (Th1) cells after treatment with BT -11. Statistically significant differences between groups (P<0.05) are indicated with an asterisk.

The upregulation of FOXP3-expressing CD4+ T cells was also noted in both the MLN (FIG. 22, panel B) and the spleen (FIG. 22, panel C), showing and demonstrating how BT-11 has a systemic effect as well. The downregulation of pro-inflammatory Th1 cells was also observed in the spleen in a dose response manner (FIG. 22, panel D). Last, effector Th17 cells, characterized by its expression of RORγt, were downregulated in the MLN (FIG. 22, panel A).

Figure 23:
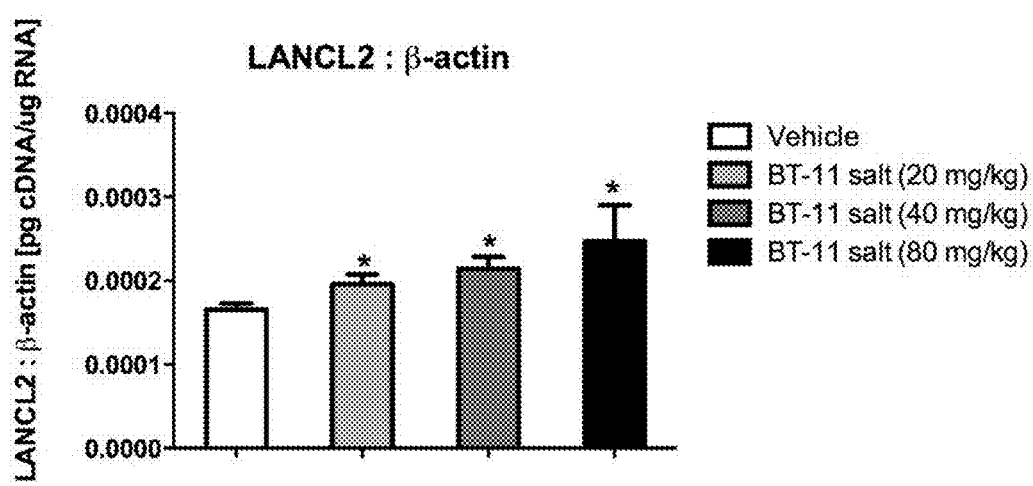
FIG. 23. Effect of oral treatment with BT-11 on colonic expression of LANCL2 and TNFα. Colonic gene expression was used to assess the levels of (A) LANCL2 and (B) TNFα. Statistically significant differences between groups (P<0.05) are indicated with an asterisk.
Figure 23:
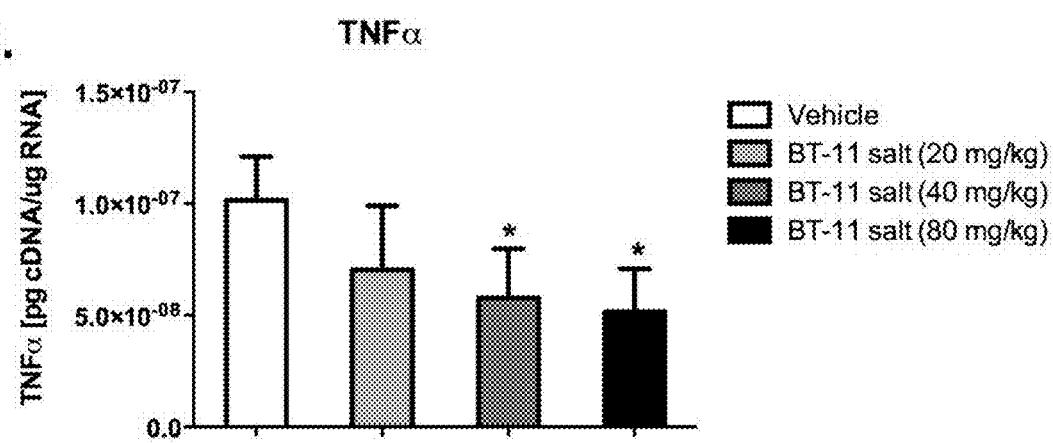

Furthermore, gene expression analyses confirmed that treatment with BT-11 upregulates colonic expression of LANCL2 (FIG. 23, panel A) and downregulates the expression of TNFα (FIG. 23, panel B). These expression effects were dose-dependent on the amount of BT-11 administered.

Figure 24:
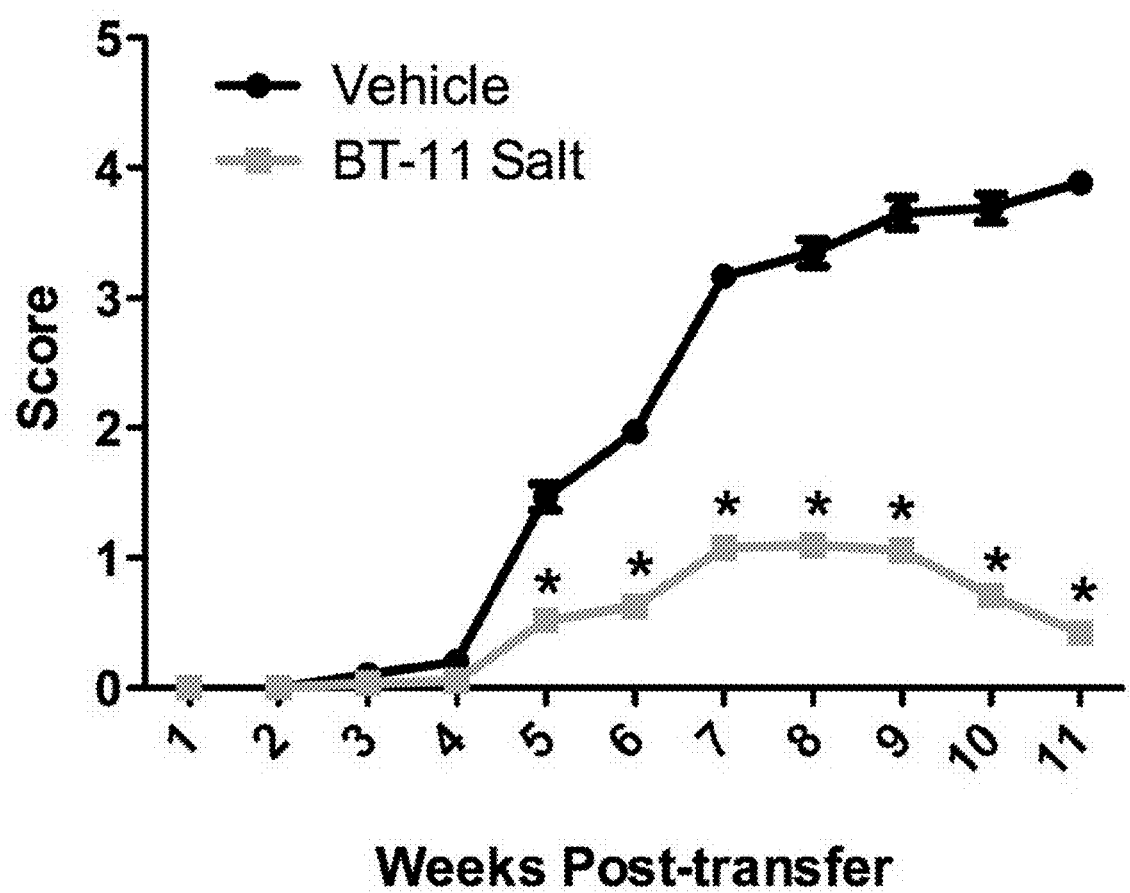
FIG. 24. Effect of oral BT-11 administration on disease activity index scores in vehicle versus treated mice in an adoptive transfer model of chronic colitis. RAG2−/− mice were treated with vehicle or BT-11 following transfer of 400,000 naïve CD4+ T cells intraperitoneally. Statistically significant differences between groups (P<0.05) are indicated with an asterisk.
Figure 25:
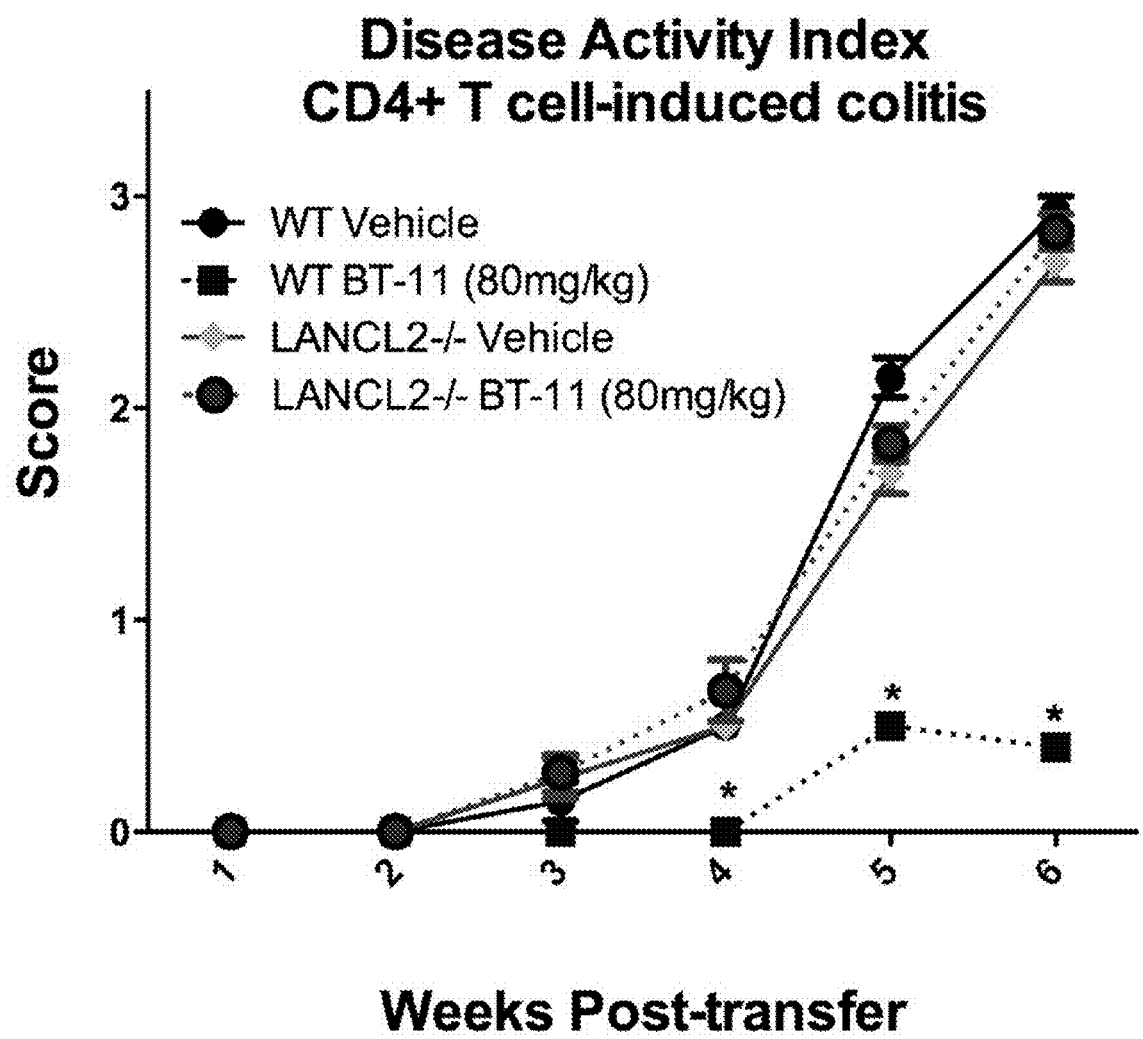
FIG. 25. Effect of oral BT-11 administration on disease activity index scores in vehicle versus treated wild-type versus LANCL2−/− transferred mice in an adoptive transfer model of chronic colitis. RAG2−/− mice were treated with vehicle or BT-11 following transfer of 400,000 naïve CD4+ T cells intraperitoneally from either wild-type or LANCL2−/− donors. Statistically significant differences between groups (P<0.05) are indicated with an asterisk.

BT-11 demonstrated improvement of disease activity in a CD4+ T cell induction of colitis model of IBD. To further validate the efficacy of BT-11 in another chronic model of IBD, we adoptively transferred naïve CD4+ T cells from wild-type and LANCL2−/− mice into RAG2−/− recipients. RAG2−/− mice were treated with either vehicle or BT-11 based on experimental design. Treatment with our top lead compounds BT-11 significantly reduced the disease activity index score in treated mice when compared to their wild-type littermates (FIG. 24). We found these results to be LANCL2-dependent as the effect of BT-11 was completely abrogated with the loss of LANCL2 (FIG. 25).

Figure 26:
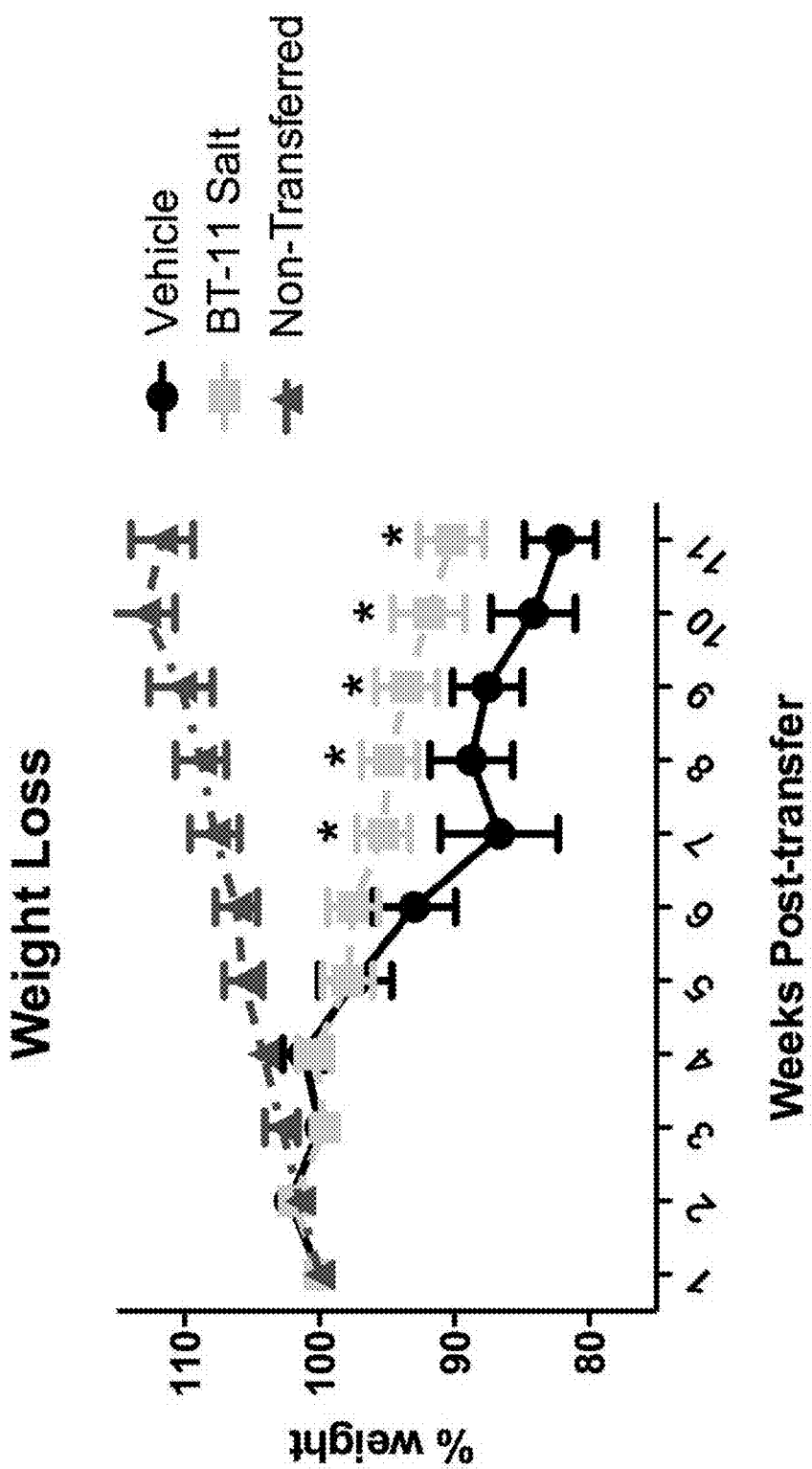
FIG. 26. Effect of oral BT-11 administration on weight loss in the chronic IBD model of CD4+ -induced colitis. Mice were weighed and percentage of weight loss was calculated. Statistically significant differences between groups (P<0.05) are indicated with an asterisk.

Interestingly, the weight loss in BT-11 treated mice was significantly improved when compared to vehicle treated mice starting at 7 weeks until the end of the experiment (FIG. 26).

Figure 27:
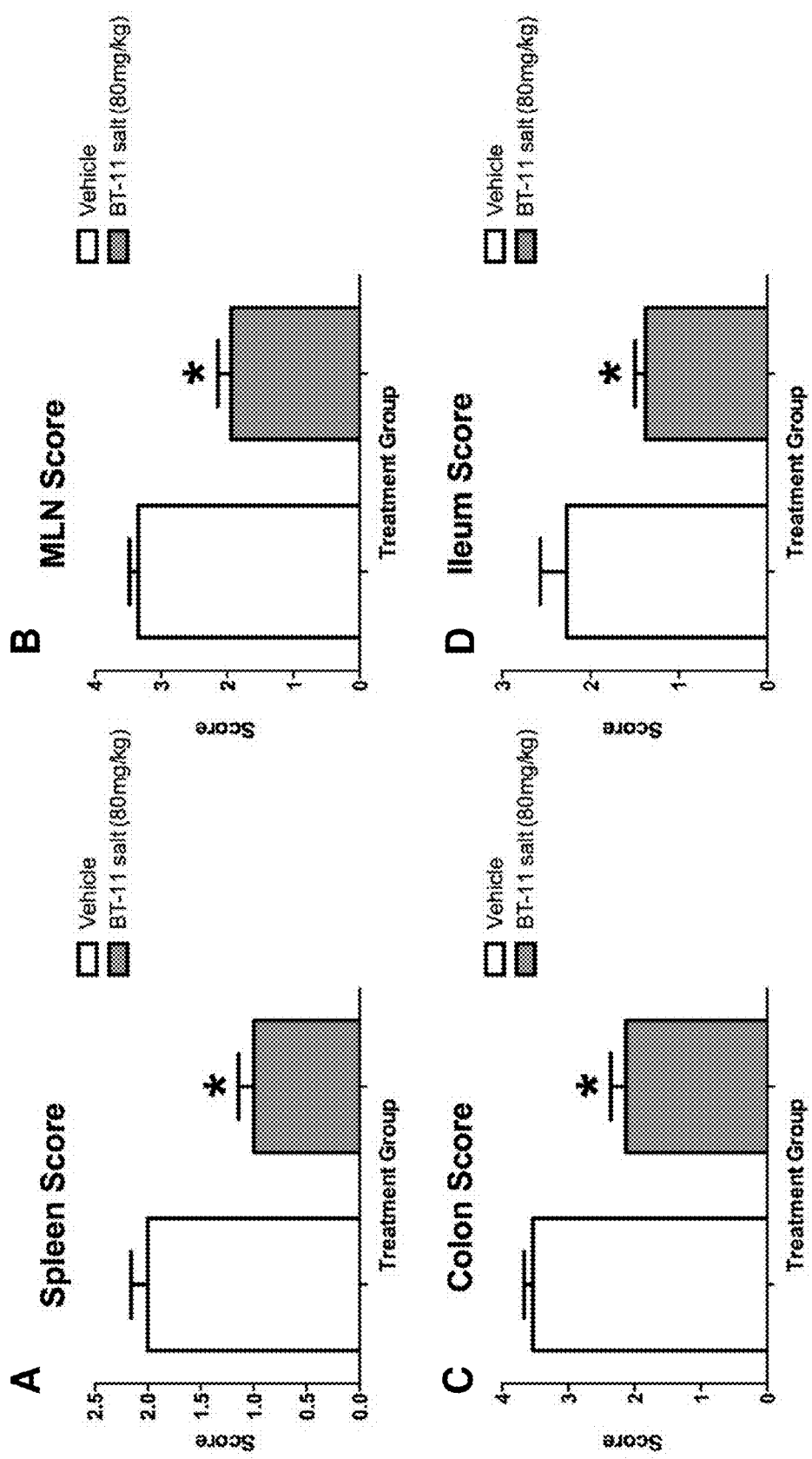
FIG. 27. Effect of oral BT-11 administration on macroscopic tissue scoring in a chronic model of CD4+ T cell-induced colitis after treatment with BT-11. Macroscopic scores in (A) spleen, (B) MLN, (C) colon, and (D) ileum of mice treated with either vehicle or BT-11 at 80 mg/Kg are shown. Statistically significant differences between groups (P<0.05) are indicated with an asterisk.
Figure 28:
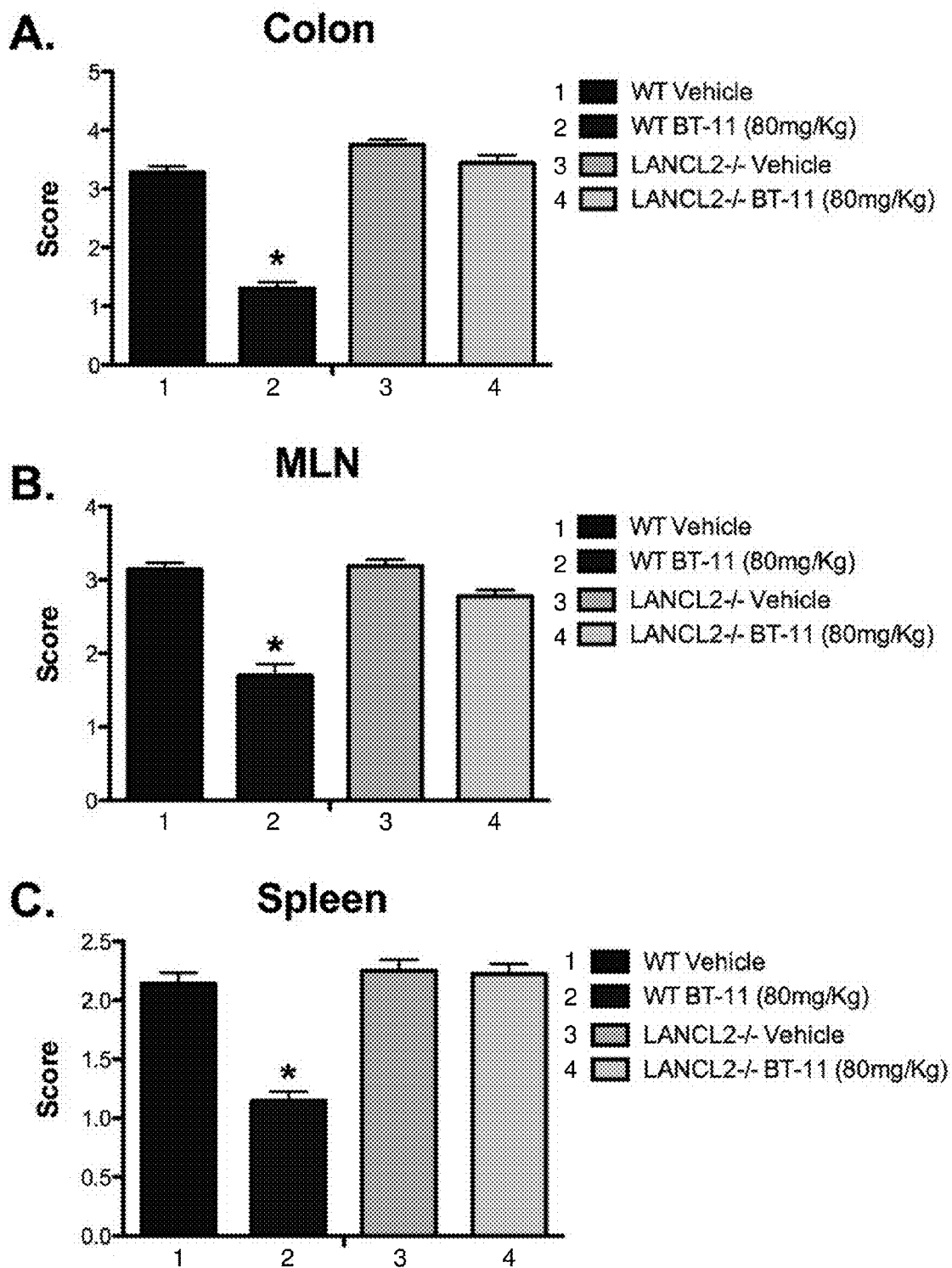
FIG. 28. Effect of oral BT-11 administration on macroscopic tissue scoring in a chronic model of CD4+ T cell-induced colitis with wild-type and LANCL2−/− mice after treatment with BT-11. Macroscopic scores in (A) colon, (B) MLN, and (C) spleen of wild-type and LANCL2−/− mice treated with either vehicle or BT-11 at 80 mg/Kg are shown. Statistically significant differences between groups (P<0.05) are indicated with an asterisk.

BT-11 reduced macroscopic lesions in spleen, MLN, and colon in an adoptive transfer chronic model of IBD. To confirm the clinical efficacy in the second model of chronic colitis we assessed macroscopic tissue lesion after treatment with BT-11 and subsequent LANCL2 pathway activation in mice adoptively transferred with wild-type or LANCL2−/− cells and treated with either vehicle or BT-11. We macroscopically scored the spleen (FIG. 27, panel A), the MLNs (FIG. 27, panel B), and the colon (FIG. 27, panel C) and the ileum (FIG. 27, panel D) right after euthanasia and tissue collection 11 weeks after the start of the study. Treatment with BT-11 at a concentration of 80 mg/Kg greatly and significantly reduced the macroscopic scores in the four tissues demonstrating its potent efficacy. We found these observations to be LANCL2-dependent as well as the loss of LANCL2 completely abrogated the effect of BT-11 (FIG. 28).

Figure 29:
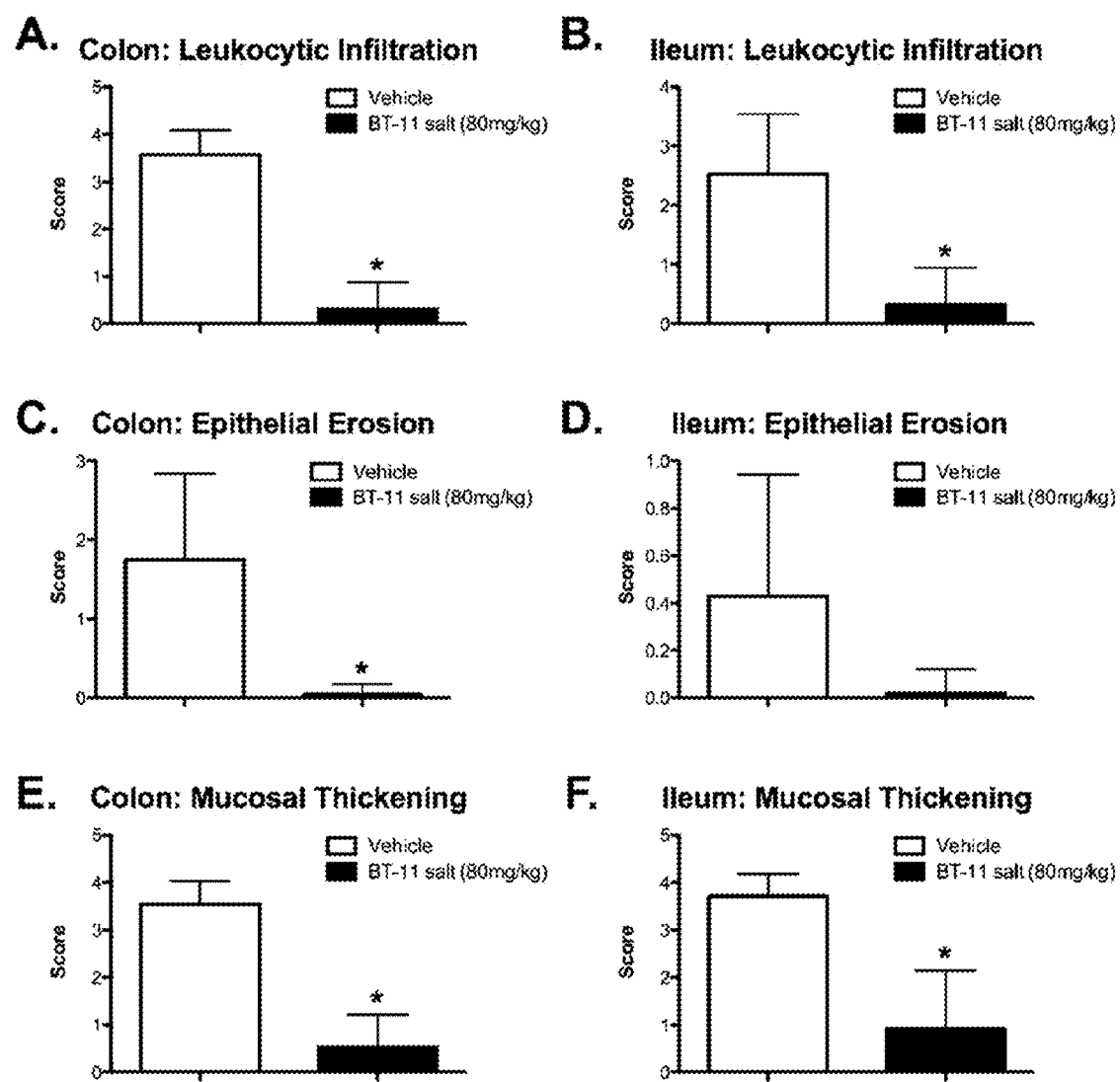
FIG. 29. Effect of oral BT-11 administration on colonic and ileal histopathology in vehicle versus treated mice in an adoptive transfer model of chronic colitis. Histopathological lesions in the colon (A, C, E) and ileum (B, D, F) were evaluated based on (A, B) leukocytic infiltration, (C, D) epithelial erosion, and (E, F) mucosal thickening. Statistically significant differences between groups (P<0.05) are indicated with an asterisk.
Figure 30:
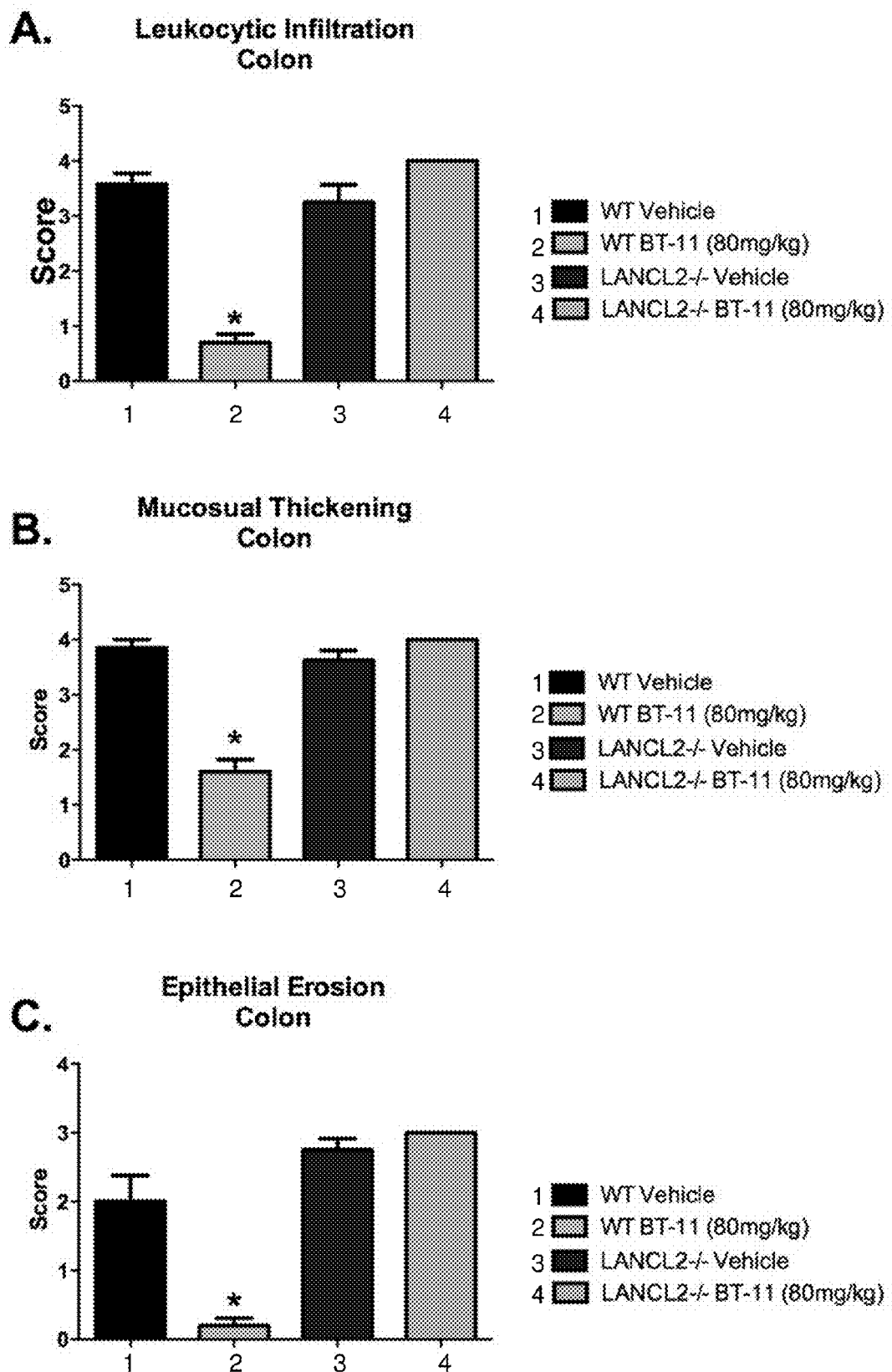
FIG. 30. Effect of oral BT-11 administration on colonic histopathology in vehicle versus treated mice transferred with either wild-type or LANCL2-/- CD4+ T cells in an adoptive transfer model of chronic colitis. Histopathological lesions were evaluated based on (A) leukocytic infiltration, (B) mucosal thickening, and (C) epithelial erosion. Statistically significant differences between groups (P<0.05) are indicated with an asterisk.

BT-11 also improves histopathological lesions and inflammation in an adoptive transfer model of chronic colitis. Similar to the IL-10−/− induced colitis experiment and to confirm histopathological lesions and general pathology in the gut mucosa with a second mouse model of IBD, colon sections were stained with H&E and observed under a microscope. Our results confirm how treatment with BT-11 significantly reduced inflammation based on the reduction of leukocytic infiltration in both the colon and ileum (FIG. 29, panels A and B) and mucosal thickening (FIG. 29, panels E and F). Of note, the ileum was less affected on epithelial erosion (FIG. 29, panel D) but that erosion in the colon was found significantly lower in mice treated with our top lead compound BT-11 (FIG. 29, panel C). To confirm the dependency to LANCL2 of BT-11, we performed adoptive transfer studies and transferred CD4+ T cells from LANCL2−/− donors. Our results show how the decrease in leukocytic infiltration, epithelial erosion, and mucosal thickening are greatly abrogated in LANCL2−/− transferred recipients (FIG. 30).

Figure 31:
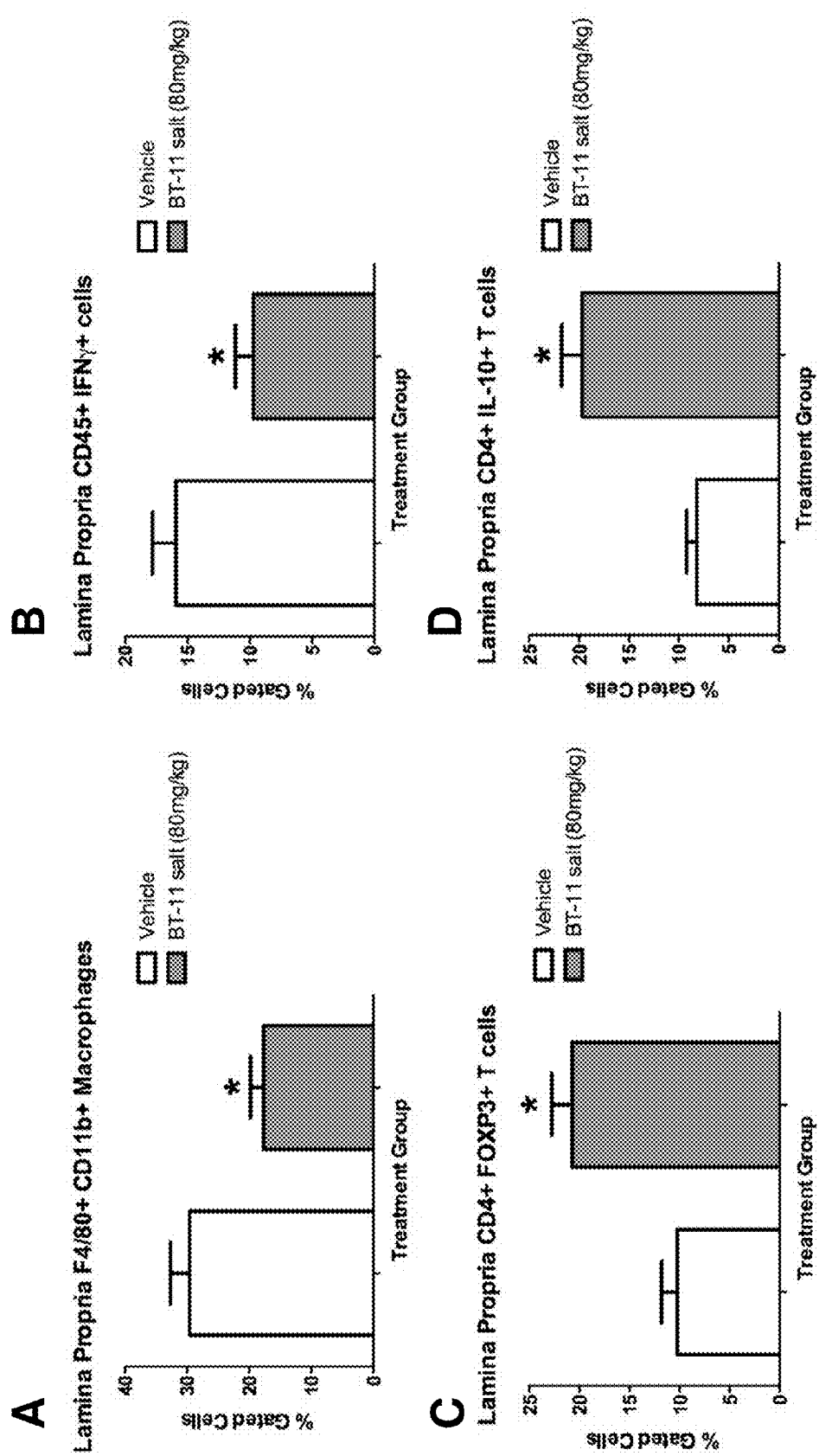
FIG. 31. Effect of oral BT-11 administration on disease activity index scores in vehicle versus treated mice in an adoptive transfer model of chronic colitis. Flow cytometry was used to assay the levels of (A) F4/80+CD11b+ macrophages, (B) CD45+ IFNg+ cells, (C) CD4+ FOXP3+ regulatory T cells, and (D) CD4+ IL-10+ anti-inflammatory cells after treatment with BT-11. Statistically significant differences between groups (P<0.05) are indicated with an asterisk.

BT-11 consistently induces a tremendous anti-inflammatory response and down-regulates pro-inflammatory mediators in mice. To characterize the immune cell profile in mice treated with BT-11 versus vehicle, we performed flow cytometry analyses in cells isolated from the colon, the spleen, and the mesenteric lymph nodes. We confirmed in a second chronic mouse model of IBD that recipient mice that were treated with BT-11 for a period of 11 weeks possess a significantly lower level of infiltrating F4/80+ CD11b+ pro-inflammatory macrophages (FIG. 31, panel A), as well as a decrease in IFNγ levels based on an analysis made on total CD45+ leukocytes (FIG. 31, panel B) in the colon. Furthermore, treatment with BT-11 consistently upregulated regulatory CD4+ T cells by promoting the expression of FOXP3 (FIG. 31, panel C) and the potent anti-inflammatory cytokine (FIG. 31, panel D) at the local site of inflammation, in this case, the colonic mucosa.

Figure 32:
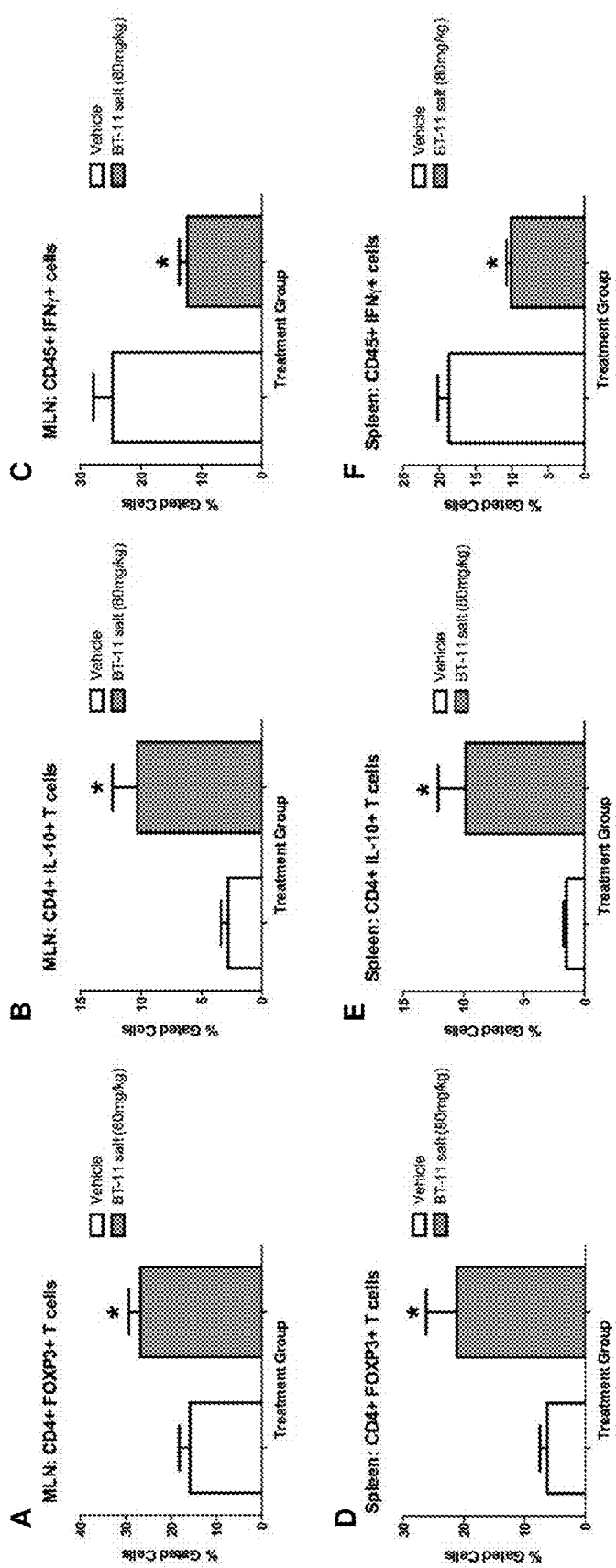
FIG. 32. Effect of oral BT-11 administration on disease activity index scores in vehicle versus treated mice in an adoptive transfer model of chronic colitis. Flow cytometry was used to assay the levels of (A) CD4+ FOXP3+ T cells, (B) CD4+ IL-10+ T cells, (C) CD45+ IFNg+ cells in the MLN, and (D) CD4+ FOXP3+ T cells, (E) CD4+ IL-10+ T cells, (F) CD45+ IFNg+ cells in the spleen after treatment with BT-11. Statistically significant differences between groups (P<0.05) are indicated with an asterisk.

Similar to the profile observed in the colonic lamina propria cells, we characterized these populations in inductive sites such as the spleen and the MLN. Immuno-phenotyping results show how treatment with BT-11 also increases the levels of FOXP3 and IL-10 in the inductive sites such as spleen and MLN (FIG. 32, panels A, B, D, and E). Of note, the treatment of BT-11 decreased the expression of IFNγ in the CD45+ population in both the MLN and the spleen (FIG. 32, panels C and F).

Figure 33:
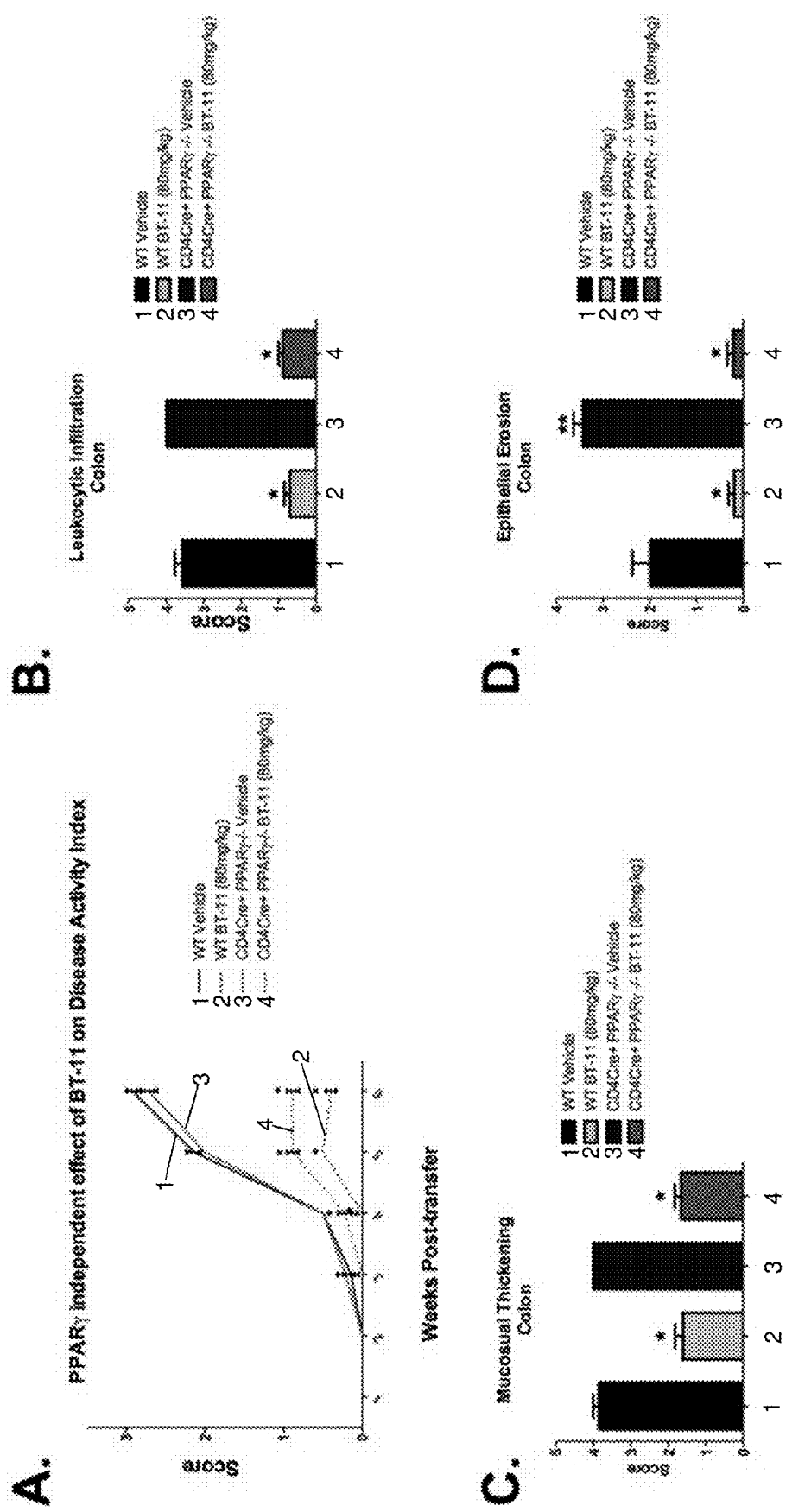
FIG. 33. Effect of oral BT-11 administration on disease activity index scores in vehicle versus treated wild-type versus PPARγ-/- transferred mice in an adoptive transfer model of chronic colitis. RAG2-/- mice were treated with vehicle or BT-11 following transfer of 400,000 naïve CD4+ T cells intraperitoneally from either wild-type or PPARγ-/- donors. (A) Disease activity index scores versus time post-transfer are shown. Histopathological lesions in the colon were evaluated based on (B) leukocytic infiltration, (C) mucosal thickening, and (D) epithelial erosion. Statistically significant differences between groups (P<0.05) are indicated with an asterisk.

The effect of the LANCL2-targeting BT-11 is independent of PPARγ. The activation of LANCL2 activates a plethora of pathways that ultimately regulate IL-10-based anti-inflammatory responses that regulate inflammation at the systems level, based on our experimental results. One activated downstream pathway of LANCL2 is the PPARγ pathway. To help overcome the potential toxicology concerns on the secondary activation of this nuclear and transcription factor, we also transferred RAG2−/− mice with CD4+ T cells from PPARγ −/− donors. We then treated these mice with either vehicle or BT-11 at 80 mg/Kg. Our results clearly demonstrate that the beneficial effects of BT-11 via activation of LANCL2 on disease activity and histopathology occur in a PPARγ independent manner (FIG. 33, panels A-D). These results demonstrate that the activation of LANCL2 also regulate other pathways that modulate the anti-inflammatory effects of LANCL2 activation.

Discussion

Current therapies against inflammatory bowel disease (IBD) are modestly successful and have significant adverse side effects for the long-term management of the disease [17]. The botanical compound abscisic acid (ABA) exerts potent anti-inflammatory effects in mouse models of colitis [22, 23]. Lanthionine synthetase component C-like protein 2 (LANCL2) is a target for the binding and signaling of ABA [15, 19, 24]. Thus, LANCL2 has emerged as a promising novel therapeutic target against inflammation [18]. Compound 61610, a bis(benzimidazoyl)terephthalanilide (BTT), was identified as binding to LANCL2 with the highest affinity in a library of several million chemicals. In addition, 61610 exerted potent anti-inflammatory effects in mouse models of gut inflammation [25]. A thematic library of 20 61610-derived BTTs were created and BT-11 was identified as a top exemplary compound. BT-11 binds to LANCL2, is orally active, has demonstrated anti-inflammatory efficacy in 3 mouse models of colitis and an outstanding safety profile.

According to the Crohn's and Colitis Foundation of America, IBD afflicts over 1 million people in North America and 4 million worldwide. This widespread and debilitating illness results in decreased quality of life and significant health care-related costs [26]. Average medical expenses for treating a single episode of IBD exceed $55,000 per patient [27] with total expenses exceeding $15 billion annually in the U.S. In addition, indirect expenses include the costs of treating recurrent pancreatitis [28] or other IBD complications such as abscesses, intestinal obstruction, anemia, thromboses, perianal lesions, arthritis, uveitis, iritis, or cutaneous lesions [29]. IBD carries a significant burden to patients, often isolating them socially, affecting family relationships and limiting their professional opportunities [17]. In this regard, patients with IBD have a higher rate of nonparticipation in the labor force; this high rate persists over time [30]. In addition, intestinal inflammation (ulcerative colitis (UC) and Crohn's disease (CD)) increases the risk for developing colon cancer especially at early ages (<30 years of age) [31]. The Global MD Therapeutics Market is expected to reach $4.3 Billion by 2015, according to a new report by Global Industry Analysts.

Even though current treatments for IBD have improved [17, 32], they are only modestly successful for chronically managing the disease and result in significant side effects, including a diminished ability of the immune system to mount protective immune responses against pathogens or malignancies. The treatment options for patients include addressing the symptoms of inflammation. The majority of the pharmacological treatments used on the market today include aminosalicyclates, corticosteroids, immunomodulators, antibiotics, biologics (anti-tumor necrosis factor-alpha antibody). Aminosalicyclates are extremely effective and generally well tolerated. However, patients with recurrences or more moderate diseases may need more aggressive treatment, which includes short-term doses of corticosteriods for a short period to control the symptoms. This type of fast-acting therapy cannot be tolerated for long periods. For maintenance of the condition, immunomodulators are also commonly used in CD and UC, but they have a slow onset of action (3 to 6 months for the full effect). These medications have potentially significant adverse side-effects ranging from pancreatitis, to diabetes, to scarred liver and inflamed lungs. For moderate to severe cases of the disease that have failed management with other therapies, patients will be placed on anti-TNF-α, which is given intravenously in a controlled setting every 6-8 weeks. This extremely costly therapy, although effective, is difficult to access, as skilled personnel and a clinical setting are needed for administration. Further, significant side effects exist such as Cushing's syndrome, mania, insomnia, hypertension, high blood glucose, osteoporosis, malignancies, infections, and avascular necrosis of long bones.

The exemplary compound, BT-11, has shown a tremendously safe toxicology profile. Our efficacy data in chronic models of IBD show how treatment of BT-11 improves disease activity scores in two models of chronic IBD (FIGS. 18 and 24) as well as body weight loss (FIG. 26). Our data demonstrates how these effects are LANCL2 dependent (FIG. 25). Our efficacy data also demonstrates how activation of the LANCL2 pathway by BT-11 promotes an anti-inflammatory response mainly characterized by IL-10-producing and FOXP3-expressing CD4+ T cells (FIGS. 21, 22, 31, and 32), as well as a significant decrease in inflammatory macrophages, dendritic cells, and pro-inflammatory factors such as IFNγ (FIGS. 22, 23, 31, and 32). Moreover, the gene expression analyses confirm these cell-based findings by showing how treatment with BT-11 reduces TNFγ levels in the colon (FIG. 23). All these findings together are responsible for the dramatic LANCL2-dependent improvement in the colonic mucosa in terms of leukocytic infiltration, epithelial erosion, and mucosal thickening in two models of chronic IBD (FIGS. 20, 29, and 30). We have also demonstrated that the effects of BT-11 following binding to LANCL2 are PPARγ independent (FIG. 33). These results confirm that the activation of LANCL2 activates a plethora of downstream activators that regulate inflammation via a PPARγ independent mechanism. Together, these results strongly support the fact that LANCL2 is a novel therapeutic target for inflammatory diseases and BT-11 is useful as a new drug.

Example 22

Use of BT-11 to Treat Type 1 Diabetes (T1D)

Introduction

Diabetes mellitus (DM) also known as simply diabetes, is a group of metabolic diseases in which there are high blood sugar levels over a prolonged period of time. The two types of diabetes are referred to as type 1 and type 2. Former names for these conditions were insulin-dependent and non-insulin-dependent diabetes, or juvenile onset and adult onset diabetes. In T1D the body does not produce insulin. In relation to T2D, T1D is nowhere near as common as T2D. Indeed, approximately 10% of all diabetes cases are type 1. T1D afflicts 3 million Americans. Each year, more than 15,000 children and 15,000 adults are diagnosed with T1D in the U.S. The rate of T1D incidence among children under age 14 is estimated to increase by 3% annually worldwide. T1D patients require insulin injections to stay alive, but they do not cure the disease or prevent its serious side effects.

Current anti-diabetic medications are effective in improving insulin sensitivity, but their chronic administration has significant side effects such as cardiovascular complications, hepatotoxicity, weight gain, fluid retention, and bladder tumors. The lanthionine synthetase component C-like 2 (LANCL2) pathway exerts anti-diabetic actions with no side effects [18]. BT-11 binds to LANCL2, is orally active, has demonstrated anti-diabetic efficacy in mice and an outstanding safety profile.

Methods

Mice. NOD mice were purchased from the Jackson Laboratory and housed under specific pathogen-free conditions in ventilated racks. The mice were maintained in animal facilities. All experimental protocols were approved by an institutional animal care and use committee and met or exceeded guidelines of the National Institutes of Health Office of Laboratory Animal Welfare and Public Health Service policy.

Assessment of body weight and glucose tolerance. All mice were determined to be normoglycemic (fasting blood glucose levels lower than 250 mg/dl) and to have similar weights (20±1.5 g) prior to the start of the study. Mice were weighed on a weekly basis and examined for clinical signs of disease by blinded observers. After a standard 12 h fast, glucose was measured using an ACCU-CHEK® glucometer (Indianapolis, Ind.). Blood was collected via the lateral tail vein and placed onto capillary blood collection tubes.

Histopathology. Pancreatic sections from NOD studies in mice were fixed in 10% buffered neutral formalin, later embedded in paraffin and then sectioned (5 μm) and stained with H&E stain for histological examination. The sections were graded with a score of 0-4, depending on lymphocytic infiltration, cell damage and tissue erosion, and data were analyzed as a normalized compounded score.

Statistical Analysis. Parametric data were analyzed using the ANOVA followed by Scheffe's multiple comparison method. Nonparametric data were analyzed by using the Mann-Whitney's U test followed by a Dunes multiple comparisons test. ANOVA was performed by using the general linear model procedure of SAS, release 6.0.3 (SAS Institute). Statistical significance was assessed at a $P \leq 0.05$.

Results

BT-11 lowers fasting blood glucose levels and increases insulin in a mouse model of type 1 diabetes.

Figure 34:
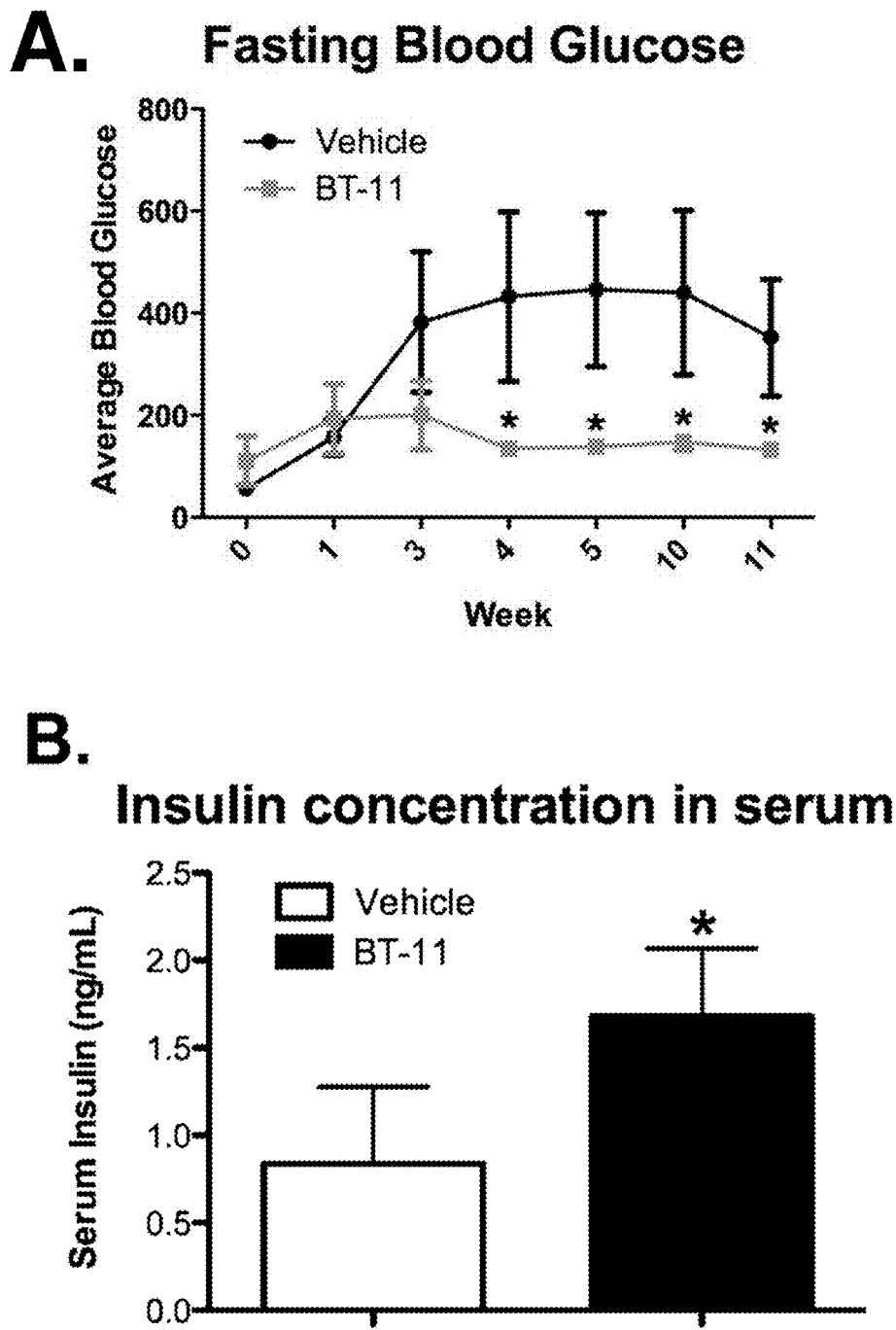
FIG. 34. Effect of oral BT-11 administration on fasting blood glucose and insulin levels in NOD mice with diabetes. (A) Fasting glucose levels were assessed at weeks 0, 1, 3, 4, 5, 10, and 11 of treatment with vehicle or BT-11 (80 mg/kg/d). (B) Fasting serum insulin levels were assessed at week 5 of treatment with either vehicle or BT-11 (80 mg/kg/d). Statistically significant differences (P<0.05) are indicated with an asterisk (n=10).

In order to determine the effect of BT-11 in modulating glycemic levels in a mouse model of T1D, we performed a fasting blood glucose test on weeks 0, 1, 3, 4, 5, 10, and 11 after the start of the study. Our results show how the mice treated with our compound BT-11 had significantly lower levels of glucose in blood after a period of 12 h of fasting (FIG. 34, panel A). In parallel, we assessed insulin levels at week 5 and our results show how mice treated with BT-11 had significantly increased levels of insulin in plasma (FIG. 34, panel B).

Figure 35:
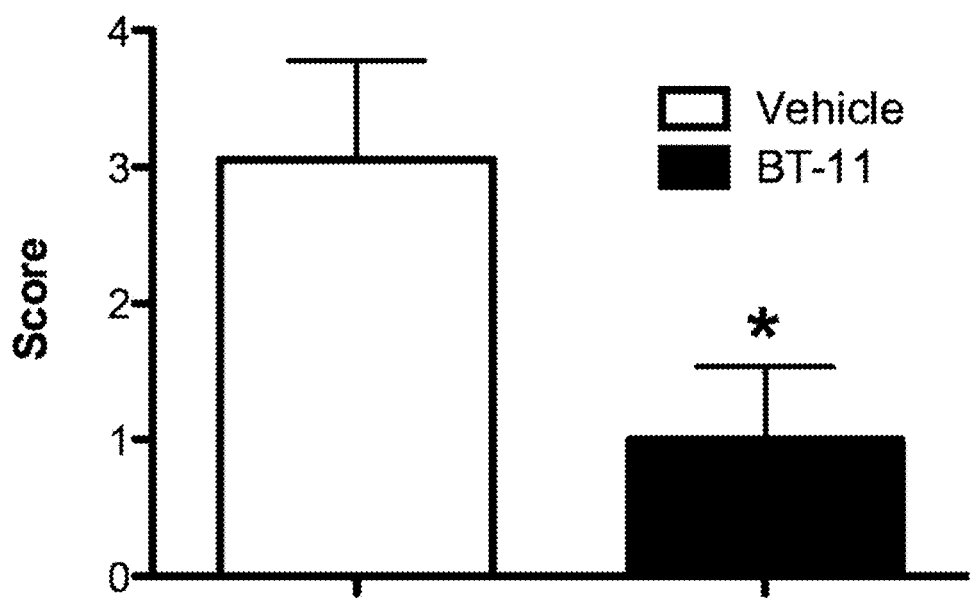
FIG. 35. Effect of oral BT-11 administration in lesion formation in the pancreas of type 1 diabetic mice. Histopathological lesions were evaluated based on leukocytic infiltration, lesion formation, and tissue erosion. Statistically significant differences between groups (P<0.05) are indicated with an asterisk.

BT-11 improves clinical histopathological pancreatic lesions and inflammation in the mouse NOD model. To assess histopathological lesions in the mouse model of T1D, pancreas were collected and fixed with 10% formalin. Pancreatic sections were then stained with H&E and observed under a microscope. Our results show how treatment with BT-11 significantly reduces the clinical histopathological lesions in the pancreas in mice when compared to the vehicle treated mice (FIG. 35).

Discussion

There is a need for efficacious and safer oral medications for Type 1 Diabetes (T1D), a disease that afflicts over 3 million Americans. ABA treatment exerts anti-diabetic effects [2]. Lanthionine synthetase component C-like protein 2 (LANCL2) is a target for the binding and signaling of ABA [15, 19, 24]. Thus, LANCL2 has emerged as a promising novel therapeutic target against inflammation [18]. ABA is efficacious in improving diabetes [2, 33] and immune-mediated diseases such as inflammatory bowel disease (IBD) [22, 23]. Compound 61610, a bis(benzimidazoyl)terephthalanilide (BTT), binds to LANCL2 with the highest affinity in a library of several million chemicals. In addition, 61610 exerted potent immune modulatory effects in mouse models of gut inflammation [25]. BT-1 1 exerts anti-diabetic effects in NOD mice (FIGS. 34 and 35). Moreover, ABA increased insulin secretion in human pancreatic beta-cells [34], suggesting ABA's potential application as the treatment of type 1 diabetes (T1D).

In immune cells, ABA is recognized by LANCL2, a G-protein couple receptor that associates with the cell membrane following myristoylation [19, 35]. ABA binding to LANCL2 increases cAMP and initiates signaling through PKA and modulates immune responses in macrophages and T cells [8]. We performed homology modeling to construct a three-dimensional structure of LANCL2 by using the crystal structure of LANCL1 as a template. Using molecular docking, it was demonstrated first in silico and then in vitro that ABA binds to LANCL2. This computational prediction was validated by SPR results and a binding assay with human LANCL2 [35]. We performed LANCL2-based virtual screening using the structure of LANCL2 obtained through homology modeling to discover new LANCL2 ligands. Compounds from NCI Diversity Set II, ChemBridge and ZINC natural products databases were docked into the LANCL2 model with Auto Dock and ranked by the calculated affinity. While ABA has high affinity for LANCL2, other diene-containing natural compounds such as 61610 were also predicted to bind in the same region and can also be pursued as LANCL2-binding drugs [12]. BT-11 also has demonstrated strong binding to LANCL2 and therapeutic efficacy in the NOD mouse model of T1D (FIG. 34). This data provides some validation that the LANCL2 pathway and the other compounds of the invention are useful as immune modulatory drugs for T1D. Further evidence in support of the role of the LANCL2 pathway as a means of modulating immune responses and ameliorating autoimmune diseases includes the LANCL2 binding and protective effects of ABA [22, 23], 61610 [12, 18] and BT-11 in mouse models of inflammatory bowel disease (IBD).

The incidence of T1D is increasing at an estimated annual rate of 3% worldwide [36-38]. While successful transplantation of pancreatic islets can treat T1D, the lack of sufficient islets, ongoing immune-mediated destruction of transplanted islets, and side effects from the immunosuppressive drugs greatly limits the widespread use of this approach [39]. As such, therapies that safely combine the ability of promoting pancreatic β-cell function and immune modulation are fundamental strategies to treat T1D. Our data demonstrate that activation of LANCL2 by BT-11 not only improves glucose levels in blood, but also improves its normalization after a glucose challenge (FIG. 34). Furthermore, treatment with BT-11 during the onset of T1d improves histopathology in the pancreas (FIG. 35). Indeed, ABA preventively and therapeutically suppresses inflammation and improves glucose tolerance [2, 3]. Thus, the natural activation of LANCL2 results in both immune modulation as illustrated by its therapeutic effects in IBD [12, 18, 22, 23] and regulation of glucose homeostasis due to suppressed inflammation and enhanced insulin sensitivity [2, 3]. Based on this background and data presented in FIGS. 34 and 35, investigating the role of LANCL2 as a therapeutic target for T1D is important.

Example 23

Use of BT-11 to Treat Type 2 Diabetes (T2D)

Introduction

Diabetes mellitus (DM) is a chronic condition that occurs when the body cannot produce enough or effectively use of insulin, and are induced by a genetic predisposition coupled with environmental factors. Unlike people with type 1 diabetes, type 2 diabetics are able to produce insulin. However, the pancreas of such patients does not make enough insulin or the body cannot use the insulin well enough. This phenomena is called insulin resistance. When there isn't enough insulin or the insulin is not used as it should be, glucose cannot be processed and used. As a result, when glucose is accumulated in the blood stream instead of going into cells and being metabolized, other cells in the system cannot function properly. Indeed, hyperglycemia and diabetes are important causes of morbidity and mortality, due to cardiovascular disease (CVD), nephropathy, neuropathy, foot ulcers, and retinopathy.

About 28.3 million Americans have type 2 diabetes (T2D) and over 40.1% of middle-aged adults have pre-diabetes, a condition characterized by impaired glucose tolerance, systemic inflammation and insulin resistance. The World Health Organization estimates that the number of people with T2D will increase to 366 million by the year 2030.

As stated above, current anti-diabetic medications are effective in improving insulin sensitivity, but their chronic administration has significant side effects such as cardiovascular complications, hepatotoxicity, weight gain, fluid retention, and bladder tumors. The lanthionine synthetase component C-like 2 (LANCL2) pathway exerts anti-diabetic actions with no side effects [18]. BT-11 binds to LANCL2, is orally active, has demonstrated anti-diabetic efficacy in mice and an outstanding safety profile.

Methods

Mice and dietary treatments. C57BL/6 and db/db, mice were purchased from the Jackson Laboratory and housed under specific pathogen-free conditions in ventilated racks. Mice in the Diet Induced Obesity diabetes model (DIO) were fed a high-fat diet (40 Kcal % fat). The mice were maintained in animal facilities. All experimental protocols were approved by an institutional animal care and use committee and met or exceeded guidelines of the National Institutes of Health Office of Laboratory Animal Welfare and Public Health Service policy.

Assessment of body weight and glucose tolerance. All mice were determined to be normoglycemic (fasting blood glucose levels lower than 250 mg/dl) and to have similar weights (weight±1.5 g) prior to the start of the study. Mice were weighed on a weekly basis and examined for clinical signs of disease by blinded observers. After a standard 12 h fast, glucose was determined on different days. Briefly, blood was collected via the lateral tail vein and placed onto capillary blood collection tubes. Mice then were administered a glucose tolerance test by intraperitoneal injection of D-glucose (2 g/kg body weight) and blood samples collected prior to the injection (time 0) (corresponding to a baseline FBG level following a 12-h fast starting at 6 a.m.) and at 15, 60, and 90 minutes (db/db model) or 15, 30, 60, 90, 120, 180, 220, and 265 minutes (DIO model) following the glucose injection. Abdominal (epididymal) white adipose tissue (WAT), subcutaneous WAT, and liver were then excised and weighed. Abdominal (epididymal) WAT was then digested and fractionated.

Digestion of white adipose tissue. Abdominal WAT was excised, weighed, minced into small <10 mg pieces and placed into digestion media (1× HBSS (Mediatech, Herndon, Va.) supplemented with 2.5% HEPES (Mediatech) and 10% fetal bovine serum containing type II collagenase (0.2%, Sigma-Aldrich)). Samples were incubated in a 37° C. incubator for 30 min, filtered through a 100 µm nylon cell strainer to remove undigested particles, and centrifuged at 4° C. at 1000× g for 10 min. The pellet, consisting of stromal vascular cells (SVCs), was washed with 1× HBSS and centrifuged at 4° C. at 1000× g for 10 min. The supernatant was discarded and erythrocytes were lysed by incubating the SVCs in 2 mL erythrocyte lysis buffer for 2 min before stopping the reaction with 9 mL 1× PBS. Cells were then respun at 4° C. at 1000× g for 10 min, suspended in 1 mL of 1× PBS, and counted with a Coulter Counter (Beckman Coulter, Fullerton, Calif.).

Immunophenotyping of Stromal Vascular Cells. For immunophenotyping SVCs were seeded into 96-well plates (Costar) at 2×105 cell/well. After an initial 20 min incubation with FcBlock (20 µg/mL; BD Biosciences-Pharmingen) to inhibit non-specific binding, cells were washed in PBS containing 5% serum and 0.09% sodium azide (FACS buffer) and stained with specific primary anti-mouse antibodies. Flow results were computed with a FacsAria flow cytometer and data analyses were performed with FACS DIVA™ (BD Biosciences) and FlowJo (TreeStar).

RealTime quantitative PCR. Total RNA was isolated from adipose tissue using the RNEASY Lipid Mini Kit (Qiagen) and from cells using the RNEASY Mini Kit (Qiagen) according to the manufacturer's instructions. Total RNA was used to generate complementary DNA (cDNA) template using the QSCRIPT™ cDNA Synthesis Kit (Quanta Biosciences, Gaithersburg, Md.). The total reaction volume was 20 µL with the reaction incubated as follows in an MJ MINI™ thermal cycler (Bio-Rad): 5 min at 25° C., 30 min at 52°, 5 min at 85° C., hold at 4° C. Each gene amplicon was purified with the MINELUTE PCR Purification Kit (Qiagen) and quantitated on an agarose gel by using a DNA mass ladder (Promega). These purified amplicons were used to optimize real-time PCR conditions in the real-time PCR assay. Primer concentrations and annealing temperatures were optimized for the CFX system (Bio-Rad) for each set of primers using the system's gradient protocol. PCR efficiencies were maintained between 92 and 105% and correlation coefficients above 0.98 for each primer set during optimization and also during the real-time PCR of sample DNA. Data is shown using the $\Delta\Delta Ct$ quantification method.

Results

Figure 36:
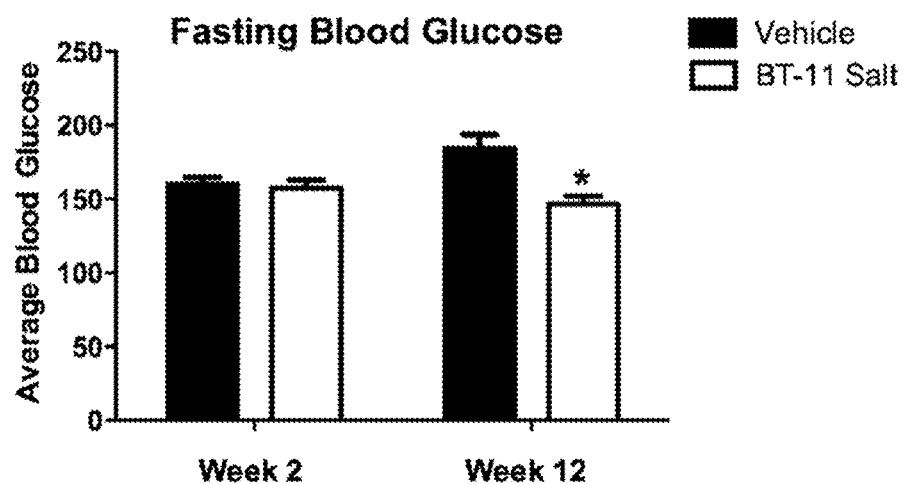
FIG. 36. Effect of oral BT-11 administration on (A) fasting blood glucose levels and (B) glucose tolerance test. (A) Mice were fasted for 12 h and blood glucose levels were assessed at weeks 2 and 12 after experiment set up. (B) Mice were also challenged with an IP glucose injection (2 g/Kg) and glucose was measured. Statistically significant differences (P<0.05) are indicated with an asterisk.
Figure 36:
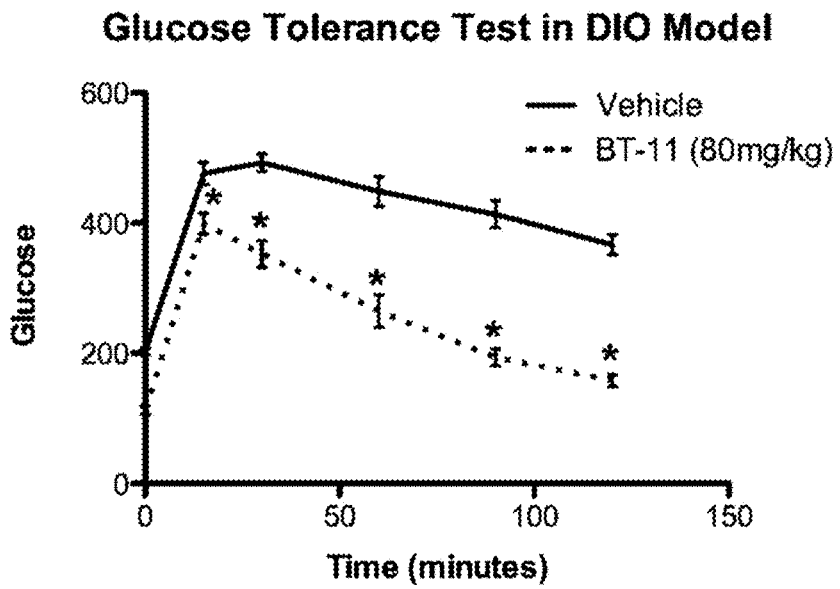

BT-11 reduced lasting blood glucose levels in a mouse DIO model of T2D. To assess the efficacy of the exemplary compound BT-11 in a model of T2D, we fed C57BL/6 mice a high fat diet (DIO model). Oral BT-11 administration significantly decreased the levels of blood glucose in BT-11 treated mice when compared to their vehicle-treated littermates at week 12 of high-fat feeding (FIG. 36, panel A). Furthermore, after 12 h fasting and glucose challenge at 2 g/Kg body weight via IP, mice treated with BT-11 were capable to normalize blood glucose levels significantly faster than untreated mice (FIG. 36, panel B).

Figure 37:
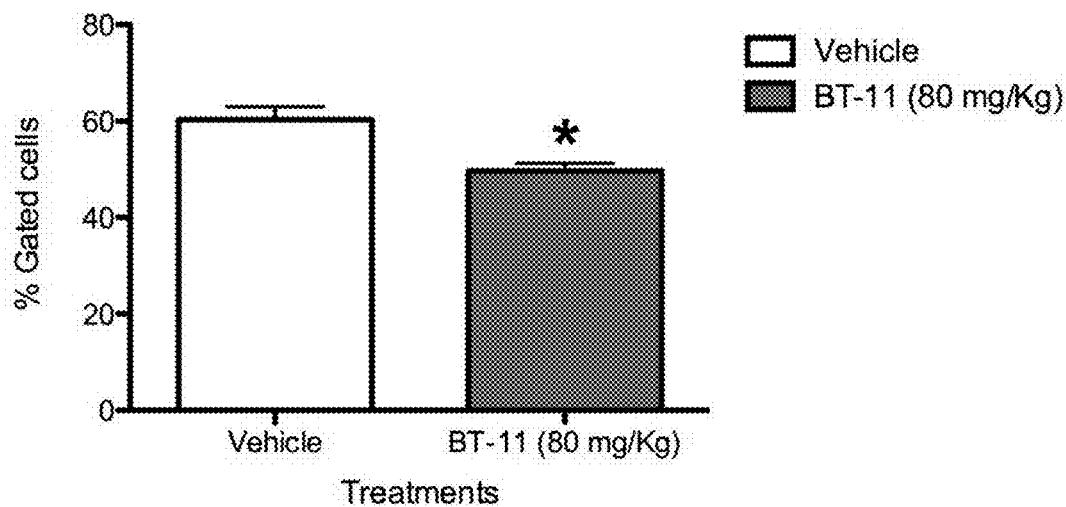
FIG. 37. Effect of oral BT-11 administration on pro-inflammatory populations infiltrating into the white adipose tissue (WAT). WAT was excised and digested and immunophenotyping results were assessed by flow cytometry. Levels of (A) infiltrating macrophages and (B) Ly6c$^{high}$ GR1+ infiltrating cells are shown. Statistically significant differences (P<0.05) are indicated with an asterisk.
Figure 37:
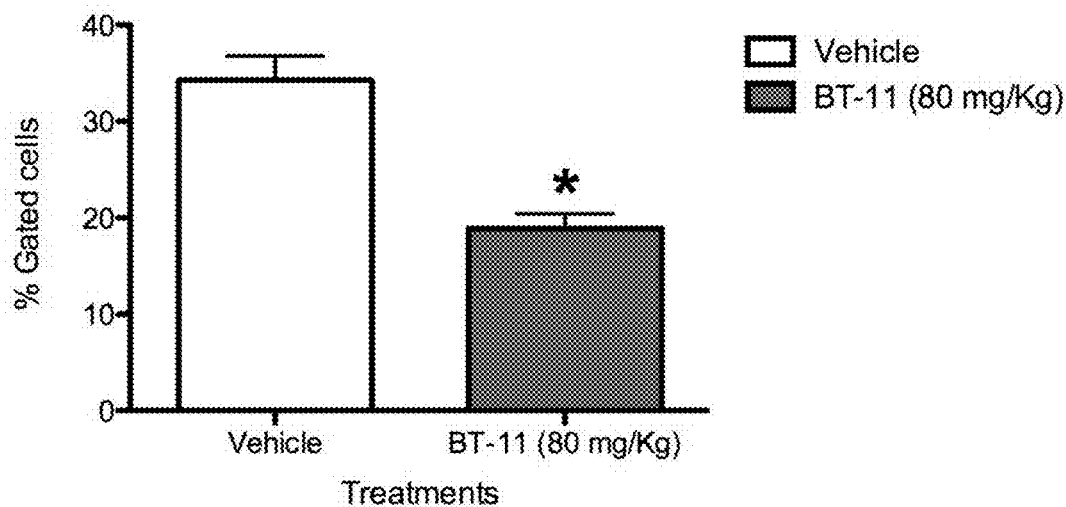

BT-11 treatment decreased pro-inflammatory macrophage infiltration as well as pro-inflammatory granulocytes in white adipose tissue. In order to characterize the cells infiltrating the white adipose tissue, abdominal WAT was collected and digested as specified in the methods section. Flow cytometry analyses were performed evaluating different pro-inflammatory populations in WAT. Our results show how treatment with BT-11 significantly reduced the levels of F4/80+ CD11b+ pro-inflammatory macrophages (FIG. 37, panel A), as well as the number of pro-inflammatory granulocytes with high levels of Ly6c (GR1+Ly6chigh) (FIG. 37, panel B).

Figure 38:
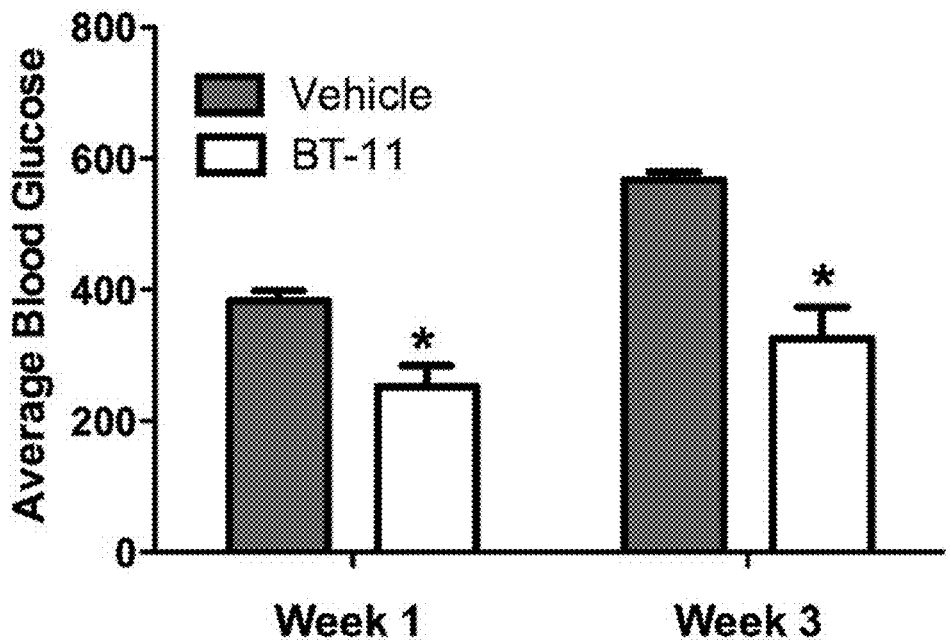
FIG. 38. Effect of oral BT-11 administration on glucose homeostasis in a db/db model of diabetes. (A) Fasting blood glucose (FBG) concentrations from leptin receptor-deficient (db/db) mice treated with either BT-11 or vehicle at weeks 1 and 3 after experiment set up are shown. (B) Plasma glucose levels after intraperitoneal glucose challenge (1 g/Kg body weight) are shown. Blood was collected before (0), then 15, 30, 60, 90, 120, 180, 220, and 265 minutes after glucose load. Statistically significant differences between groups (P<0.05) are indicated with an asterisk.
Figure 38:
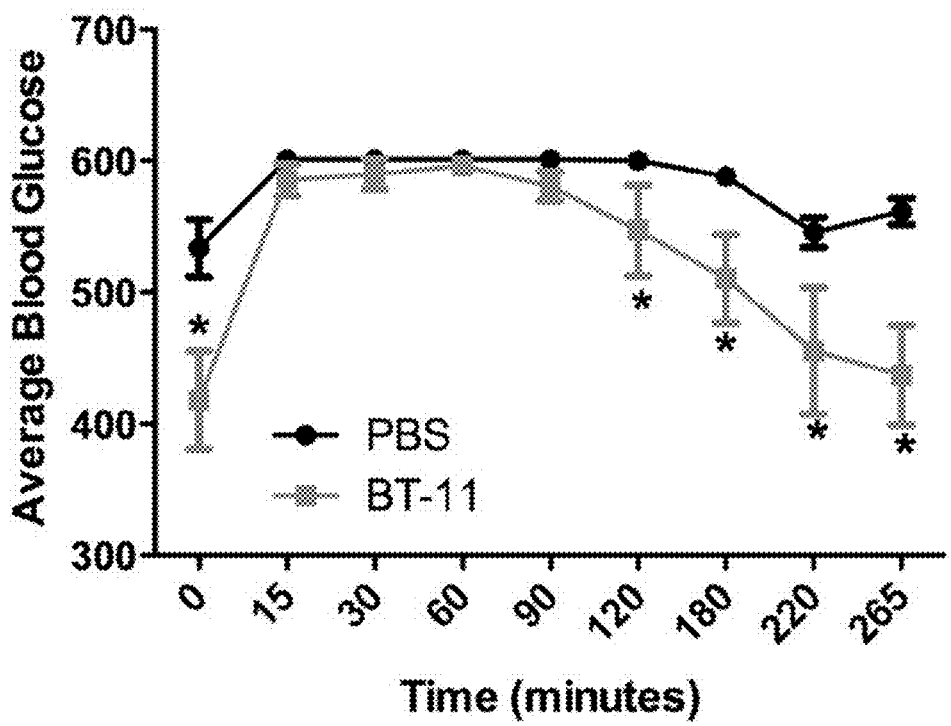

BT-11 reduced fasting blood glucose levels in a mouse db/db model of T2D. To evaluate the therapeutic efficacy of oral BT-11 treatment in two mouse models of diabetes, we also used the db/db mice, which develops spontaneous T2D due to a mutation in the leptin receptor. Db/db mice were administered a daily dose of BT-11 at 80 mg/Kg by oral gavage. We determined the effect of BT-11 on glucose homeostasis by measuring fasting blood glucose concentrations. Treatment with BT-11 significantly decreased the levels of blood glucose in comparison to their vehicle-treated littermates as early as in one week, accentuating the differences over time at week 3 (FIG. 38, panel A). To determine whether oral BT-11 treatment modulates how the animal initiates glucose homeostasis, we gave an intraperitoneal glucose challenge to experimental animals and evaluated the kinetics of plasma glucose from 0 to 265 minutes following glucose injection. Blood samples collected prior to the injection (time 0) (corresponding to a baseline FBG level following a 12-h fast). Our results show how oral treatment with BT-11 significantly decreases the levels of glucose prior to the IP glucose challenge (Time 0, FIG. 38, panel B). Following glucose challenge in the db/db model, our results show how glucose levels in mice treated with our top lead compounds BT-11, fell toward normal levels more rapidly than in the vehicle-treated mice (FIG. 38, panel B).

Figure 39:
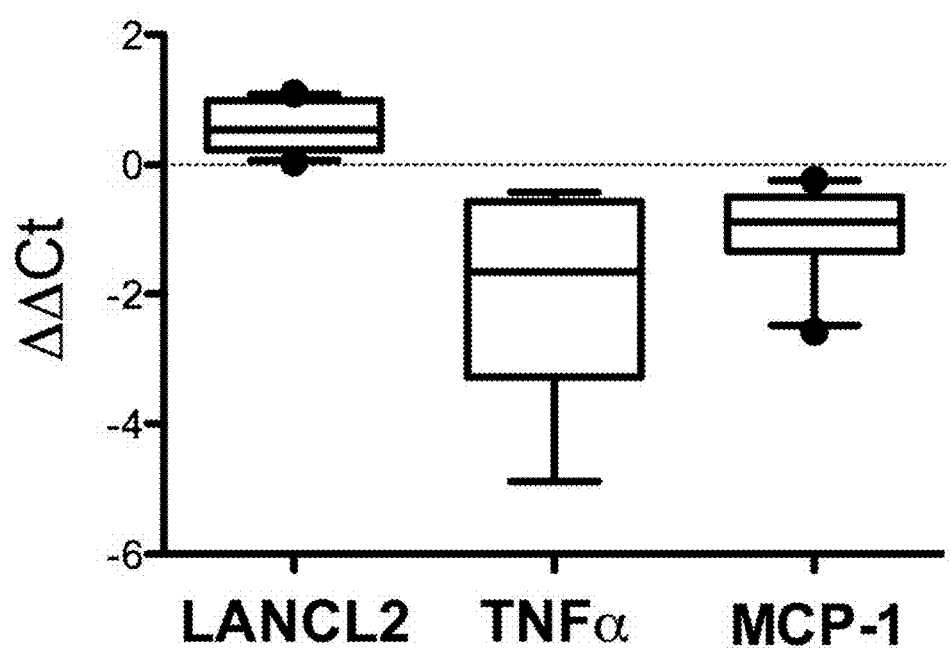
FIG. 39. Effect of oral BT-11 administration on expression of LANCL2, TNFα, and MCP-1 in white adipose tissue (WAT) from mice with diet-induced obesity. Gene expression analysis of LANCL2, TNFα, and MCP-1 was evaluated compared to the untreated mice. The line at zero represents the baseline of mice that received vehicle only.

BT-11 reduced mRNA levels of TNFα and MCP-1 and upregulated LANCL2. To further confirm the anti-inflammatory potency of BT-11, we assessed gene expression on WAT as indicated in the methods section. Our results show how when compared to untreated mice, mice treated with BT-11 have higher expression levels of LANCL2 and significantly lower mRNA levels of the pro-inflammatory factor TNFα and MCP-1 (FIG. 39).

Discussion

As the rates of obesity and Type 2 Diabetes (T2D) in the U.S. continue to rise, an increasingly large number of people are becoming reliant on oral anti-diabetic drugs. About 28.3 million (8.3% of the population) Americans have T2D and over 40.1% of middle-aged adults had pre-diabetes, a condition characterized by impaired glucose tolerance and insulin resistance [40]. The total direct and indirect costs attributable to T2D in the United States are over $132 billion [40]. Despite this growing problem, pharmaceutical manufacturers have been unable to develop medications that are both safe and effective. One of the most popular and effective oral anti-diabetic medications is the thiazolidinedione (TZD) class of insulin-sensitizing drugs. Although TZDs enhance insulin sensitivity, they have significant adverse side effects that have limited their availability, including weight gain, congestive heart failure, bladder cancer, hepatotoxicity and fluid retention [41, 42]. For instance, approximately 10-15% of patients using TZDs are forced to discontinue treatment due to edema, and the increase in extracellular volume from excess fluid retention also poses a major problem for individuals with preexisting congestive heart failure. In 2000, troglitazone (REZULIN®) was removed from the market, 3 years after its inception, due to reports of serious liver injury and death [43]. Safety concerns about other TZDs resulted in mandatory black box labeling and subsequent restrictions for use.

LANCL2 was the second member of the LanC-like protein family to be identified. The first member, LANCL1, was isolated from human erythrocyte membranes [44]. LANCL2 was subsequently identified and expressed throughout the body [1, 18], including immune cells, pancreas, lung and intestine [1, 44]. The lanthionine synthetase C-like 2 (LANCL2) pathway has emerged as a novel therapeutic target for T2D [18]. Extensive pre-clinical testing provides ample evidence of the therapeutic potential for LANCL2 ligands such as abscisic acid (ABA) in diabetes and chronic inflammatory diseases [2, 3, 22, 23, 45]. Compound 61610, a bis(benzimidazoyl)terephthalanilide (BTT) binds to LANCL2 with the highest affinity in a library of several million chemicals.

Given the fact that current drugs for T2D fail to satisfy the patient first need, which is glycemic control, without side effects, BT-11 represents a very attractive potential substitute. Our results show how the administration of BT-11 in different mouse models of T2D significantly lowers the glucose levels in blood after a period of fasting (FIGS. 36 and 38). Moreover, the administration of this compound also helps normalize glucose levels after a glucose challenge (FIGS. 36 and 38). The anti-inflammatory properties of BT-11 are also reflected in our immunophenotyping results. Indeed, administration of BT-11 resulted in less infiltration of pro-inflammatory macrophages and pro-inflammatory granulocytes in abdominal WAT (FIG. 37). These results were supported by gene expression data of two very important pro-inflammatory factors, TNFα and MCP-1, which were found significantly reduced in mice treated with BT-11 (FIG. 39).

Example 24

Use of BT-11 During Influenza Infection

Introduction

Respiratory pathogens causing pneumonia are the leading cause of infectious disease-related death in industrialized countries. The absence of effective vaccines and anti-virals coupled with growing concerns over the emergence of anti-viral resistance highlights a need for developing host-targeted immunotherapeutic approaches. The pulmonary pathogenesis and clinical disease associated with respiratory infections often result from a combination of the cytopathic effects of the virus and the host immune response. In this regard, therapies directed at modulating the innate immune response are considered for the treatment of flu [46].

Influenza remains a major public health problem worldwide. Seasonal influenza is associated with an upper respiratory tract process which is often incapacitating and requires days of restricted activity. It has been estimated that in the United States alone, annual flu epidemics result in 30 million outpatient visits and 300,000 hospital admissions. Certain populations (e.g., young children, the elderly, and people with predisposing medical conditions) are at higher risk of developing viral pneumonia. Experts have estimated that 25,000 to 35,000 people die annually from seasonal flu in the US, and the global financial burden has been calculated to he hundreds of billions of dollars [47]. Pandemic influenza cycles occur every 30-50 years with added complexity due to their unpredictable presentation and lack of pre-existing immunity, and are associated with high mortality rates [48]. Influenza is associated with significant morbidity and mortality, but effective and safe drug treatments are lacking.

Data that suggests lanthionine synthetase component C-like protein 2 (LANCL2) is a target for the binding and signaling of ABA [15, 19, 24]. Thus, LANCL2 has emerged as a promising novel therapeutic target for immune modulation. Using molecular modeling and surface plasmon resonance (SPR), BTI has identified compound BT-11, a bis(benzimidazoyl)terephthalanilide (BTT), which binds to LANCL2 with high affinity. Also, BT-11 exerted potent pro-resolutive effects in the lungs, and decreased mortality and morbidity in mouse models of influenza.

Methods

Mice. C57BL/6 mice were purchased from the Jackson Laboratory and housed under specific pathogen-free conditions in ventilated racks. All experimental protocols were approved by an institutional animal care and use committee and met or exceeded guidelines of the National Institutes of Health Office of Laboratory Animal Welfare and Public Health Service policy.

Intranasal infection of mice with influenza virus. Mice were anesthetized with 2-5% isofluorane using a vaporizer station, and 50 µL of virus dilution at $10^3$ TCID50 was administered through the nostrils (25 µL each one). Mice were then placed in their cages and watched for recovery of anesthesia.

Oral administration of BT-11 by orogastric gavage. BT-11 was administered to mice by orogastric gavage using a commercially available safety ball-tipped gavage needle (18-24 gauge, depending on the weight of the animal). This procedure caused no pain or distress. Mice were treated with BT-11 at a dose of 80 mg/Kg every 24 h for the duration of the experiment.

Monitoring of mice and disease activity and weighing. Mice were monitored once daily after the infection (or every 4 hours if they developed severe clinical signs of disease equivalent to disease score 2) and were euthanized prior to the planned endpoint if they developed significant signs of illness as measured by weight loss (i.e., 25% gradual loss of initial body weight), dehydration, loss of mobility, guarding/ protection of painful area, ruffled fur (piloerection). Mice were weighed once a day for the duration of the experiment.

Results

Oral administration of BT-11 reduced clinical scores and morbidity in mice with influenza virus.

Figure 40:
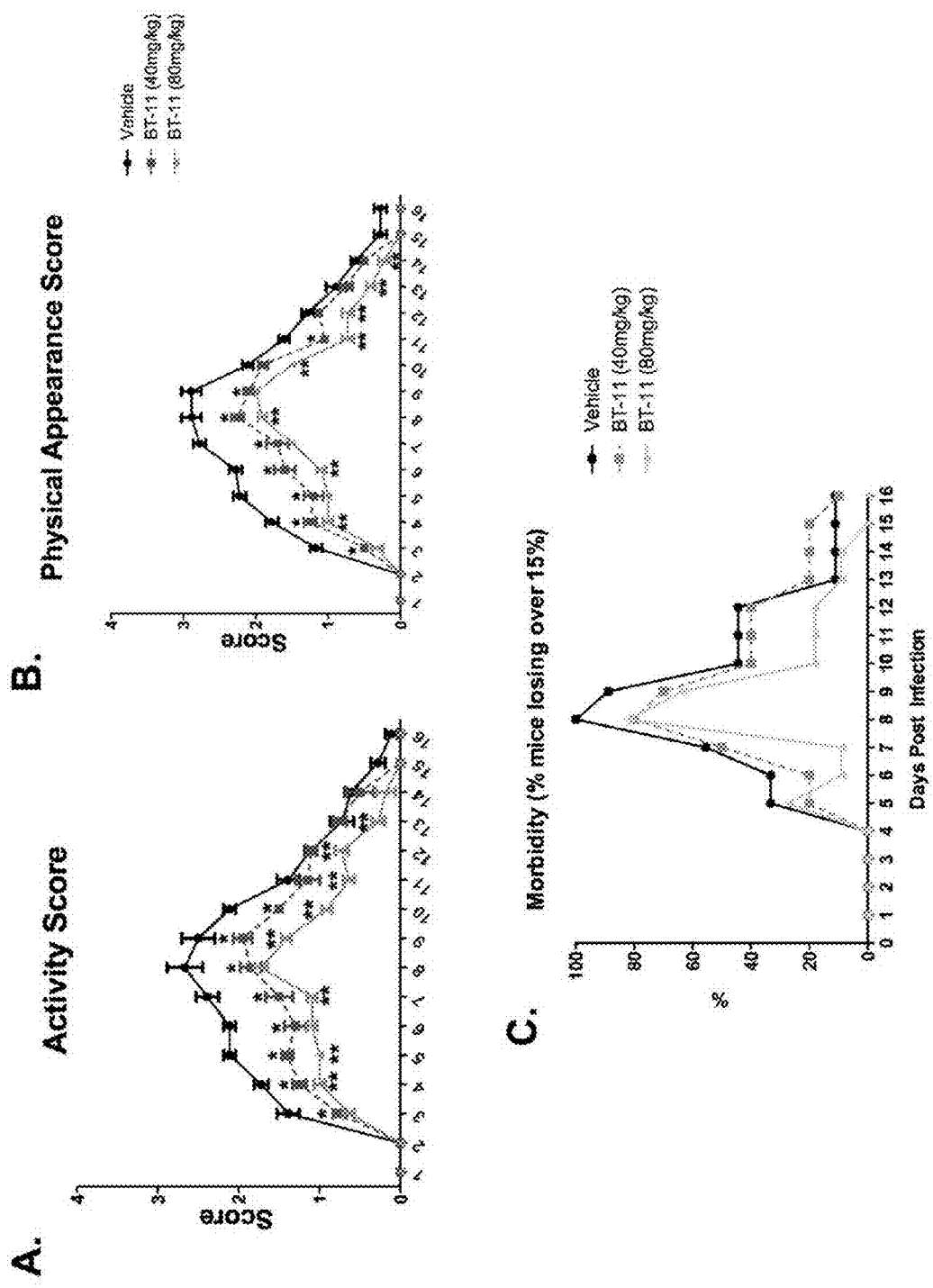
FIG. 40. Effect of oral BT-11 administration on clinical scores and morbidity of mice infected with Influenza virus. Mice were infected with influenza virus and clinically scored throughout the experiment. Clinical scores were noted for (A) activity and (B) physical appearance. (C) The percentage of mice that lost more than 15% of body weight was plotted to show changes in morbidity. Statistically significant differences between groups (P<0.05) are indicated with an asterisk.

To evaluate the therapeutic efficacy of BT-11, we used a mouse model of influenza infection in mice. Briefly, mice were infected intranasally after anesthesia with 5% isofluorane. Mice were daily treated with an oral suspension of BT-11 at 80 or 40 mg/Kg. Mice were weighed and scored for the duration of the experiment (16 days). Results show how administration of BT-11 significantly reduced the activity clinical score starting at day 3 and throughout the experiment (FIG. 40, panel A). Furthermore, the clinical score for physical appearance was significantly reduced in mice receiving the treatment with both 40 and 80 mg/Kg of BT-11 (FIG. 40, panel B).

In order to evaluate the effect of the treatment in disease morbidity, we calculated the percentage of weight loss and further evaluated the number of mice losing over 15% within each experimental group. Starting at day 6 post-infection, the treatment with 80 mg/Kg of BT-11 resulted in less morbidity when comparing to the vehicle group. The differences accentuated starting at day 10 and through day 12 (FIG. 40, panel C).

Discussion

Traditional approaches to control influenza spread and disease are centered on the virus side through vaccination and antiviral treatment. Vaccines have to be formulated annually based on the circulating strains from the previous season. However it takes about 4 to 6 months to produce, license, and test the efficacy of a new vaccine [49], whether it is for seasonal or pandemic flu. The main disadvantage of antivirals is the very frequent emergence and selection of resistant strains. In addition to virus-centered treatments, the development of therapies based on controlling exacerbated host responses have a very high likelihood of being adopted to complement anti-microbial and prophylactic strategies. Host-targeted therapeutics have the advantage of offering cross protection among different reasortants, and thus being efficacious from season to season, they can be produced and stocked, and can be used to treat the disease after virus exposure [46, 50, 51].

The identification of LANCL2 as a novel therapeutic target for influenza opens a new avenue for host-targeted therapeutics. We demonstrated that activation of LANCL2 by BT-11 improves not only activity and clinical scores, but also decreases morbidities caused by the influenza virus, and accelerates the recovery from influenza infection (FIG. 33). These results strongly support that LANCL2 is a novel therapeutic target for influenza and BT-11 is a potential new host-targeted drug.

REFERENCES

1. Mayer, H., M. Pongratz, and R. Prohaska, Molecular cloning, characterization, and tissue-specific expression of human LANCL2, a novel member of the LanC-like protein family. *DNA Seq,* 2001. 12(3): p. 161-6.
2. Guri, A. J., et al., Dietary abscisic acid ameliorates glucose tolerance and obesity-related inflammation in db/db mice fed high-fat diets. *Clin Nutr,* 2007. 26(1): p. 107-16.
3. Guri, A. J., et al., Loss of PPAR gamma in immune cells impairs the ability of abscisic acid to improve insulin sensitivity by suppressing monocyte chemoattractant protein-1 expression and macrophage infiltration into white adipose tissue. *J Nutr Biochem,* 2008. 19(4): p. 216-28.
4. Bassaganya-Riera, J., et al., Mechanisms of action and medicinal applications of abscisic Acid. *Curr Med Chem,* 2010. 17(5): p. 467-78.
5. Guri, A. J., R. Hontecillas, and J. Bassaganya-Riera, Abscisic acid synergizes with rosiglitazone to improve glucose tolerance and down-modulate macrophage accumulation in adipose tissue: possible action of the cAMP/PKA/PPAR gamma axis. *Clin Nutr,* 2010. 29(5): p. 646-53.
6. Guri, A. J., R. Hontecillas, and J. Bassaganya-Riera, Abscisic acid ameliorates experimental IBD by down-regulating cellular adhesion molecule expression and suppressing immune cell infiltration. *Clin Nutr,* 2010. 29(6): p. 824-31.
7. Guri, A. J., et al., Abscisic acid ameliorates atherosclerosis by suppressing macrophage and CD4+ T cell recruitment into the aortic wall. *J Nutr Biochem,* 2010. 21(12): p. 1178-85.
8. Bassaganya-Riera, J., et al., Abscisic acid regulates inflammation via ligand-binding domain-independent activation of peroxisome proliferator-activated receptor gamma. *J Biol Chem,* 2011. 286(4): p. 2504-16.
9. Guri, A. J., et al., T cell PPARgamma is required for the anti-inflammatory efficacy of abscisic acid against experimental IBD. *J Nutr Biochem,* 2011. 22(9): p. 812-9.
10. Lu, P., et al., Molecular modeling of lanthionine synthetase component C-like protein 2: a potential target for the discovery of novel type 2 diabetes prophylactics and therapeutics. *J Mol Model,* 2011. 17(3): p. 543-53.
11. Hontecillas, R., et al., Dietary abscisic acid ameliorates influenza-virus-associated disease and pulmonary immunopathology through a PPARgamma-dependent mechanism. *J Nutr Biochem,* 2013. 24(6): p. 1019-27.
12. Lu, P., et al., Computational modeling-based discovery of novel classes of anti-inflammatory drugs that target lanthionine synthetase C-like protein 2. *PLoS One,* 2012. 7(4): p. e34643.
13. Lu, P., et al., Lanthionine synthetase component C-like protein 2: a new drug target for inflammatory diseases and diabetes. *Curr Drug Targets,* 2014. 15(6): p. 565-72.
14. Trott, O. and A. J. Olson, AutoDock Vina: improving the speed and accuracy of docking with a new scoring function, efficient optimization, and multithreading. *J Comput Chem,* 2010. 31(2): p. 455-61.
15. Lu, P., et al., Molecular modeling of lanthionine synthetase component C-like 2: a potential target for the discovery of novel type 2 diabetes prophylactics and therapeutics. *Journal of Molecular Modeling,* 2011. 17(3): p. 543-53.
16. Morris, G. M., et al., AutoDock4 and AutoDockTools4: Automated docking with selective receptor flexibility. *J Comput Chem,* 2009. 30(16): p. 2785-91.
17. Lichtenstein, G. R., M. Abreu, and D. Present, Recent advances in the treatment of Crohn's colitis, 2003, The center for health care education, LLC.
18. Lu, P., et al., Lanthionine Synthetase Component C-like Protein 2: A New Drug Target for Inflammatory Diseases and Diabetes. *Curr Drug Targets,* 2014.

19. Sturla, L., et al., LANCL2 is necessary for abscisic acid binding and signaling in human granulocytes and in rat insulinoma cells. *J Biol Chem*, 2009. 284(41): p. 28045-57.
20. Hanauer, S. B. and D. H. Present, The state of the art in the management of inflammatory bowel disease. *Rev Gastroenterol Disord*, 2003. 3(2): p. 81-92.
21. Lindsay, J. O. and H. J. Hodgson, Review article: the immunoregulatory cytokine interleukin-10—a therapy for Crohn's disease? *Aliment Pharmacol Ther*, 2001. 15(11): p. 1709-16.
22. Guri, A. J., R. Hontecillas, and J. Bassaganya-Riera, Abscisic acid ameliorates experimental IBD by down-regulating cellular adhesion molecule expression and suppressing immune cell infiltration. *Clinical Nutrition*, 2010. 29(6): p. 824-31.
23. Guri, A. J., et al., T cell PPAR gamma is required for the anti-inflammatory efficacy of abscisic acid against experimental inflammatory bowel disease. *Journal of Nutritional Biochemistry*, 2011. 22(9): p. 812-9.
24. Bassaganya-Riera, J., et al., Abscisic acid regulates inflammation via ligand-binding domain-independent activation of PPAR gamma. *Journal of Biological Chemistry*, 2011. 286(4): p. 2504-16.
25. Lu, P., et al., Computational modeling-based discovery of novel classes of anti-inflammatory drugs that target LANCL2. *PLoS One*, 2012. In Press.
26. Stenson, W. F., Interleukin-4 hyporesponsiveness in inflammatory bowel disease: immune defect or physiological response? *Gastroenterology*, 1995. 108(1): p. 284-6.
27. Cohen, R. D., et al., The cost of hospitalization in Crohn's disease. *Am J Gastroenterol*, 2000. 95(2): p. 524-30.
28. Barba, G., et al., Recurrent pancreatitis revealing Crohn's disease. *Arch Pediatr*, 2002. 9(10): p. 1053-5.
29. Braverman, I. M., Skin signs of gastrointestinal disease. *Gastroenterology*, 2003. 124(6): p. 1595-614.
30. Marri, S. R. and A. L. Buchman, The education and employment status of patients with inflammatory bowel diseases. *Inflamm Bowel Dis*, 2005. 11(2): p. 171-7.
31. Spunt, S., et al., Cancer Epidemiology in Older Adolescents and Young Adults 15 to 29 Years of Age, in SEER AYA Monograph. 2008, National Cancer Institute: Bethesda, Md. p. 123-133.
32. Camilleri, M., GI clinical research 2002-2003: The year in review. *Clinical Gastroenterology and Hepatology*, 2003. 1: p. 415-420.
33. Guri, A. J., R. Hontecillas, and J. Bassaganya-Riera, Abscisic acid synergizes with rosiglitazone to improve glucose tolerance and down-modulate macrophage accumulation in adipose tissue: possible action of the cAMP/PKA/PPAR gamma axis. *Clinical Nutrition*, 2010. 29(5): p. 646-653.
34. Bruzzone, S., et al., Abscisic Acid Is an Endogenous Stimulator of Insulin Release from Human Pancreatic Islets with Cyclic ADP Ribose as Second Messenger. *J Biol Chem*, 2008. 283(47): p. 32188-32197.
35. Sturla, L., et al., Binding of abscisic acid to human LANCL2. *Biochem Biophys Res Commun*, 2011. 415(2): p. 390-5.
36. Sparre, T., et al., Unraveling the pathogenesis of type 1 diabetes with proteomics: present and future directions. *Mol Cell Proteomics*, 2005. 4(4): p. 441-57.
37. Vehik, K., et al., Increasing incidence of type 1 diabetes in 0- to 17-year-old Colorado youth. *Diabetes Care*, 2007. 30(3): p. 503-9.
38. Ma, R. C. and J. C. Chan, Diabetes: incidence of childhood type 1 diabetes: a worrying trend. *Nat Rev Endocrinol*, 2009. 5(10): p. 529-30.
39. Suarez-Pinzon, W. L., J. R. Lakey, and A. Rabinovitch, Combination therapy with glucagon-like peptide-1 and gastrin induces beta-cell neogenesis from pancreatic duct cells in human islets transplanted in immunodeficient diabetic mice. *Cell Transplant*, 2008. 17(6): p. 631-40.
40. CDC. National Diabetes Fact Sheet: general information and national estimates on diabetes in the United States, 2005. in U. S. Department of Health and Human Services, Center for Disease Control and Prevention, 2005. 2005. Atlanta, Ga.
41. Bassaganya-Riera, J., A. Guri, J. King, and R. Hontecillas, Peroxisome Proliferator-Activated Receptors: the Nutritionally Controlled Molecular Networks that Integrate Inflammation, Immunity and Metabolism. *Current Nutrition & Food Science*, 2005. 1: p. 179-187.
42. Nesto, R. W., et al., Thiazolidinedione use, fluid retention, and congestive heart failure: a consensus statement from the American Heart Association and American Diabetes Association. Oct. 7, 2003, *Circulation*, 2003. 108 (23): p. 2941-8.
43. Wysowski, D. K., G. Armstrong, and L. Governale, Rapid increase in the use of oral antidiabetic drugs in the United States, 1990-2001. *Diabetes Care*, 2003. 26(6): p. 1852-5.
44. Mayer, H., et al., Isolation, molecular characterization, and tissue-specific expression of a novel putative G protein-coupled receptor. *Biochim Biophys Acta*, 1998. 1395(3): p. 301-8.
45. Hontecillas, R., et al., Dietary abscisic acid ameliorates influenza virus-associated disease and pulmonary immunopathology through a PPAR g-dependent mechanism. *Journal of Nutritional Biochemistry*, 2012. 24(6): p. 1019-27.
46. Enserink M. Infectious disease. Old drugs losing effectiveness against flu; could statins fill gap? *Science*. 2005 Sep. 23; 309(5743):1976-7.
47. Rothberg, M. B., S. D. Haessler, and R. B. Brown, Complications of viral influenza. *Am J Med*. 2008. 121 (4): p. 258-64.
48. Dawood F S, et al. Estimated global mortality associated with the first 12 months of 2009 pandemic influenza A H1N1 virus circulation: a modelling study. *Lancet Inject Dis*. 2012 September; 12(9):687-95.
49. Quigley, E., Influenza therapies: vaccines and antiviral drugs. *Drug Discov Today*, 2006. 11(11-12): p. 478-80.
50. Butler D. Cheaper approaches to flu divide researchers. *Nature*. 2007 Aug. 30; 448(7157):976-7.
51. Fedson D S. Confronting an influenza pandemic with inexpensive generic agents: can it be done? *Lancet Infect Dis*. 2008 September; 8(9):571-6.
52. Melo F, Feytmans E. Assessing protein structures with a non-local atomic interaction energy. *J Mol Biol*. 1998 Apr. 17; 277(5):1141-52.
53. SMILES Translator and Converter. http://cactus.nci.nih.gov/translate/.

We claim:

1. A method of treating a condition in an animal with a compound, the method comprising administering an effective amount of the compound to the animal, wherein the condition is selected from the group consisting of inflammatory bowel disease, diabetes, and influenza infection, wherein the compound is a compound of formula:

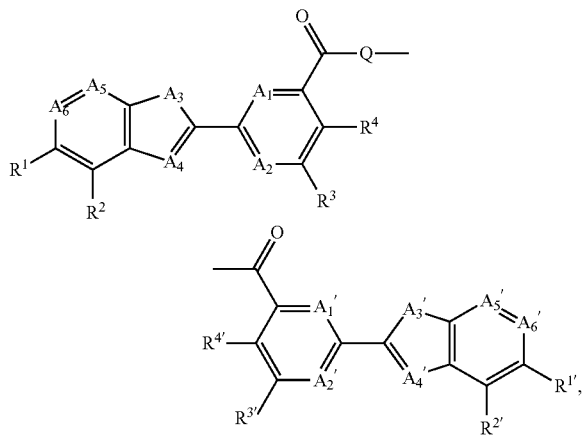

or a pharmaceutically acceptable salt or ester thereof, wherein:
Q is piperazine-1,4-diyl; 2,5-diazabicyclo[2.2.1]heptane-2,5-diyl; 2,5-diazabicyclo[2.2.2]octane-2,5-diyl; or substituted piperazine-1,4-diyl substituted with one to eight substituents in the 2, 3, 5, or 6 positions, wherein each substituent on the substituted piperazine-1,4-diyl is independently selected from the group consisting of ($C_1$ to $C_6$)alkyl, aryl, aryl($C_1$ to $C_6$)alkyl, C(O)OH, and C(O)O($C_1$ to $C_6$)alkyl;
$A_1$ and $A_1'$ are each independently N or $CR^6$;
$A_2$ and $A_2'$ are each independently N or $CR^7$;
$A_3$ and $A_3'$ are each independently $NR^8$, O, or S;
$A_4$ and $A_4'$ are each independently N or $CR^9$;
$A_5$ and $A_5'$ are each independently $CR^{10}$;
$A_6$ and $A_6'$ are each independently $CR^{11}$; and
$R^1$, $R^{1'}$, $R^2$, $R^{2'}$, $R^3$, $R^{3'}$, $R^4$, $R^{4'}$, $R^6$, $R^7$, $R^8$, $R^9$, $R^{10}$, and $R^{11}$, if present, are in each instance independently selected from the group consisting of hydrogen, alkyl, halo, trifluoromethyl, dialkylamino wherein each alkyl is the same or different, —$NH_2$, alkylamino, aryl, and arylalkyl.

2. The method of claim 1 wherein the condition is influenza infection.

3. The method of claim 1 wherein the condition is inflammatory bowel disease.

4. The method of claim 3 wherein the inflammatory bowel disease is ulcerative colitis.

5. The method of claim 1 wherein the condition is diabetes.

6. The method of claim 1 wherein $A_4$ is N.

7. The method of claim 1 wherein $A_3$ is $NR^8$ and $A_4$ is N.

8. The method of claim 1 wherein at least one of $A_3$ and $A_3'$ is $NR^8$ and wherein $A_4$ and $A_4'$ are each N.

9. The method of claim 1 wherein at least one of $A_1$, $A_2$, $A_1'$, and $A_2'$ is N.

10. The method of claim 1 wherein $R^1$, $R^{1'}$, $R^2$, $R^{2'}$, $R^3$, $R^{3'}$, $R^4$, $R^{4'}$, $R^6$, $R^7$, $R^8$, $R^9$, $R^{10}$, and $R^{11}$, if present, are in each instance independently selected from the group consisting of hydrogen, alkyl, halo, and trifluoromethyl.

11. The method of claim 1 wherein $R^1$, $R^{1'}$, $R^2$, $R^{2'}$, $R^3$, $R^{3'}$, $R^4$, $R^{4'}$, $R^6$, $R^7$, $R^8$, $R^9$, $R^{10}$, and $R^{11}$, if present, are in each instance independently selected from the group consisting of hydrogen and halo.

12. The method of claim 1 wherein $R^1$, $R^{1'}$, $R^2$, $R^{2'}$, $R^3$, $R^{3'}$, $R^4$, $R^{4'}$, $R^6$, $R^7$, $R^8$, $R^9$, $R^{10}$, and $R^{11}$, if present, are each hydrogen.

13. The method of claim 1 wherein Q is piperazine-1,4-diyl or substituted piperazine-1,4-diyl substituted with one to eight substituents in the 2, 3, 5, or 6 positions, wherein each substituent on the substituted piperazine-1,4-diyl is independently selected from the group consisting of ($C_1$ to $C_6$)alkyl, aryl, aryl($C_1$ to $C_6$)alkyl, C(O)OH, and C(O)O($C_1$ to $C_6$)alkyl.

14. The method of claim 13 wherein at least one of $A_3$ and $A_3'$ is $NR^8$ and wherein $A_4$ and $A_4'$ are each N.

15. The method of claim 14 wherein $R^1$, $R^{1'}$, $R^2$, $R^{2'}$, $R^3$, $R^{3'}$, $R^4$, $R^{4'}$, $R^6$, $R^7$, $R^8$, $R^9$, $R^{10}$, and $R^{11}$, if present, are in each instance independently selected from the group consisting of hydrogen, alkyl, halo, and trifluoromethyl.

16. The method of claim 15 wherein Q is piperazine-1,4-diyl or substituted piperazine-1,4-diyl substituted with one to eight substituents in the 2, 3, 5, or 6 positions, wherein each substituent on the substituted piperazine-1,4-diyl is independently selected from the group consisting of ($C_1$ to $C_6$)alkyl, C(O)OH, and C(O)O($C_1$ to $C_6$)alkyl.

17. The method of claim 1 wherein the compound has the structure of:

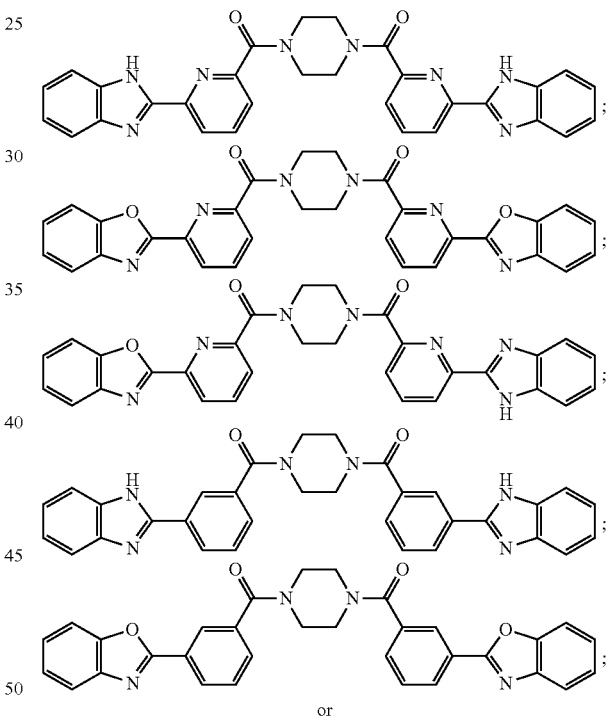

or salts thereof.

18. The method of claim 3 wherein the inflammatory bowel disease is Crohn's disease.

19. The method of claim 5 wherein the diabetes is type 1 diabetes.

20. The method of claim 5 wherein the diabetes is type 2 diabetes.

21. The method of claim 1 wherein Q is 2.5 diazabicyclo[2.2.1]heptane-2.5-diyl.

22. The method of claim 1 wherein Q is 2.5-diazabicyclo[2.2.2]octane-2.5-diyl.

* * * * *